US012611506B2

(12) United States Patent
    Dobrovolsky et al.

(10) Patent No.:    US 12,611,506 B2
(45) Date of Patent:     Apr. 28, 2026

(54) AUTOMATIC INJECTION DEVICE

(71) Applicant: E3D A.C.A.L, Merom Hagalil (IL)

(72) Inventors: Vanya Dobrovolsky, Kiiryat Bialik
(IL); Amotz Porat, West Galilee (IL);
Michael Segev, Lower Galilee (IL);
Tsachi Shaked, Merom Hagalil (IL)

(73) Assignee: E3D A.C.A.L., Merom Hagalil (IL)

( * ) Notice: Subject to any disclaimer, the term of this
patent is extended or adjusted under 35
U.S.C. 154(b) by 835 days.

(21) Appl. No.: 17/908,369

(22) PCT Filed: Mar. 29, 2021

(86) PCT No.: PCT/IL2021/050351
§ 371 (c)(1),
(2) Date: Aug. 31, 2022

(87) PCT Pub. No.: WO2021/199034
PCT Pub. Date: Oct. 7, 2021

(65) Prior Publication Data
US 2023/0105397 A1     Apr. 6, 2023

Related U.S. Application Data

(60) Provisional application No. 63/002,339, filed on Mar.
30, 2020.

(51) Int. Cl.
*A61M 5/28*         (2006.01)
*A61M 5/20*         (2006.01)
       (Continued)

(52) U.S. Cl.
CPC ............ *A61M 5/20* (2013.01); *A61M 5/2033*
(2013.01); *A61M 5/28* (2013.01);
       (Continued)

(58) Field of Classification Search
CPC ........ A61M 5/20; A61M 5/2033; A61M 5/28;
A61M 5/31515; A61M 5/3204;
       (Continued)

(56) References Cited
U.S. PATENT DOCUMENTS 7,717,877 B2    5/2010   Lavi et al.
7,976,499 B2    7/2011   Grunhut et al.
       (Continued)

FOREIGN PATENT DOCUMENTS

AU      2008261698 B2    6/2013
EP         2311510 B1    5/2014
       (Continued)

OTHER PUBLICATIONS

Int'l Search Report and Written Opinion issued Jun. 9, 2021 in Int'l
Application No. PCT/IL21/50351.
       (Continued)

*Primary Examiner* — Tasnim Mehjabin Ahmed
(74) *Attorney, Agent, or Firm* — Panitch Schwarze
Belisario & Nadel LLP

(57) ABSTRACT

An automatic injection device, including a housing arranged
along a longitudinal axis and having a forward end and a
rearward end, the housing is configured to receive a syringe
including at least one syringe piston and a needle coupled to
a forward end thereof; a plunger rod adapted to be retained
with respect to the housing in an initial operative orientation;
at least one resilient element arranged to forwardly bias the
plunger rod relative to the syringe; a needle shield adapted
for selectable axial displacement with respect to the housing
along the longitudinal axis, whereas rearward displacement
of the needle shield exposes the needle and forward dis-
placement of the needle shield covers the needle; and a
trigger element configured to be axially rearwardly dis-
placed upon rearward displacement of the needle shield
       (Continued)

relative to the housing and thereby allow forward displacement of the plunger rod relative to the syringe under the urge of the at least one resilient element.

18 Claims, 51 Drawing Sheets

(51) Int. Cl.
*A61M 5/315* (2006.01)
*A61M 5/32* (2006.01)

(52) U.S. Cl.
CPC ...... *A61M 5/31515* (2013.01); *A61M 5/3204* (2013.01); *A61M 5/3213* (2013.01); *A61M 2005/2013* (2013.01); *A61M 2005/3247* (2013.01); *A61M 2005/3267* (2013.01); *A61M 2205/581* (2013.01)

(58) Field of Classification Search
CPC ........ A61M 5/3213; A61M 2005/2013; A61M 2005/3247; A61M 2005/3267; A61M 2205/581
See application file for complete search history.

(56) References Cited

U.S. PATENT DOCUMENTS

| | | | |
|---|---|---|---|
| 8,496,619 | B2 | 7/2013 | Kramer et al. |
| 8,932,254 | B2 | 1/2015 | Eaton |
| 8,945,049 | B2 | 2/2015 | Hommann |
| 9,352,101 | B2 | 5/2016 | Roberts |
| 9,364,611 | B2 | 6/2016 | Kramer et al. |
| 9,427,528 | B2 | 8/2016 | Hommann |
| 9,446,195 | B2 | 9/2016 | Kramer et al. |
| 10,201,658 | B2 | 2/2019 | Kemp et al. |
| 10,485,933 | B2 | 11/2019 | Vogt et al. |
| 10,493,213 | B2 | 12/2019 | Hommann |
| 2002/0161337 | A1 | 10/2002 | Shaw et al. |
| 2005/0101919 | A1* | 5/2005 | Brunnberg ............ A61M 5/326 604/197 |
| 2010/0274185 | A1 | 10/2010 | Chun |
| 2011/0144594 | A1* | 6/2011 | Sund ................. A61M 5/31571 604/228 |
| 2012/0323186 | A1 | 12/2012 | Karlsen et al. |
| 2013/0211330 | A1* | 8/2013 | Pedersen .............. A61M 5/326 604/111 |
| 2013/0281939 | A1 | 10/2013 | Roberts et al. |
| 2014/0088505 | A1 | 3/2014 | Fabien et al. |
| 2016/0375195 | A1 | 12/2016 | Fabien |
| 2017/0021103 | A1 | 1/2017 | Mosebach et al. |

FOREIGN PATENT DOCUMENTS

| | | | |
|---|---|---|---|
| EP | 2217308 | B1 | 7/2016 |
| EP | 2714155 | B1 | 9/2016 |
| EP | 2739329 | B1 | 12/2017 |
| EP | 2661294 | B1 | 8/2020 |
| JP | 2017185255 | A | 10/2017 |
| NZ | 520174 | A | 8/2004 |
| NZ | 608925 | A | 10/2014 |
| NZ | 701052 | A | 1/2016 |
| WO | 2008005315 | A2 | 1/2008 |
| WO | 2019234134 | A1 | 12/2019 |
| WO | 2020014292 | A1 | 1/2020 |

OTHER PUBLICATIONS

Extended European Search Report issued on Mar. 6, 2024 in EP Application No. 21779469.2.

* cited by examiner

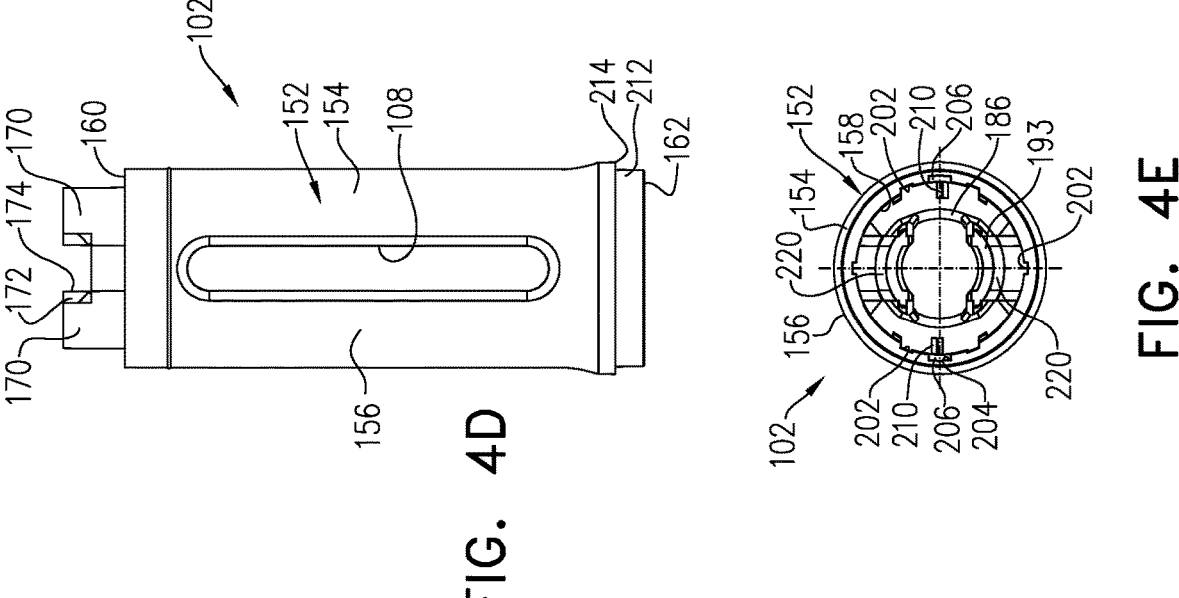
FIG. 4D
FIG. 4E
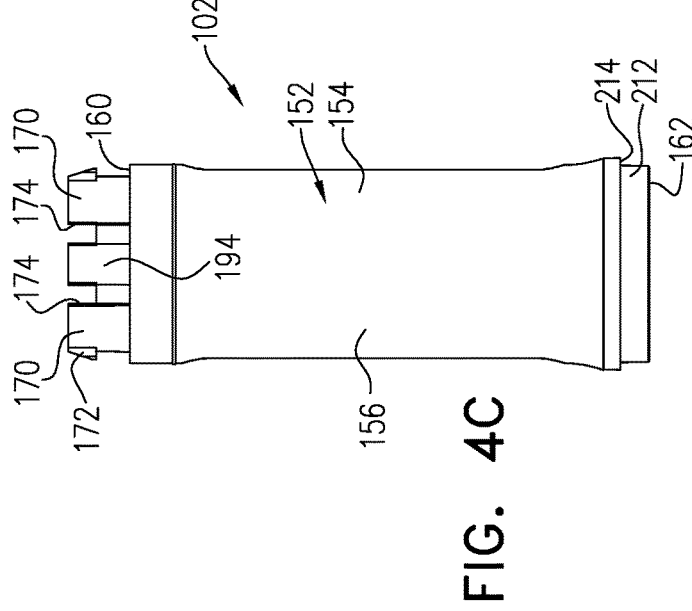
FIG. 4C

AUTOMATIC INJECTION DEVICE

CROSS-REFERENCE TO RELATED APPLICATIONS

This application is a Section 371 of International Application No. PCT/IL2021/050351, filed Mar. 29, 2021, which was published on Oct. 7, 2021, under International Publication No. WO 2021/199034 A1, which claims priority to U.S. Provisional Patent Application No. 63/002,339, filed Mar. 30, 2020, the contents of which are incorporated herein by reference.

FIELD OF THE INVENTION

The present invention generally relates to an auto injector, and more specifically to an auto-injector adapted for parenteral administration of substances (e.g., a medication) to a living organism (human or animal) by means of pressing the auto injector against an injection site.

BACKGROUND OF THE INVENTION

Various automatic injectors are known, such that are activatable by means of pressing the automatic injector against an injection site on the skin of a patient. It is important to ensure the needle is protected at all times before, during and after injection of the medicament.

SUMMARY OF THE INVENTION

The present invention seeks to provide an automatic injection device.

There is thus provided in accordance with an embodiment of the present invention or a combination of embodiments thereof, an automatic injection device comprising a housing arranged along a longitudinal axis and having a forward end and a rearward end, configured to receive a syringe including at least one syringe piston and a needle configured to be coupled to a forward end thereof; a plunger rod adapted to be retained with respect to the housing in an initial operative orientation; at least one resilient element arranged to forwardly bias the plunger rod relative to the syringe; a needle shield adapted for selectable axial displacement with respect to the housing along the longitudinal axis, whereas rearward displacement of the needle shield exposes the needle and forward displacement of the needle shield covers the needle; and a trigger element configured to be axially rearwardly displaced upon rearward displacement of the needle shield relative to the housing and thereby allow forward displacement of the plunger rod relative to the syringe under the urge of the at least one resilient element.

Preferably, the trigger element is rearwardly spaced from a rearward end of the needle shield in an initial operative orientation and is configured to prevent forward displacement of the plunger rod under the biasing force of the at least one resilient element up to the rearward displacement of the needle shield relative to the housing. Further preferably, the syringe is static with respect to the housing. Even further preferably, the trigger element is operatively engageable with a housing portion, wherein the housing portion prevents axial displacement of the plunger rod relative to the syringe. Yet further preferably, the trigger element radially supports the housing portion.

In accordance with an embodiment of the present invention, the plunger rod is allowed to be displaced under the urge of the at least one resilient element upon rearward displacement of the trigger element by the needle shield, which in turn allows radial outward deflection of the housing portion.

Preferably, the at least one resilient element is at least partially disposed within the plunger rod. Further preferably, the needle shield is prevented from forward displacement relative to the housing both in an initial operative orientation and in a final operative orientation, when the needle is protected by the needle shield, by means of engagement of a resilient needle shield portion with a protrusion formed on the housing. Yet further preferably, the protrusion is configured to laterally displace the resilient needle shield portion in a first direction during rearward displacement of the needle shield relative to the housing and in a second direction during forward displacement of the needle shield relative to the housing. Even further preferably, an audible indication is provided at an end of injection operative orientation by engagement of the plunger rod with the housing.

Preferably, the housing comprises at least one locking arm, which is operative both for retaining the plunger rod in a rearward position and for providing an audible indication for an end of injection.

In accordance with an embodiment of the present invention, an automatic injection device comprising a housing arranged along a longitudinal axis and having a forward end and a rearward end, configured to receive a syringe including at least one syringe piston and a needle configured to be coupled to a forward end thereof; a plunger rod adapted to be retained with respect to the housing in an initial operative orientation; at least one resilient element arranged to forwardly bias the plunger rod relative to the syringe; a needle shield adapted for selectable axial displacement with respect to the housing along the longitudinal axis, whereas rearward displacement of the needle shield exposes the needle and forward displacement of the needle shield covers the needle; and a trigger element, which is rearwardly spaced from a rearward end of the needle shield in an initial operative orientation and is configured to prevent forward displacement of the plunger rod under the biasing force of the at least one resilient element up to rearward displacement of the needle shield relative to the housing.

Preferably, the trigger element is configured to be axially rearwardly displaced upon the rearward displacement of the needle shield relative to the housing and thereby allow forward displacement of the plunger rod relative to the syringe under the urge of the at least one resilient element. Further preferably, the trigger element is operatively engageable with a housing portion, wherein the housing portion prevents axial displacement of the plunger rod relative to the syringe. Yet further preferably, the trigger element radially supports the housing portion. Still further preferably, the plunger rod is allowed to be displaced under the urge of the at least one resilient element upon rearward displacement of the trigger element by the needle shield, which in turn allows radial outward deflection of the housing portion.

In accordance with an embodiment of the present invention, the at least one resilient element is at least partially disposed within the plunger rod. Preferably, the needle shield is prevented from forward displacement relative to the housing both in the initial operative orientation and in a final operative orientation, when the needle is protected by the needle shield, by means of engagement of a resilient needle shield portion with a protrusion formed on the housing.

Further preferably, the protrusion is configured to laterally displace the resilient needle shield portion in a first direction during rearward displacement of the needle shield relative to the housing and in a second direction during forward displacement of the needle shield relative to the housing. Still further preferably, the syringe is static with respect to the housing. Yet further preferably, an audible indication is provided at an end of injection operative orientation by engagement of the plunger rod with the housing. Further preferably, the housing comprises at least one locking arm, which is operative both for retaining the plunger rod in a rearward position and for providing an audible indication for an end of injection.

In accordance with an embodiment of the present invention, an automatic injection device comprising a housing arranged along a longitudinal axis and having a forward end and a rearward end and having an inwardly extending protrusion formed thereon, the housing is configured to receive a syringe including at least one syringe piston and a needle configured to be coupled to a forward end thereof; a plunger rod adapted to be retained with respect to the housing in an initial operative orientation; at least one resilient element arranged to forwardly bias the plunger rod relative to the syringe; a needle shield adapted for selectable axial displacement with respect to the housing along the longitudinal axis, whereas rearward displacement of the needle shield exposes the needle and forward displacement of the needle shield covers the needle; and wherein the needle shield is prevented from forward displacement relative to the housing both in an initial operative orientation and in a final operative orientation, when the needle is protected by the needle shield, by means of engagement of a resilient needle shield portion with the inwardly extending protrusion.

Preferably, the automatic injection device also comprising a trigger element, which is rearwardly spaced from a rearward end of the needle shield in the initial operative orientation and is configured to prevent forward displacement of the plunger rod under the biasing force of the at least one resilient element up to rearward displacement of the needle shield relative to the housing. Further preferably, the trigger element is configured to be axially rearwardly displaced upon the rearward displacement of the needle shield relative to the housing and thereby allow forward displacement of the plunger rod relative to the syringe under the urge of the at least one resilient element.

Still further preferably, the trigger element is operatively engageable with a housing portion, wherein the housing portion prevents axial displacement of the plunger rod relative to the syringe. Yet further preferably, the trigger element radially supports the housing portion.

In accordance with an embodiment of the present invention, the plunger rod is allowed to be displaced under the urge of the at least one resilient element upon rearward displacement of the trigger element by the needle shield, which in turn allows radial outward deflection of the housing portion.

Preferably, the at least one resilient element is at least partially disposed within the plunger rod. Further preferably, the protrusion is configured to laterally displace the resilient needle shield portion in a first direction during rearward displacement of the needle shield relative to the housing and in a second direction during forward displacement of the needle shield relative to the housing.

Still further preferably, the syringe is static with respect to the housing. Yet further preferably, an audible indication is provided at an end of injection operative orientation by engagement of the plunger rod with the housing. Preferably, the housing comprises at least one locking arm, which is operative both for retaining the plunger rod in a rearward position and for providing an audible indication for an end of injection.

BRIEF DESCRIPTION OF THE DRAWINGS

The present invention will be understood and appreciated more fully from the following detailed description, taken in conjunction with the drawings in which:

FIGS. 4A, 4B, 4C, 4D, 4E, 4F, 4G, 4H & 4I are respectively a simplified perspective view of a rearward-facing portion, a simplified perspective view of a forward-facing portion, two simplified side plan views, a simplified top plan view, a simplified bottom view and three simplified sectional views taken along lines H-H, G-G and I-I in FIG. 4F of a front housing portion forming part of the front sub-assembly of the automatic injection device of FIGS. 1A and 1B;

DESCRIPTION OF EMBODIMENTS

Figures 1A, 1B:
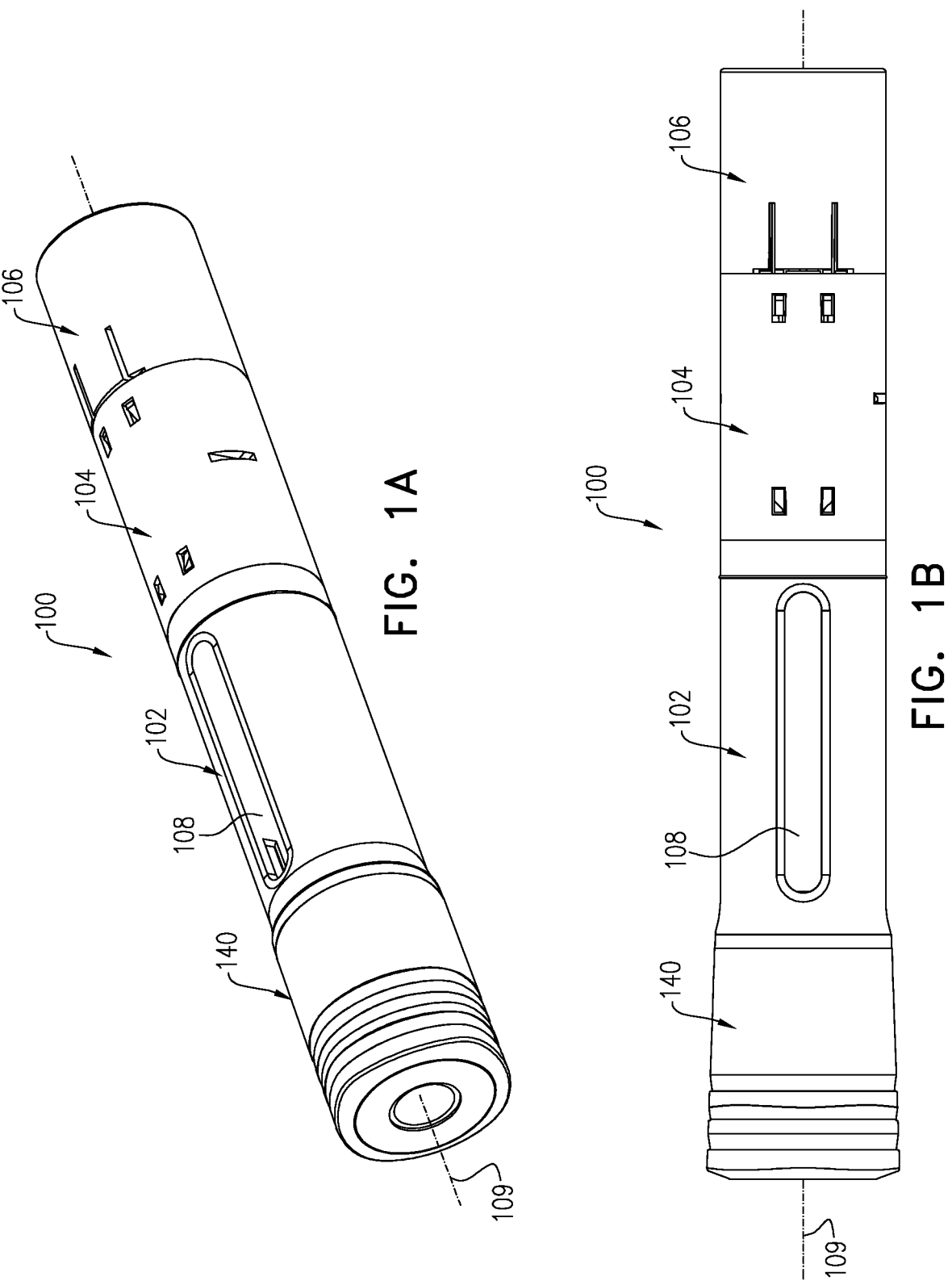
FIGS. 1A and 1B are respectively simplified pictorial and side plan view of an automatic injection device constructed and operative in accordance with an embodiment of the present invention.

The principles, uses and implementations of the teachings herein may be better understood with reference to the accompanying description and figures. Upon perusal of the description and figures present herein, one skilled in the art is able to implement the invention without undue effort or experimentation.

Before explaining at least one embodiment of the invention in detail, it is to be understood that the invention is not limited in its applications to the details of construction and the arrangement of the components and/or methods set forth in the following description and/or illustrated in the drawings and/or the Examples. The invention can be implemented with other embodiments and can be practiced or carried out in various ways. It is also understood that the phraseology and terminology employed herein is for descriptive purpose and should not be regarded as limiting.

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

Figure 2:
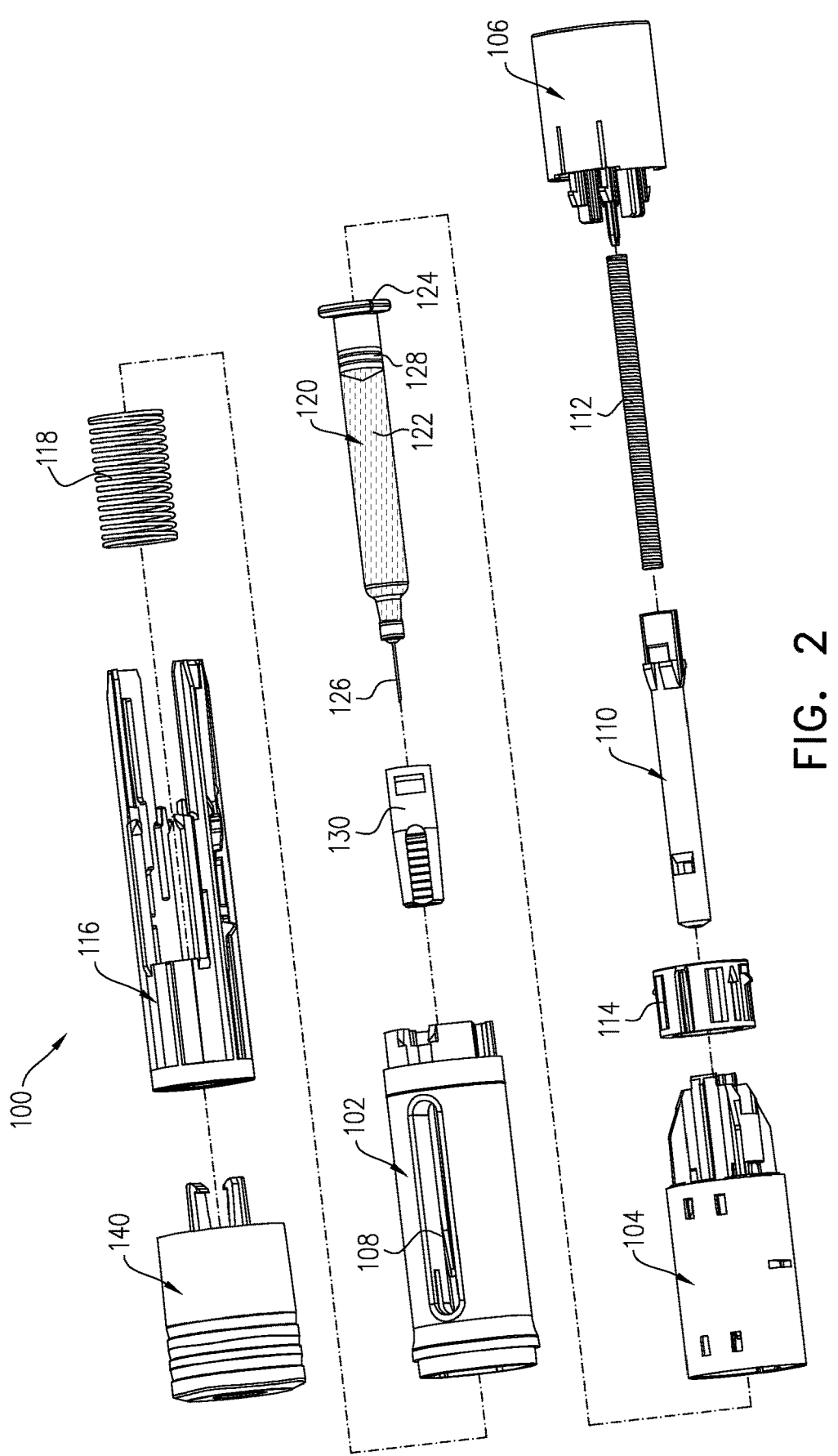
FIG. 2 is a simplified exploded view of the automatic injection device of FIGS. 1A and 1B.

Reference is now made to FIGS. 1A & 1B, which are respectively simplified pictorial and side plan view of an automatic injection device constructed and operative in accordance with an embodiment of the present invention. Reference is additionally made to FIG. 2, which is a simplified exploded view of the automatic injection device of FIGS. 1A & 1B.

As seen in FIGS. 1A-2, an automatic injection device 100 comprises a front housing portion 102, a rear housing portion 104, and a rear cover 106, which are preferably fixedly attached to each other, such as by a snap-fit engagement. It is noted that the front housing portion 102 is formed with a window 108 to permit viewing of a portion of the contents of the automatic injection device 100 therethrough. It is noted that the front housing portion 102, the rear housing portion 104 and the rear cover 106 are arranged along a mutual longitudinal axis 109.

Disposed within the enclosure formed by the front housing portion 102, the rear housing portion 104 and the rear cover 106 is a plunger rod 110, which is adapted to at least partially receive an injection spring 112 thereinto, the plunger rod 110 is biased to be axially longitudinally displaced forwardly along longitudinal axis 109 under the force of the injection spring 112, but is operatively blocked from longitudinal displacement in certain operative orientations of the automatic injection device 100 by means of a trigger ring 114. Trigger ring 114 is axially slidably arranged within the rear housing portion 104 and provides for coupling of the plunger rod 110 with the rear housing portion 104 before actuation of the automatic injection device 100 and thereby prevents axial longitudinal displacement of the plunger rod 110 before actuation of the automatic injection device 100.

A needle guard element 116 is axially slidably disposed partially within the front housing portion 102 and partially within the rear housing portion 104 and is arranged along longitudinal axis 109. The needle guard element 116 protrudes forwardly from the front housing portion 102 and is operative to be biased axially forwardly under the force of a needle guard spring 118.

It is a particular feature of an embodiment of the present invention that the needle guard element 116 is longitudinally forwardly spaced from the trigger ring 114 before actuation of the automatic injection device 100.

A pre-filled syringe 120 is configured to be preferably fixedly held between the front housing portion 102 and the rear housing portion 104. The pre-filled syringe 120 has a syringe barrel 122 having a flange 124 formed at its rearward end and a needle 126 fixedly attached to its forward end. A piston 128 is contained within the syringe barrel 122, which confines the medicament within the syringe barrel 122. A cover 130, suitable for single use, is adapted to seal and protect the needle 126. It is appreciated that syringe 120 can be any type of medicament container, such as pre-filled syringe or cartridge.

A needle cover remover 140 is adapted to be mounted over the forward portion of the needle guard element 116 and of the front housing portion 102 to protect the needle 126 in storage and permit removal of the cover 130 before injection. The needle cover remover 140 is also arranged along longitudinal axis 109.

Figure 3:
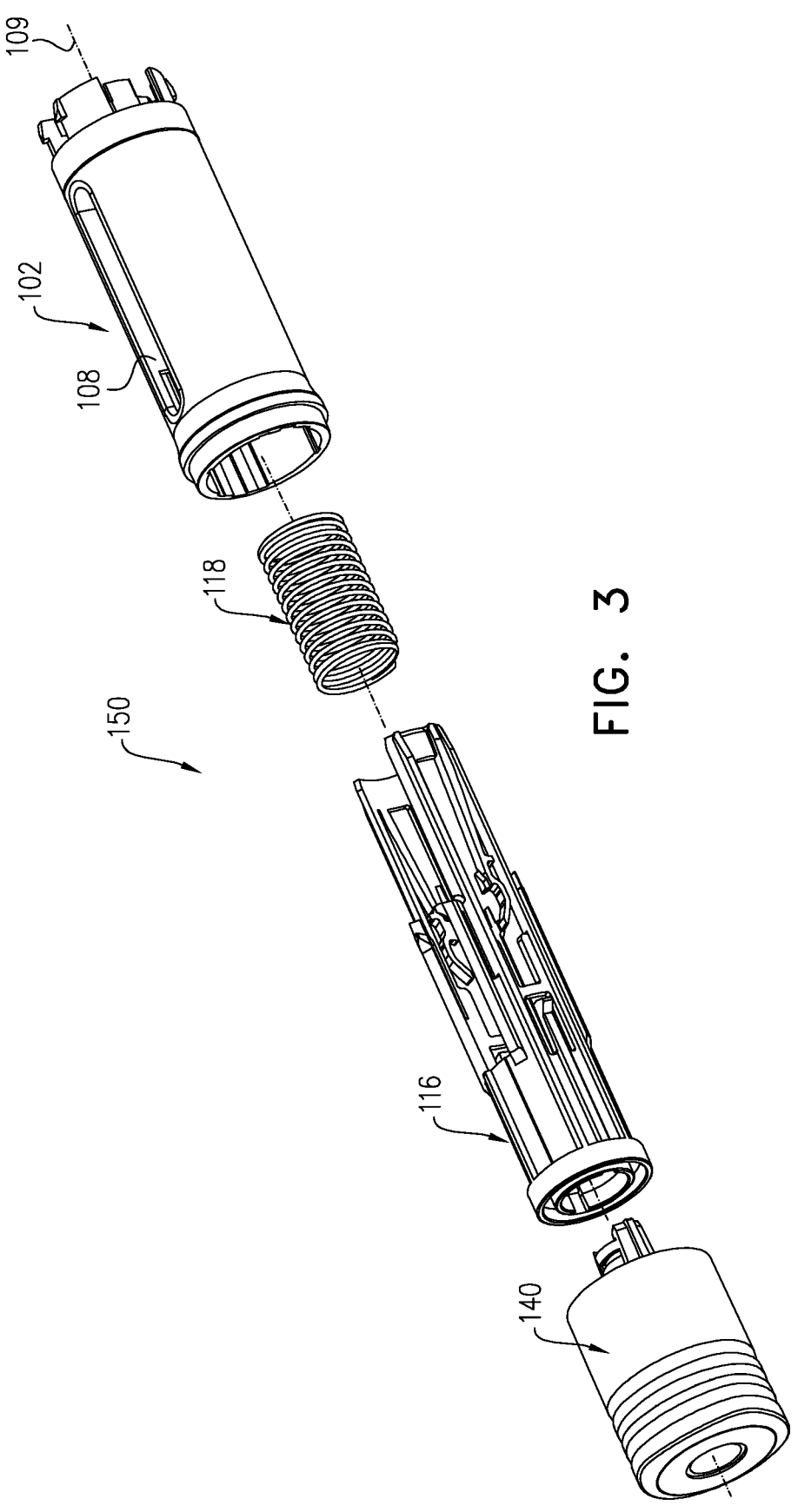
FIG. 3 is a simplified exploded view of a front sub-assembly of the automatic injection device of FIGS. 1A and 1B.

Reference is now made to FIG. 3, which is a simplified exploded view of a front sub-assembly of the automatic injection device 100 of FIGS. 1A and 1B. Reference is additionally made to FIGS. 4A, 4B, 4C, 4D, 4E, 4F, 4G, 4H & 4I, which are respectively a simplified perspective view of a rearward-facing portion, a simplified perspective view of a forward-facing portion, two simplified side plan views, a simplified top plan view, a simplified bottom view and three simplified sectional views taken along lines H-H, G-G and I-I in FIG. 4F of the front housing portion 102 forming part of the front sub-assembly of the automatic injection device of 100 FIGS. 1A and 1B.

A front sub-assembly 150 is shown in FIG. 3, which includes front housing portion 102, needle guard spring 118, needle guard element 116 and needle cover remover 140, which are all mutually arranged along longitudinal axis 109.

Referring now specifically to FIGS. 4A-4I, the front housing portion 102 preferably is an integrally formed element, preferably injection molded of plastic and is arranged along longitudinal axis of symmetry 109.

The front housing portion 102 has a preferably cylindrical portion 152 defining a circumferential wall 154 having an outer surface 156 and an inner surface 158. Windows 108, previously mentioned with reference to FIGS. 1A-2, are formed in cylindrical portion 152. The cylindrical portion 152 defines a rearward edge 160 and a forward edge 162.

Typically, two pairs of radially spaced diametrically opposed rearwardly extending protrusions 170 extend rearwardly from rearward edge 160. The rearwardly extending protrusions 170 have an outwardly extending locking tooth 172 formed thereon. Each of the rearwardly extending protrusions 170 defines a preferably mutually inwardly facing edge 174.

A generally cylindrical internal syringe containing portion 180 is coaxially arranged within cylindrical portion 152 and is attached thereto by means of connect ribs 181, defining a rearward end 182 and a forward end 183. The syringe containing portion 180 defines a rearwardly facing end edge 184 and a forwardly facing end edge 186. Two mutually facing forwardly extending arms 190 extend forwardly from the forwardly facing end edge 186. An inspection window 192 is formed in each of the forwardly extending arms 190, which is preferably aligned with one of the windows 108 formed in the cylindrical portion 152. Rearwardly facing end edge 184 is preferably axially rearwardly spaced from rearward edge 160. The forwardly extending arms 190 terminate at forward end edges 193. Forward ends 183 of the connecting ribs 181 are preferably rearwardly spaced from forward end edges 193.

Typically, two rearwardly extending protrusions 194 extend from rearwardly facing end edge 184 and each of the protrusions 194 is radially disposed between the two pairs of protrusions 170.

A syringe containing bore 200 is defined within portion 180.

It is seen in FIGS. 4A-4I that a plurality of axial longitudinal grooves 202 are formed on the inner surface 158 of the cylindrical portion 152 for alignment and guiding of the needle guard element 116. A plurality of longitudinal partial grooves 204 are also formed on the inner surface 158 of cylindrical portion 152. The partial grooves 204 are radially spaced from grooves 202 and extend rearwardly to terminate at a forwardly tapered surface 206.

Figures 4A, 4B:
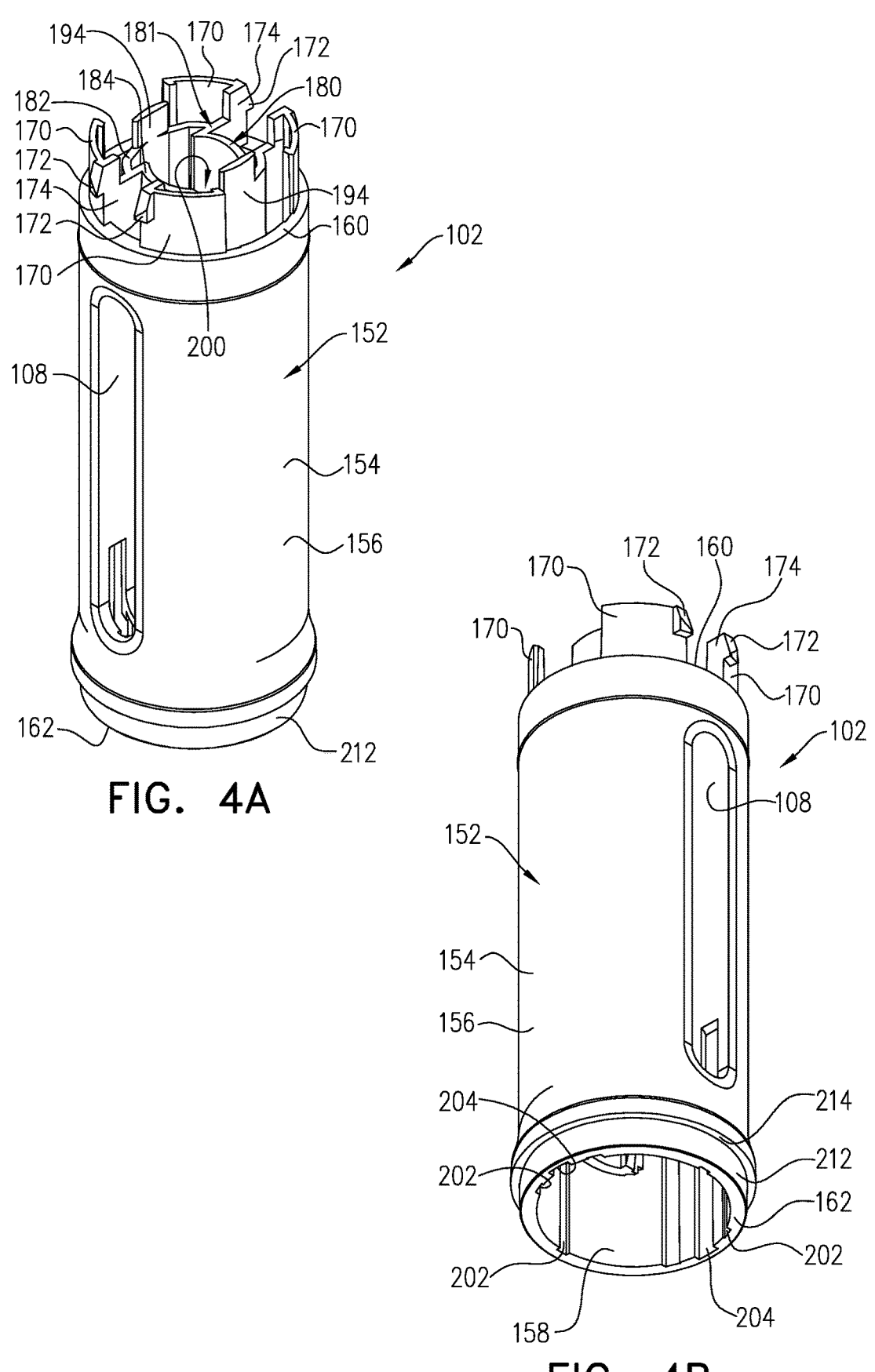
Figure 4G:
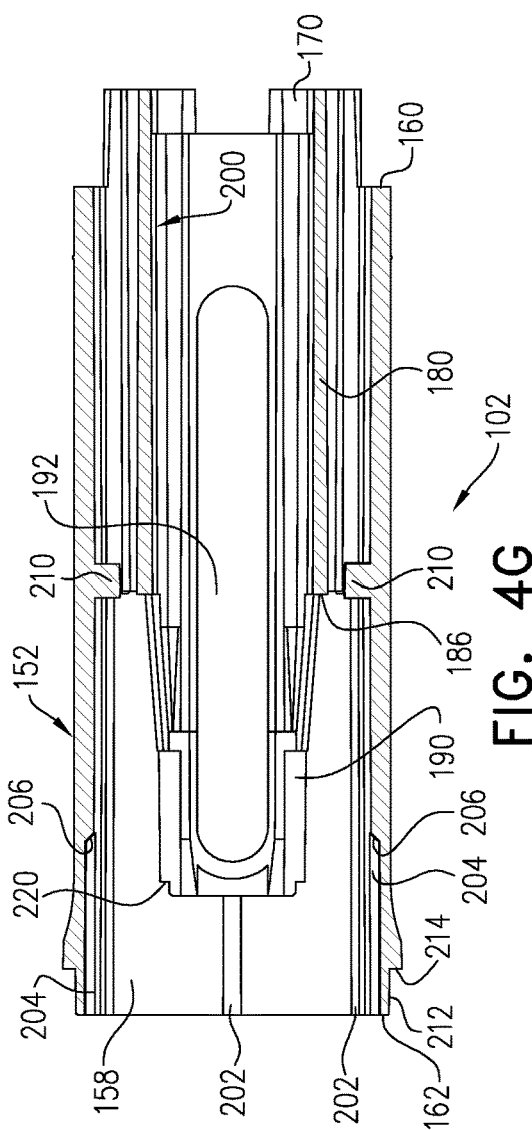
Figure 4H:
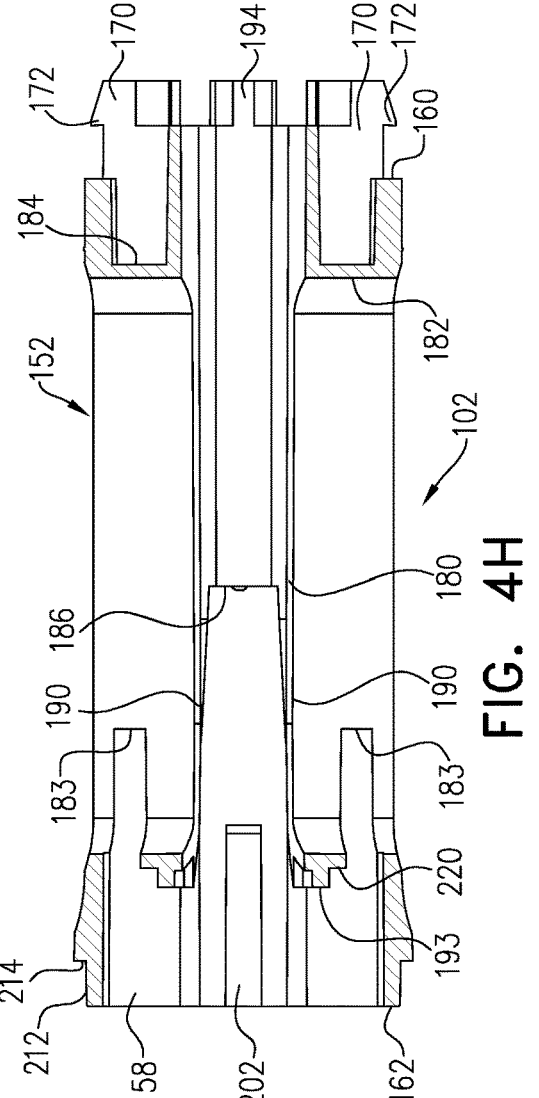
Figure 4F:
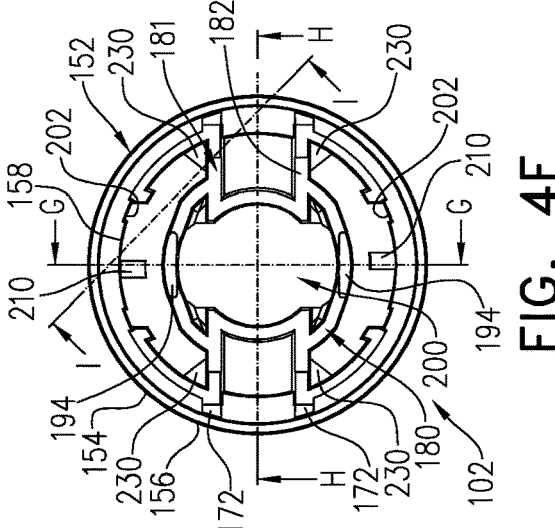

It is particularly seen in FIGS. 4E-4G that a radially inwardly directed protrusion 210 is formed on the inner surface 158 of cylindrical portion 152 and is preferably disposed adjacent forwardly facing end edge 186 of syringe containing portion 180.

A generally circumferential recess 212 is formed on the outer surface 156 of the cylindrical portion 152 and defines a forwardly facing shoulder 214 adapted for engagement with a corresponding surface of the rear housing portion 104, as described in detail hereinbelow.

It is further seen in FIGS. 4E, 4G and 4H that an outwardly radially extending and forwardly facing spring seat 220 is formed on an outer surface of each of the arms 190, configured for supporting the needle guard spring 118.

Figure 4I:
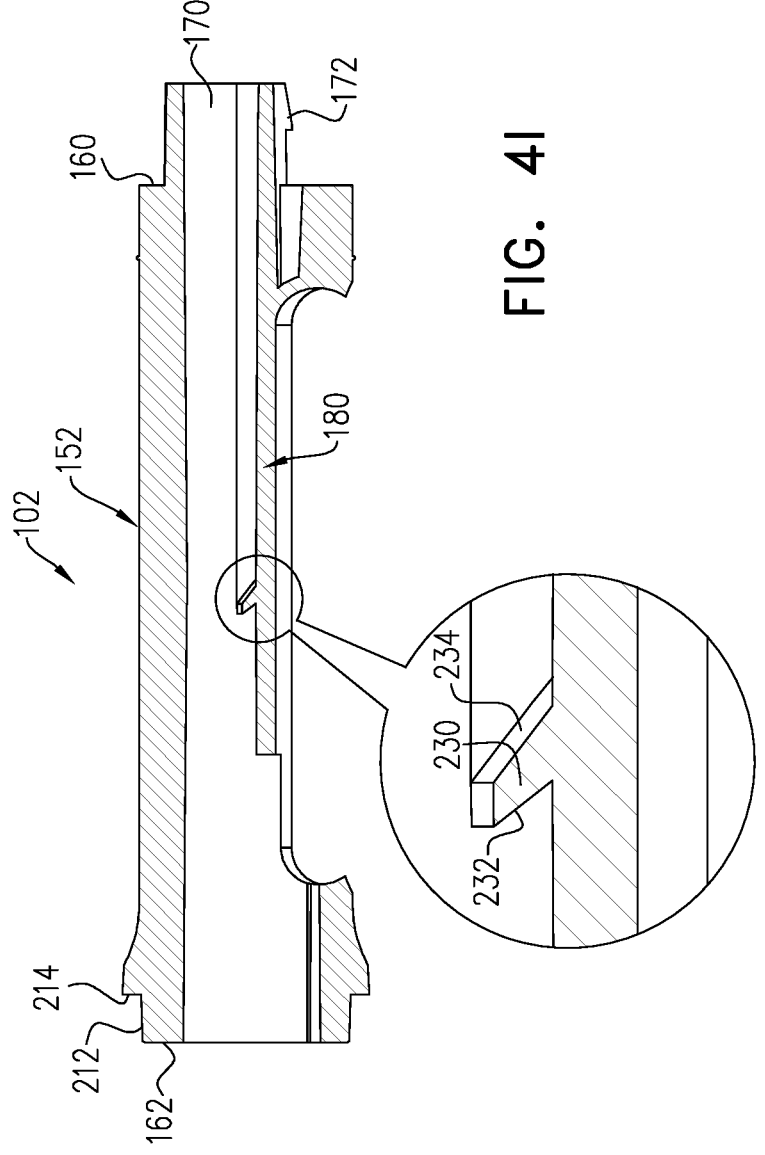

It is specifically seen in FIGS. 4F and 4I that an inwardly directed and forwardly extending tapered protrusion 230 is formed on the inner surface 158 of the cylindrical portion 152 and disposed between cylindrical portion 152 and syringe containing portion 180, generally in an intermediate location along the length of the front housing portion 102. The forwardly extending tapered protrusion 230 defines a forwardly facing tapered surface 232 and a rearwardly facing tapered surface 234.

Figures 5A, 5B:
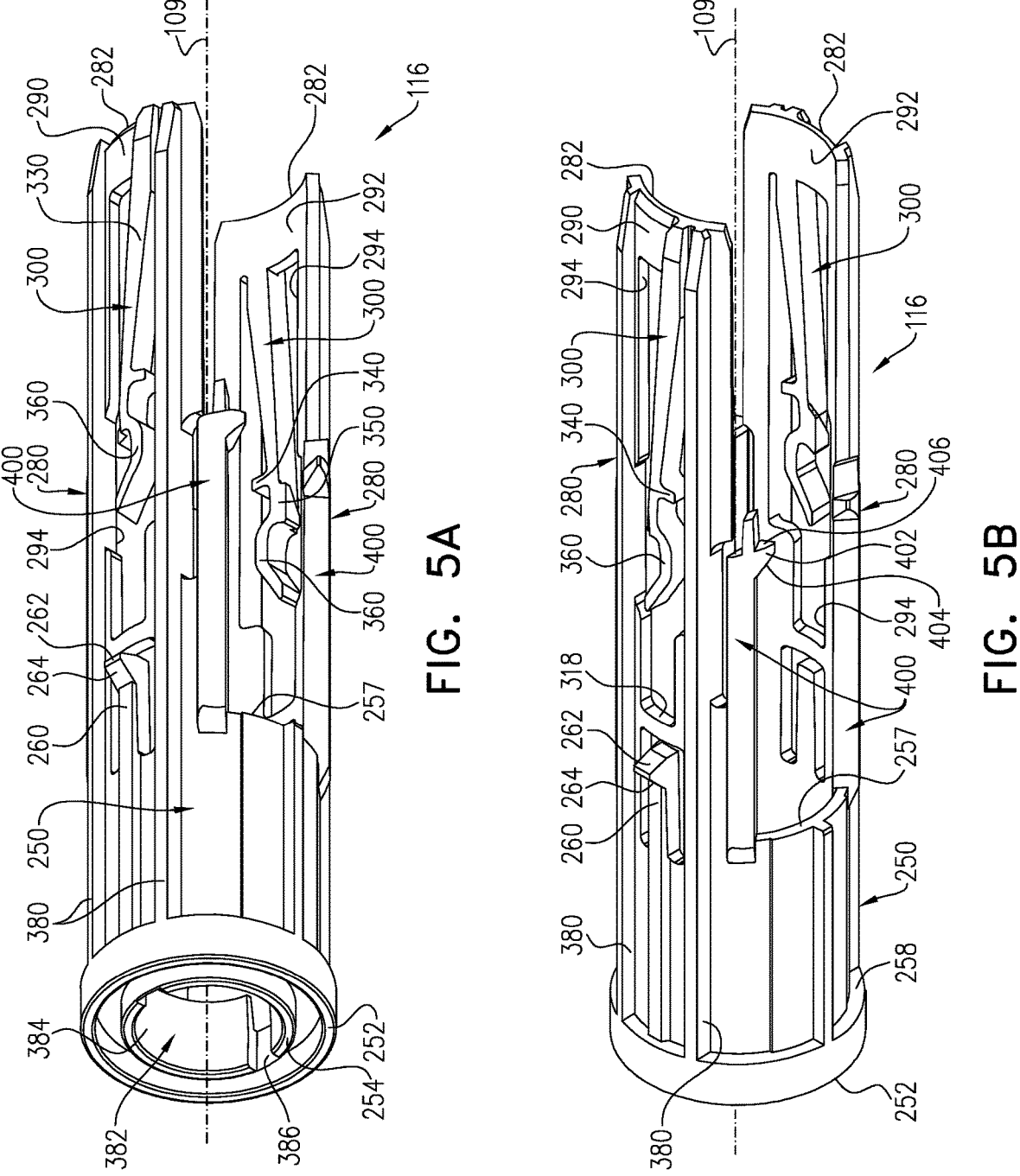
FIGS. 5A, 5B, 5C, 5D, 5E, 5F, 5G, 5H, 5I & 5J are respectively a simplified perspective view of a forward-facing portion, a simplified perspective view of a rearward-facing portion, a simplified first side plan view, a simplified second side plan view, a simplified bottom plan view, a simplified top plan view, a simplified third side plan view, a simplified fourth side view and two sectional views taken along lines I-I in FIG. 5H and lines J-J in FIG. 5C respectively of a needle guard element forming part of the front sub-assembly of the automatic injection device of FIGS. 1A and 1B.
Figures 5C, 5D, 5E:
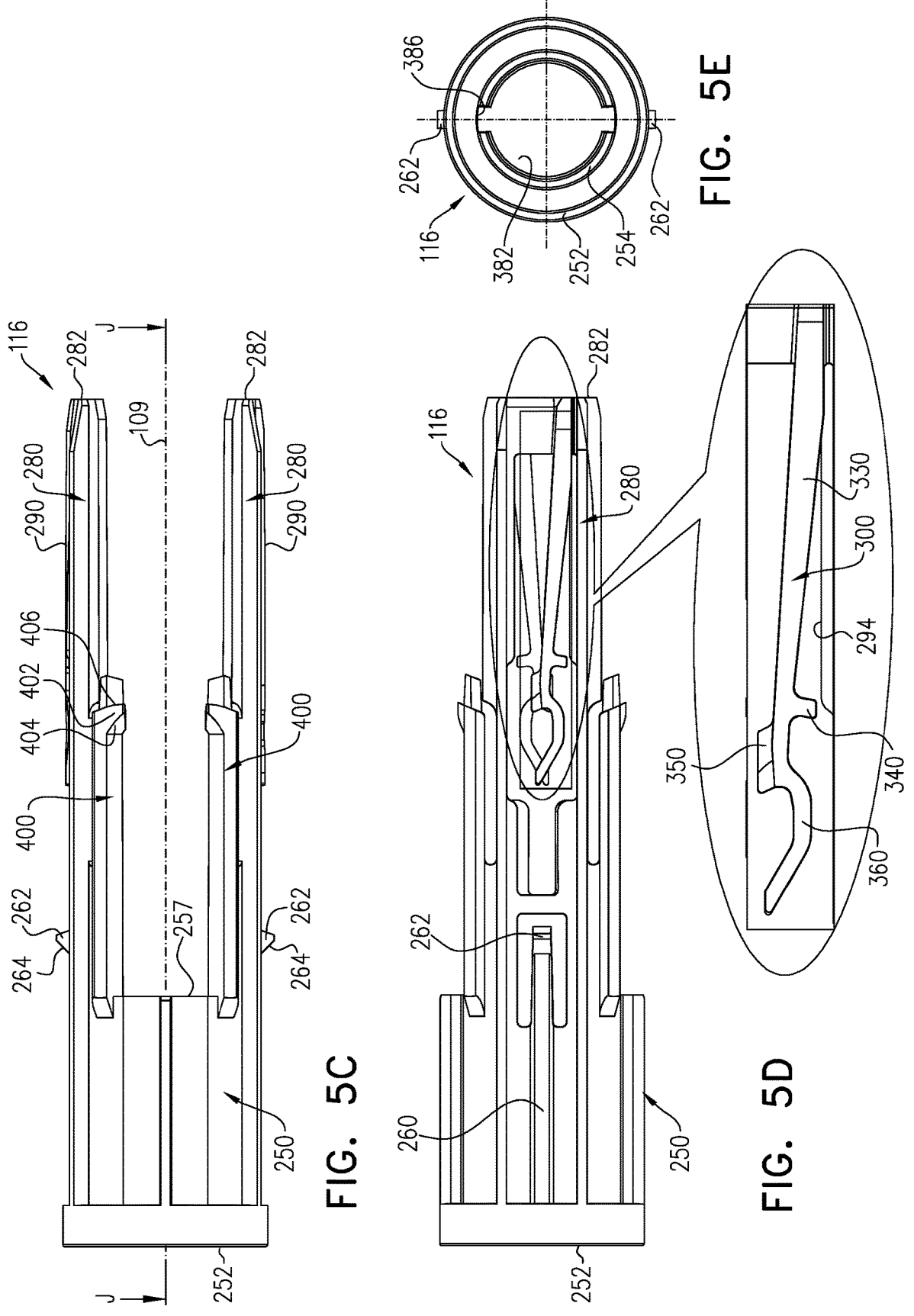
Figures 5F, 5G:
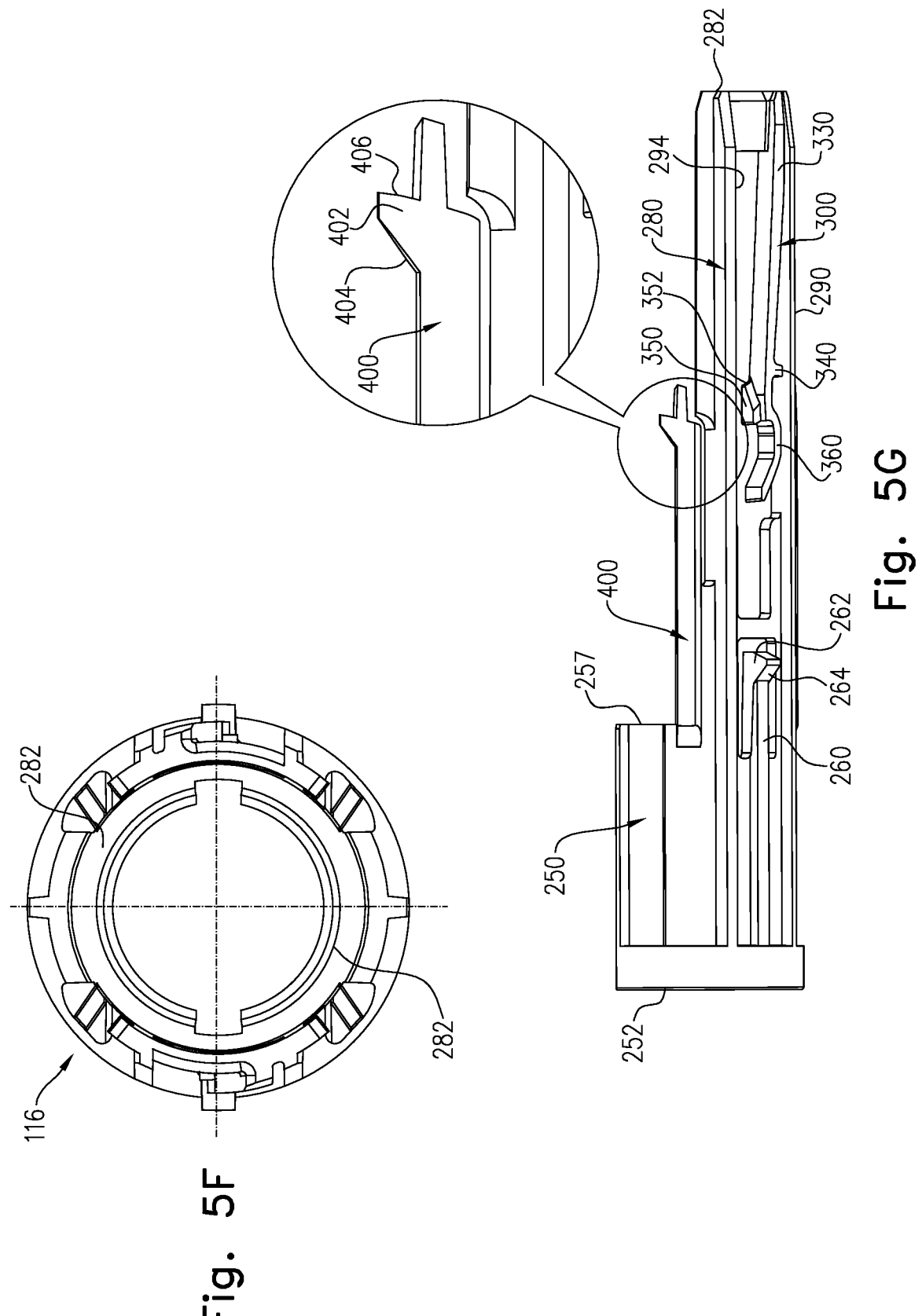
Figure 5H:
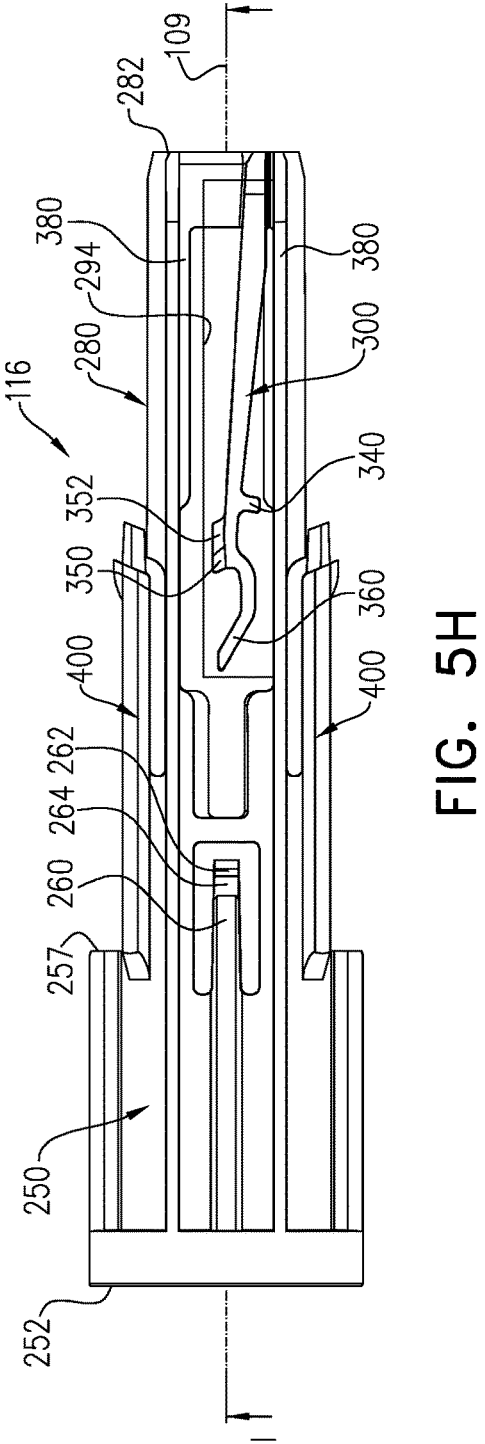
Figure 5I:
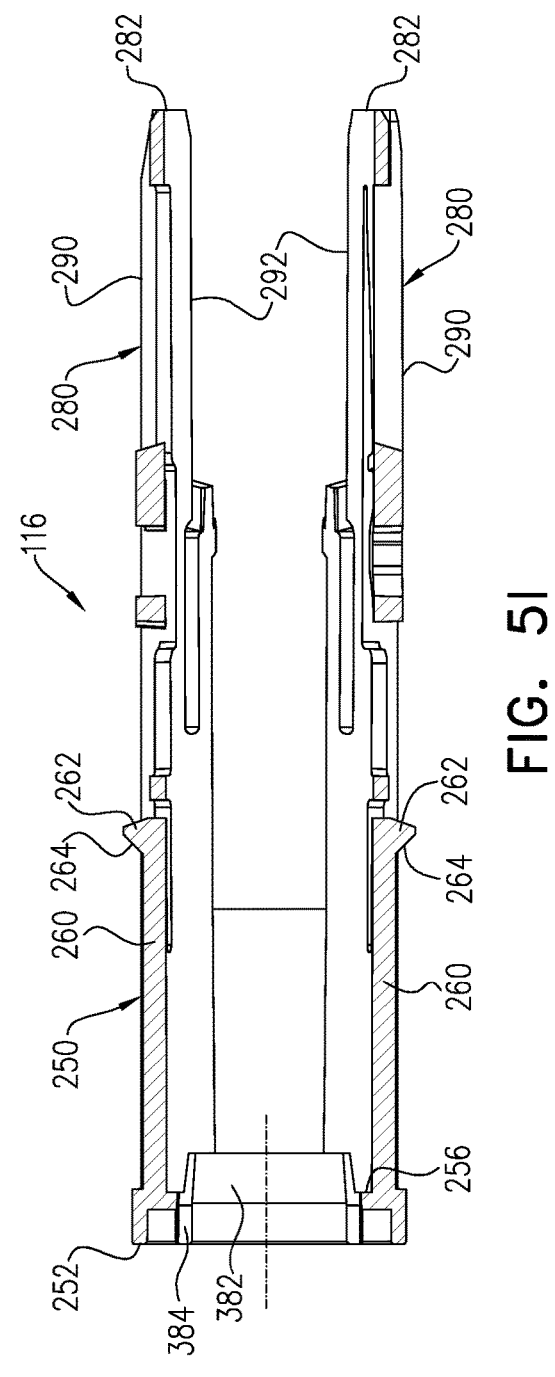

Reference is now made to FIGS. 5A, 5B, 5C, 5D, 5E, 5F, 5G, 5H, 5I & 5J, which are respectively a simplified perspective view of a forward-facing portion, a simplified perspective view of a rearward-facing portion, a simplified first side plan view, a simplified second side plan view, a simplified bottom plan view, a simplified top plan view, a simplified third side plan view, a simplified fourth side view and two sectional views taken along lines I-I in FIG. 5H and lines J-J in FIG. 5C respectively of the needle guard element 116 forming part of the front sub-assembly 150 of the automatic injection device 100 of FIGS. 1A and 1B.

The needle guard element 116 preferably is an integrally formed element, preferably injection molded of plastic and is arranged along longitudinal axis of symmetry 109.

The needle guard element 116 preferably has a generally cylindrical configuration including a generally tubular portion 250, having a forward-facing body engaging surface 252 including a generally annular ribbed protrusion 254. A generally annular internal surface 256, located opposite from body engaging surface 252, forms a spring-seat for needle guard spring 118. The tubular portion 250 terminates at a rearwardly facing surface 257.

A rearwardly facing circumferential shoulder 258 is formed on tubular portion 250 and is slightly axially rearwardly spaced from body engaging surface 252.

Typically, a pair of diametrically opposed snap portions 260 is formed on tubular portion 250. Each of the snap portions 260 has an outwardly protruding finger 262, having a rearwardly tapered surface 264, which finger 262 is selectively inwardly deflectable. It is noted that the snap portions 260 are configured for operative engagement with the front housing portion 102.

Needle guard element 116 has a pair of side-to-side symmetric mounting arms 280 having rearwardmost ends 282, arranged symmetrically about a longitudinal axis 109. Arms 280 extend along and rearwardly of tubular portion 250 parallel to longitudinal axis 109.

Each of arms 280 defines an outer surface 290 and an inner surface 292. A guiding window 294 is formed on each of arms 280 and a labyrinth protrusion 300 extends at least partially through window 294. The labyrinth protrusion 300 preferably extends forwardly from rearward end 282.

Figure 5J:
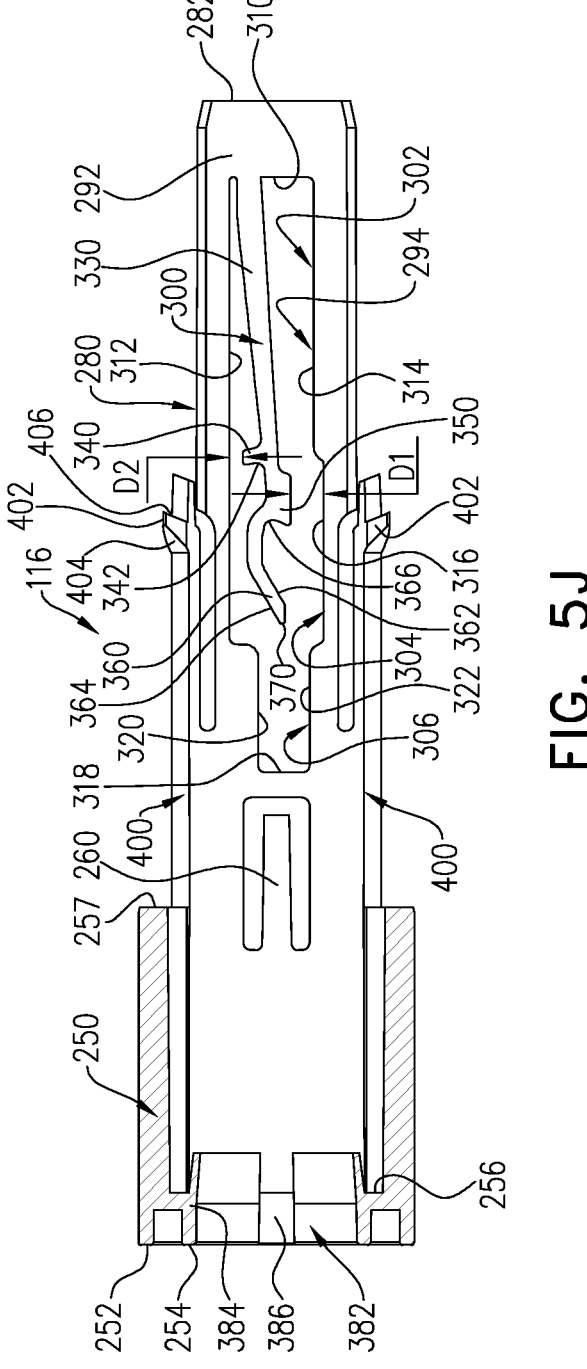

It is specifically seen in FIGS. 5D, 5H and 5J that the guiding window 294 has a rearward longitudinal portion 302 having a first width, a second longitudinal portion 304 having a second width, preferably greater than the first width and a third longitudinal portion 306 having a third width, which is smaller than both the first width and the second width.

The first longitudinal portion 302 is defined by a rearward edge 310, a first side edge 312 and a second side edge 314, whereas the first width is defined between the first side edge 312 and the second side edge 314.

The second longitudinal portion 304 is defined by the first side edge 312 and a second side edge 316, whereas the second width is defined between the first side edge 312 and the second side edge 316.

The third longitudinal portion 306 is defined by a forward edge 318, a first side edge 320 and a second side edge 322, whereas the third width is defined between the first side edge 320 and the second side edge 322.

It is a particular feature of an embodiment of the present invention that at least the third longitudinal portion 306 and the second longitudinal portion 304 serve as a guiding track for a corresponding protrusion of the front housing portion 102.

It is a further particular feature of an embodiment of the present invention that the labyrinth protrusion 300 is preferably resilient due to its structure and is adapted to be deflected laterally between the first side edge 312 and the second side edge 316 of the directing window 294 upon application of force thereon by a corresponding protrusion of a front housing portion 102, as described in detail hereinbelow.

It is specifically seen that the labyrinth protrusion 300 has a longitudinal rearward portion 330 extending forwardly from rearward edge 310 of window 294. The longitudinal rearward portion 330 is preferably slightly curved, such that at its rearward end it is closer to first side edge 312 and at its forward end it is farther away from the first side edge 312.

A laterally outwardly extending first hook 340 is formed at the forward end of the rearward portion 330 and extends towards first side edge 312 and defines a forwardly facing retaining portion 342, which faces the first side edge 312. Disposed forwardly from first hook 340 is a laterally outwardly extending second protrusion 350, which extends at an opposite lateral direction with respect to the first hook 340 and faces the second side edge 316 of window 294. The second protrusion 350 has a rearwardly tapered outwardly directed edge 352. A third curved hook extension 360 extends generally forwardly from second protrusion 350. The third curved hook extension 360 has a concave surface 362 facing the second side edge 316 and a convex surface 364 facing the first side edge 312. A second retaining portion 366 is formed between the second protrusion 350 and the hook extension 360, the second retaining portion 366 faces the second side edge 316. The hook extension 360 defines a forwardmost directing tip 370.

It is noted that at rest, when no force is applied on the labyrinth protrusion 300, a distance D1 is defined between the second protrusion 350 and the second side edge 316 and a distance D2 is defined between the first hook 340 and the first side edge 312.

It is further seen in FIGS. 5A & 5B that a plurality of longitudinal reinforcement ribs 380 are formed along mounting arms 280 and extend preferably from rearwardmost ends 282 to rearwardly facing shoulder 258. The ribs 380 are adapted for engagement with a corresponding surface of the front housing portion 102.

A generally circular opening 382 is formed in body engaging surface 252 and extends axially rearwardly therefrom. A generally circular protrusion 384 extends rearwardly from protrusion 254 and is adapted to bound opening 382. Typically, two diametrically opposed longitudinal notches 386 are formed through the circular protrusion 384 and extend rearwardly from protrusion 254. The notches 386 are adapted for alignment of the needle cover remover 140 upon mounting thereof onto the needle guard element 116.

A rearwardly extending arm 400 is formed adjacent each side of each of the mounting arms 280. Two arms 400 are adapted to bound one mounting arm 280 from each side thereof. Arms 400 preferably extend rearwardly from rearwardly facing surface 257 to a location disposed generally in an intermediate portion along the length of the mounting arm 280. Each of the arms 400 includes an outwardly extending protrusion 402 having a forwardly facing tapered surface 404 and a rearwardly facing surface 406.

Figure 6A:
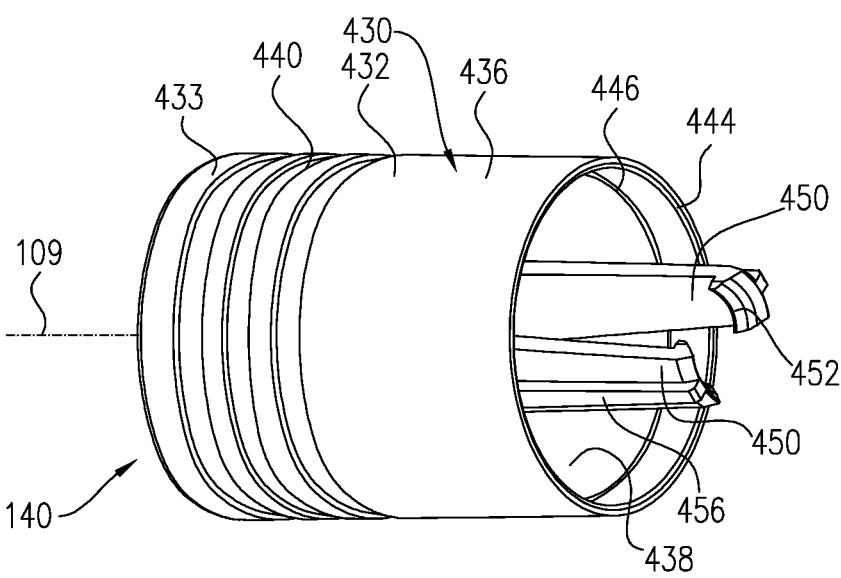
FIGS. 6A, 6B, 6C, 6D, 6E, 6F & 6G are respectively a simplified perspective view of a rearward-facing portion, a simplified perspective view of a forward-facing portion, a simplified side plan view, a simplified top plan view, a simplified bottom plan view and two simplified sectional views taken along lines F-F and G-G in FIG. 6E of a needle shield remover forming part of the front sub-assembly of the automatic injection device of FIGS. 1A and 1B.
Figure 6B:
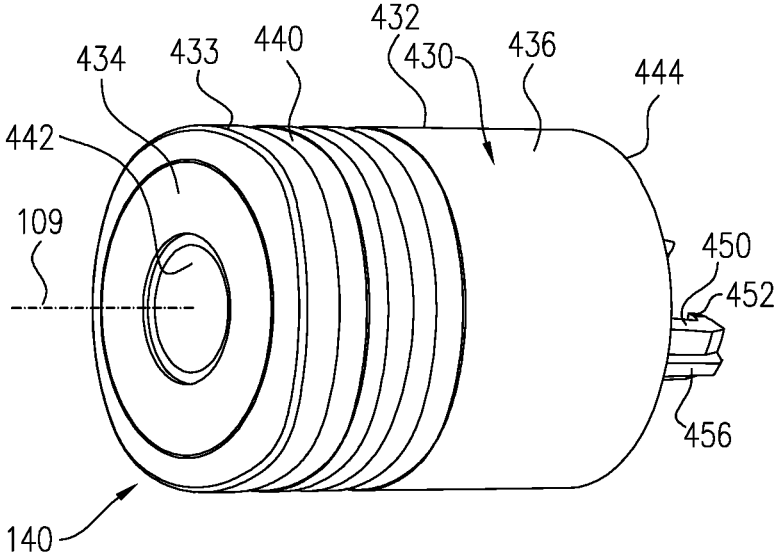
Figure 6C:
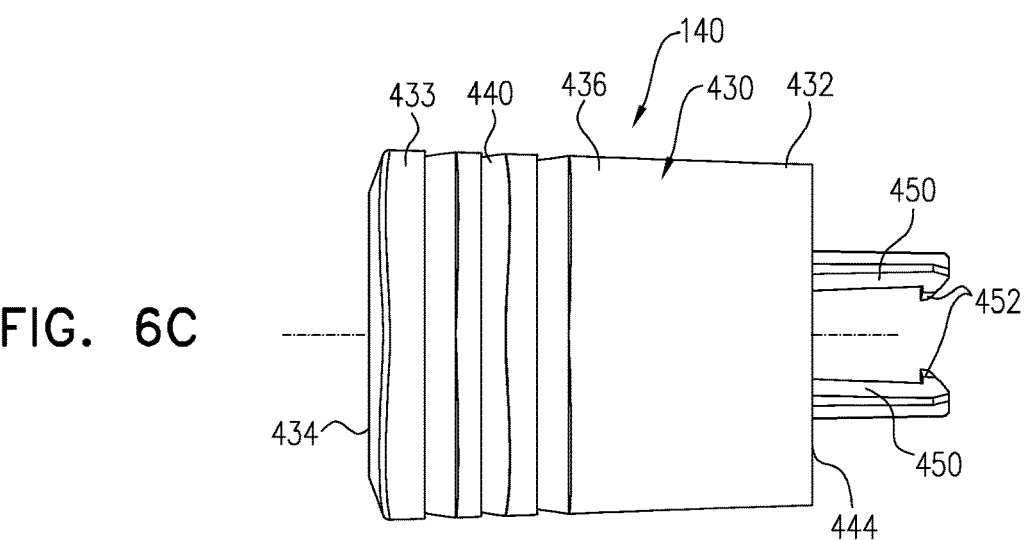
Figure 6D:
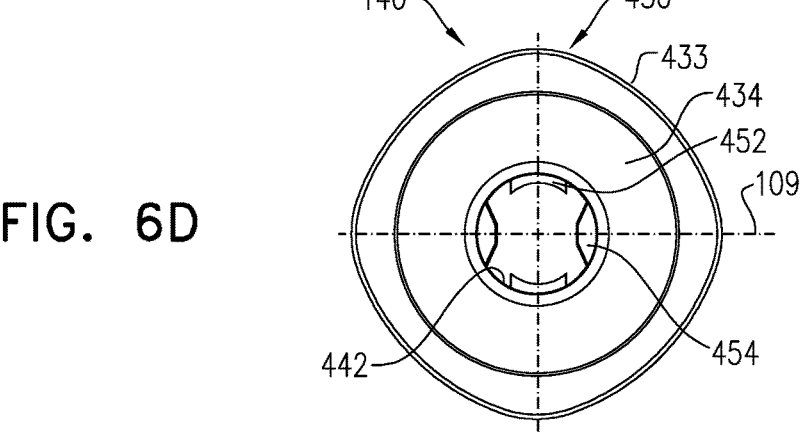
Figure 6E:
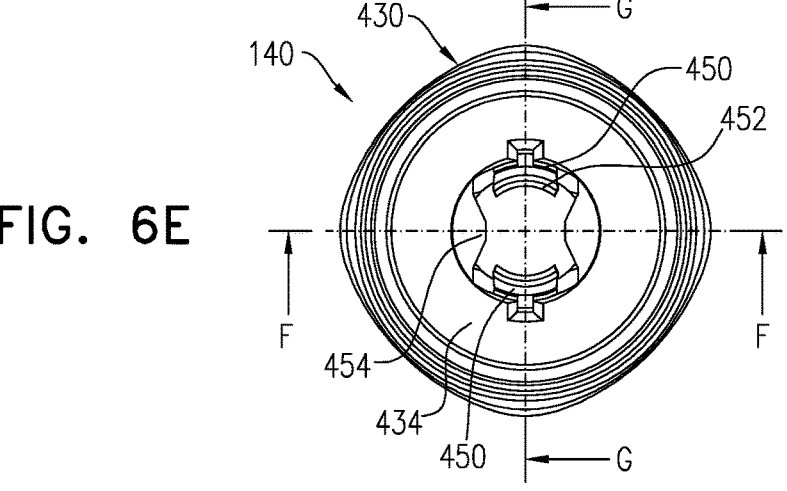
Figure 6F:
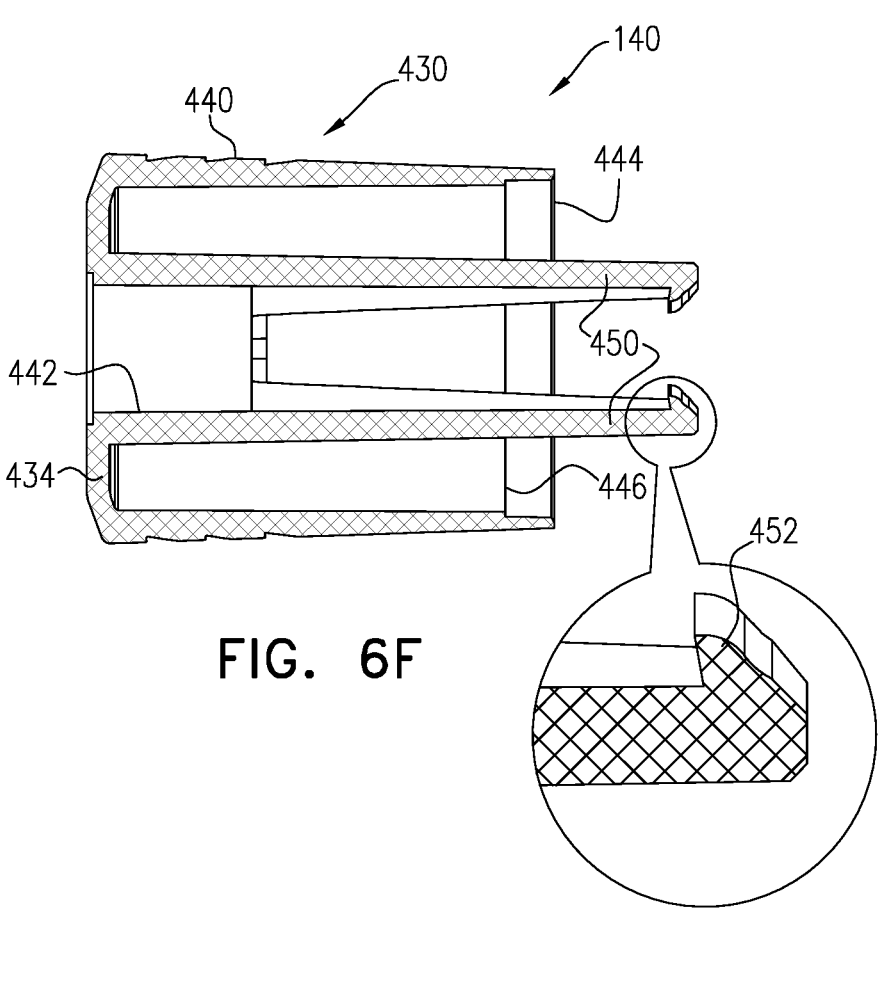
Figure 6G:
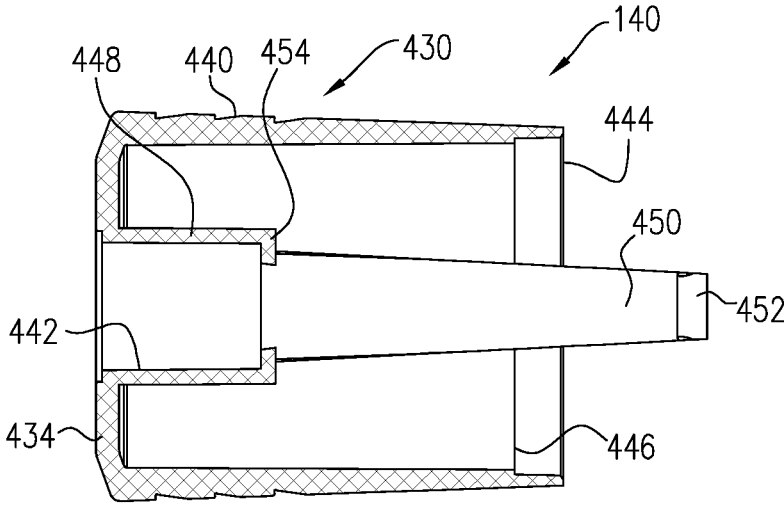

Reference is now made to FIGS. 6A, 6B, 6C, 6D, 6E, 6F & 6G are respectively a simplified perspective view of a rearward-facing portion, a simplified perspective view of a forward-facing portion, a simplified side plan view, a simplified top plan view, a simplified bottom plan view and two simplified sectional views taken along lines F-F and G-G in FIG. 6E of the needle shield remover 140 forming part of the front sub-assembly 150 of the automatic injection device 100 of FIGS. 1A and 1B.

The needle shield remover 140 preferably is an integrally formed element, preferably injection molded of plastic and is arranged along longitudinal axis of symmetry 109.

The needle shield remover 140 preferably includes a generally cylindrical outer portion 430 having a circumferential wall portion 432 with a circular cross-section and a wall portion 433 with a rectangular cross-section and having a closed forward end 434 of a generally rectangular shape. The outer portion 430 has an outer surface 436 and an inner surface 438 and a plurality of gripping surfaces 440 are preferably formed on the outer surface 436 of the outer portion 430.

It is a particular feature of an embodiment of the present invention that the outer portion 430 has a wall portion with a preferably circular cross-section and another wall portion with a preferably rectangular cross-section, such that inadvertent rolling of the needle cover remover 140 is prevented.

An opening 442 is formed through the forward end 434. Wall portion 432 defines a generally circular rearward edge 444. A rearwardly facing shoulder 446 is formed forwardly of rearward edge 444.

A cylindrical portion 448 extends rearwardly from forward end 434 and generally, two mutually facing gripping arms 450 extend longitudinally rearwardly from the forward end of cylindrical portion 448 and extend rearwardly of rearward edge 444. Each of the gripping arms 450 has an inwardly extending gripping tooth 452 disposed adjacent the rearward end of the arms 450. Inwardly extending protrusions 454 extend from the rearward end of the cylindrical portion 448, the protrusions 454 preferably extend transversely with respect to longitudinal axis 109, and adapted to prevent the needle cover from falling out of the needle cover remover 140 through opening 442. Outer longitudinal ribs 456 are formed on the outer surface of the gripping arms 450.

Figure 7:
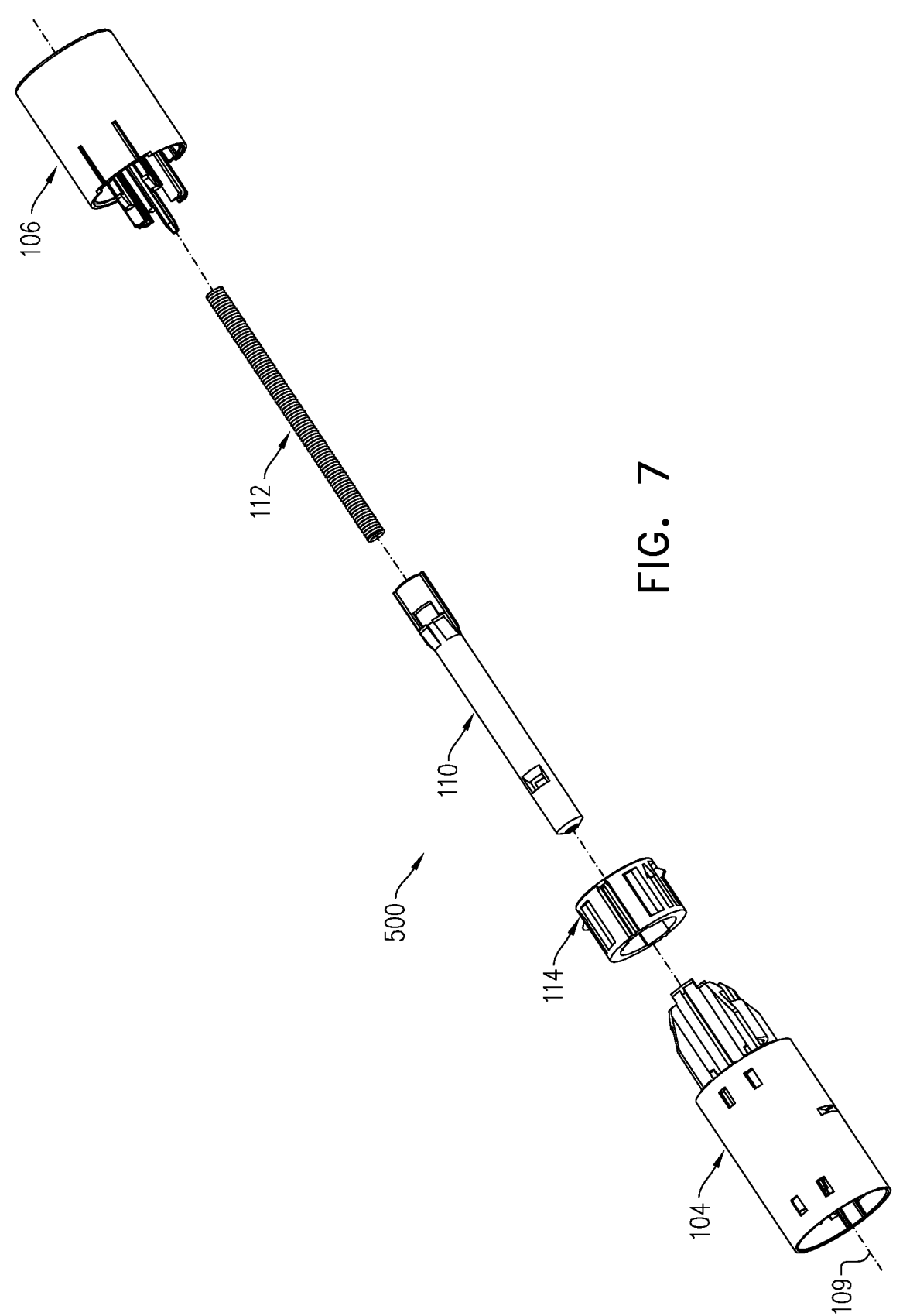
FIG. 7 is a simplified exploded view of a rear sub-assembly of the automatic injection device of FIGS. 1A and 1B.
Figure 8A:
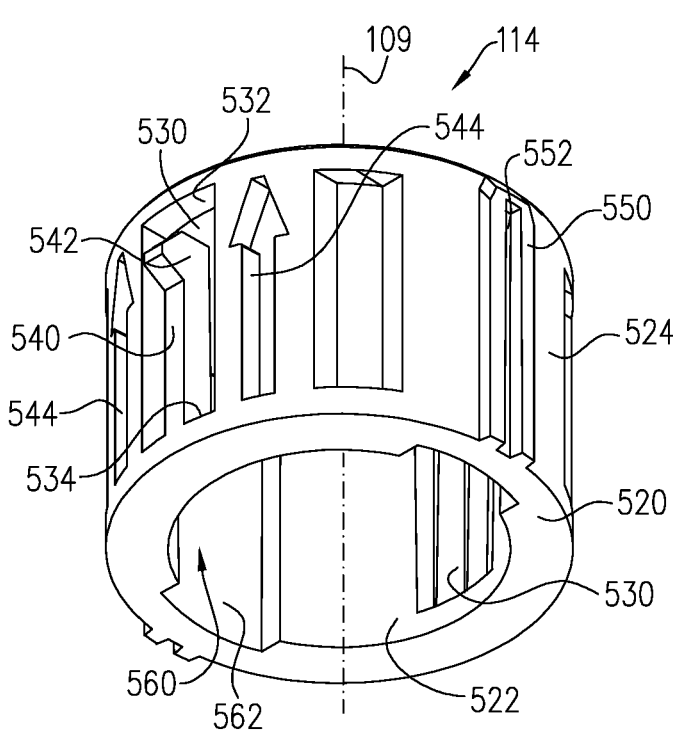
FIGS. 8A, 8B, 8C, 8D, 8E, 8F, 8G & 8H are respectively a simplified perspective view of a forward-facing portion, a simplified perspective view of a rearward-facing portion, two simplified side plan views, a simplified top plan view, a simplified bottom plan view and two simplified sectional views taken along lines G-G and H-H in FIG. 8F of a trigger ring forming part of the rear sub-assembly of the automatic injection device of FIGS. 1A and 1B.
Figure 8B:
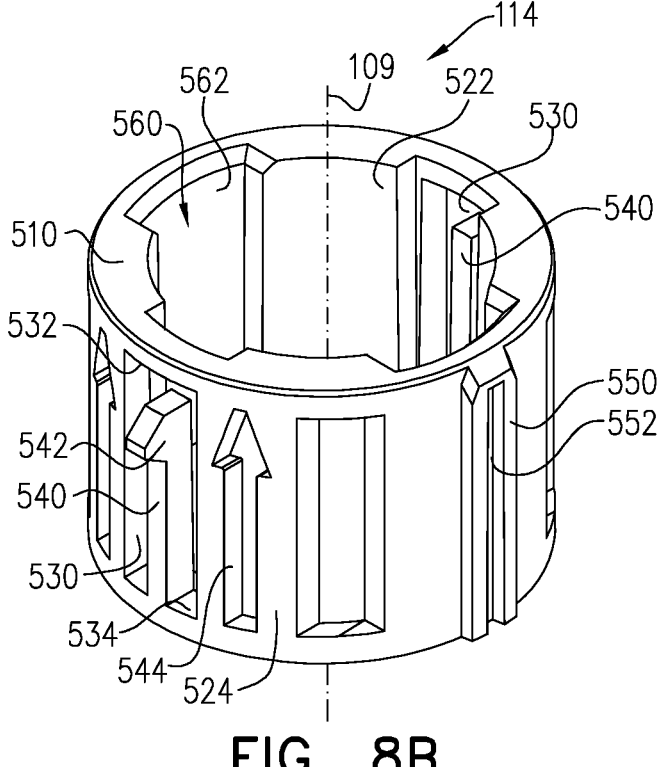
Figure 8C:
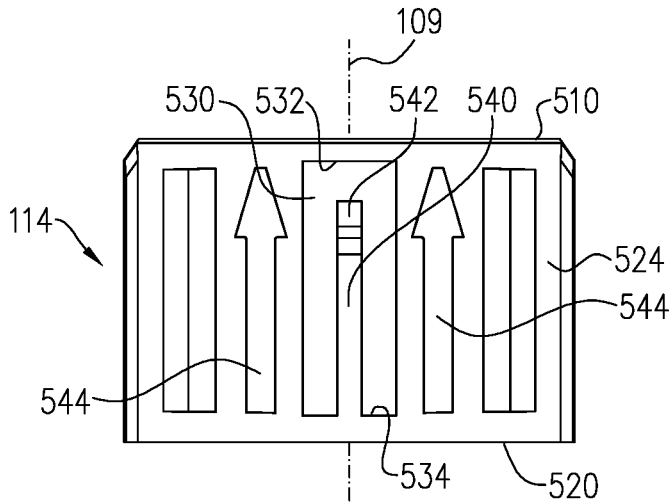
Figure 8D:
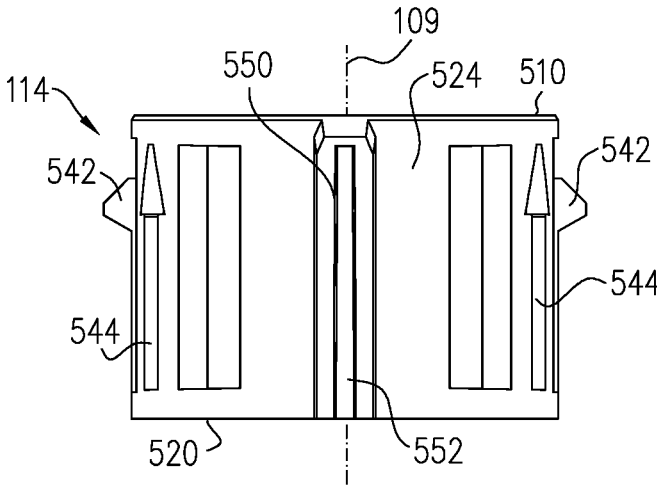
Figure 8E:
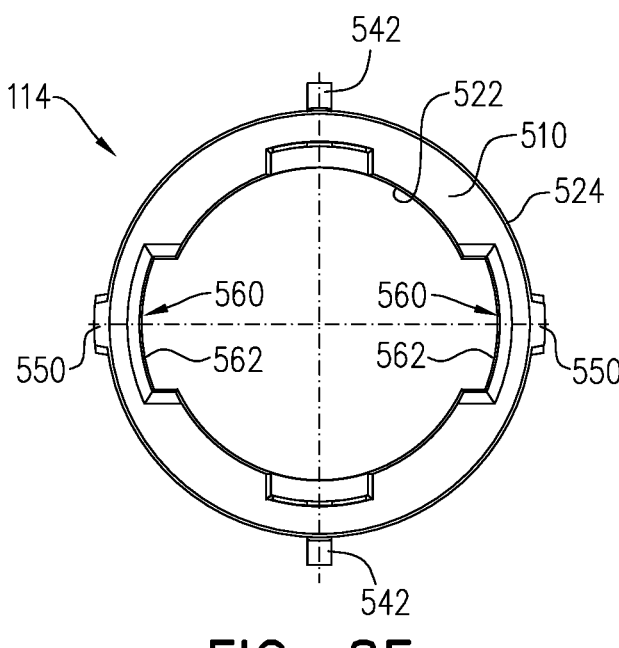
Figure 8F:
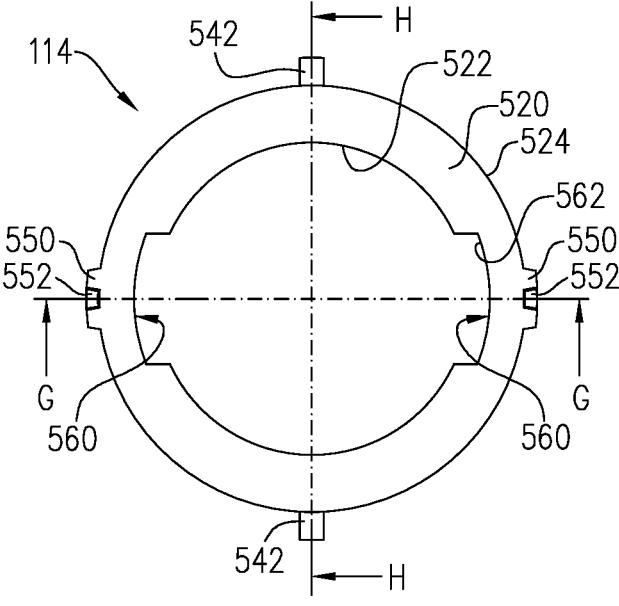
Figure 8G:
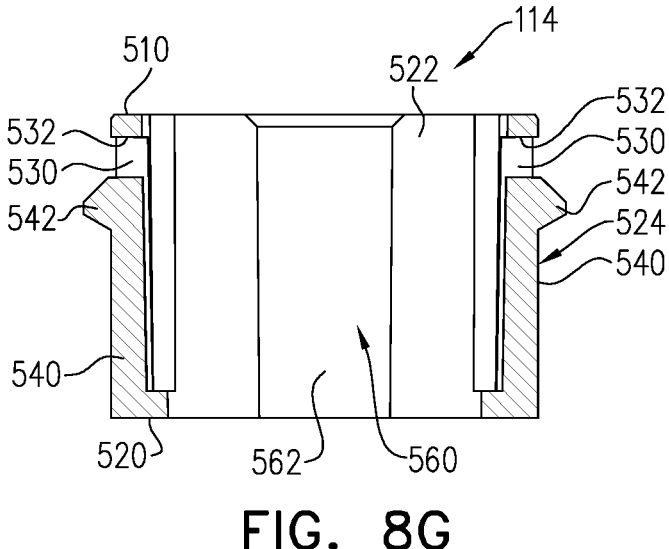
Figure 8H:
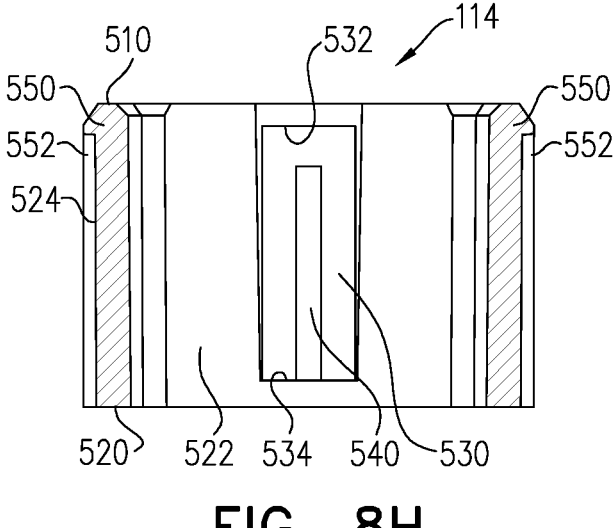

Reference is now made to FIG. 7, which is a simplified exploded view of a rear sub-assembly 500 of the automatic injection device 100 of FIGS. 1A and 1B. Reference is additionally made to FIGS. 8A, 8B, 8C, 8D, 8E, 8F, 8G & 8H, which are respectively a simplified perspective view of a forward-facing portion, a simplified perspective view of a rearward-facing portion, two simplified side plan views, a simplified top plan view, a simplified bottom plan view and two simplified sectional views taken along lines G-G and H-H in FIG. 8E of the trigger ring 114 forming part of the rear sub-assembly 500 of the automatic injection device 100 of FIGS. 1A and 1B.

The rear sub-assembly 500 is shown in FIG. 7, which includes trigger ring 114, rear housing portion 104, plunger rod 110, injection spring 112 and rear cover 106, which are all mutually arranged along longitudinal axis 109.

Referring now specifically to FIGS. 8A-8H, the trigger ring 114 preferably is an integrally formed element, preferably injection molded of plastic and is arranged along longitudinal axis of symmetry 109.

The trigger ring 114 preferably has a circular cross-section and defines a rearward end surface 510 and a forward triggering surface 520.

It is seen in FIGS. 8A-8H that the trigger ring 114 defines an inner surface 522 and an outer surface 524. Typically, two longitudinal openings 530 are formed in trigger ring 114 and are disposed generally diametrically opposed to each other. Each of the openings defines a forwardly facing edge 532 and a rearwardly facing edge 534. A generally deflectable arm 540 extends rearwardly from the rearwardly facing edge 534 to a location generally adjacent the forwardly facing edge 532 and having a radially outwardly extending protrusion 542 at the rearward end thereof.

A plurality of arrow-like apertures 544 are formed on the outer surface 524 of the trigger ring 114 to indicate the direction in which the trigger ring 114 should be mounted into the automatic injection device 100 during assembly.

It is also seen in FIGS. 8A-8F that typically two longitudinal guiding ribs 550 are formed on the outer surface 524 of the trigger ring 114 and are generally diametrically opposed with respect to each other. The guiding ribs 550 extend generally from the rearward end surface 510 to the forward triggering surface 520 of the trigger ring 114. A longitudinal slot 552 is formed along each of the guiding ribs 550.

Typically, two locking grooves 560 are formed on the inner surface 522 of the trigger ring 114. The locking grooves 560 are generally diametrically opposed with respect to each other. The locking grooves 560 extend generally from the rearward end surface 510 to the forward trigger surface 520 of the trigger ring 114. The locking grooves 560 are generally radially spaced with respect to deflectable arms 540. The locking grooves 560 define a radially inwardly facing surface 562.

Figure 9A:
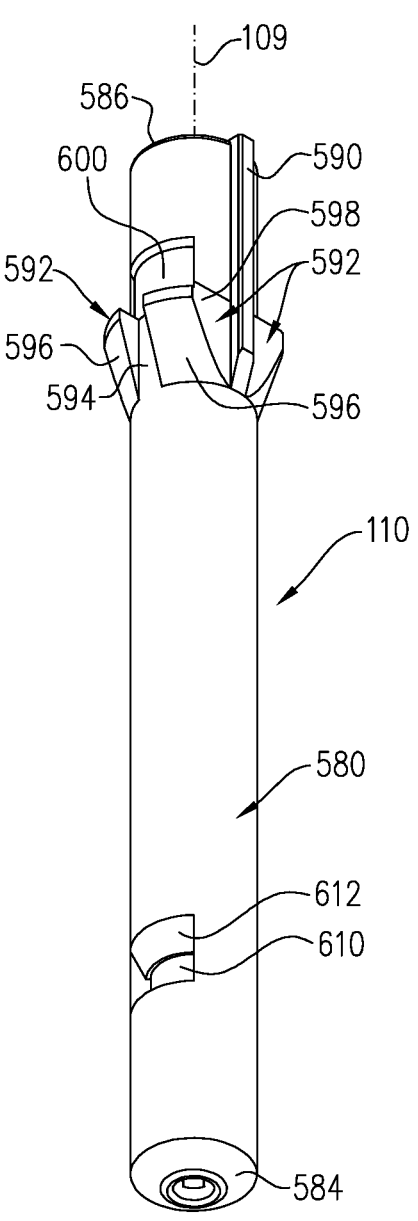
FIGS. 9A, 9B, 9C, 9D, 9E, 9F, 9G & 9H are respectively a simplified perspective view of a forward-facing portion, a simplified perspective view of a rearward-facing portion, two simplified side plan views, a simplified top plan view, a simplified bottom plan view and two simplified sectional views taken along lines G-G and lines H-H in FIG. 9E of a plunger rod element forming part of the rear sub-assembly of the automatic injection device of FIGS. 1A and 1B.
Figure 9B:
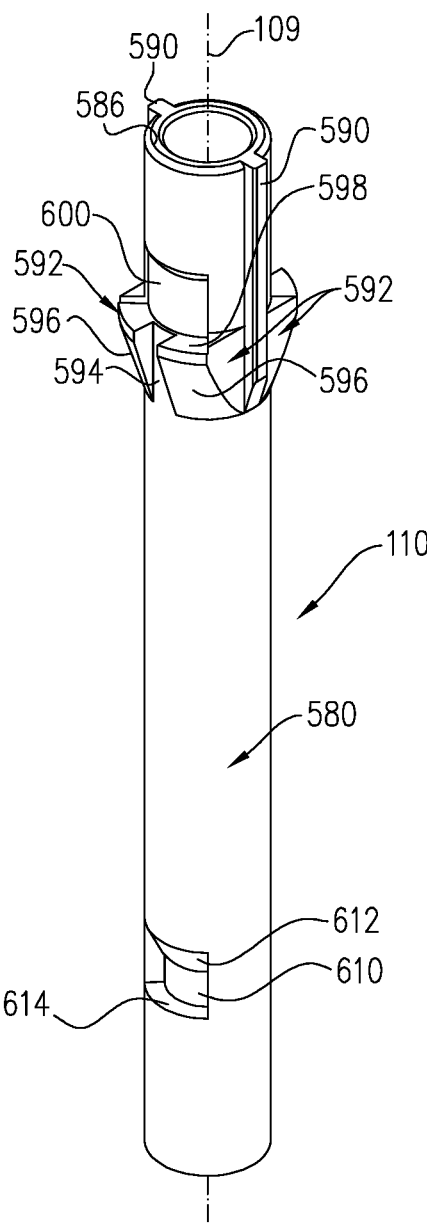
Figure 9C:
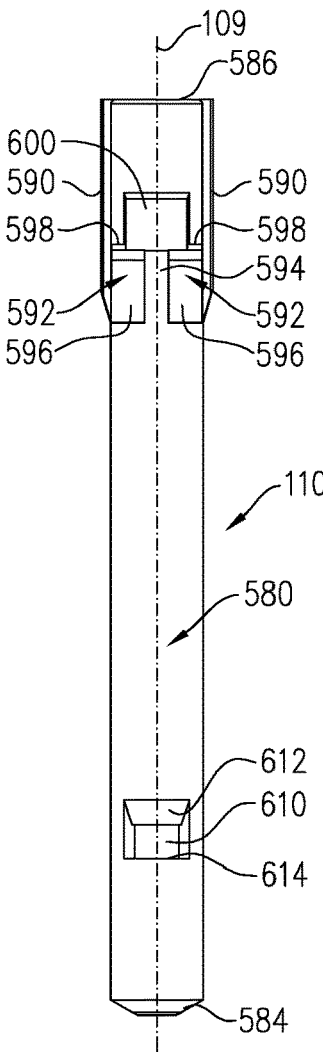
Figure 9D:
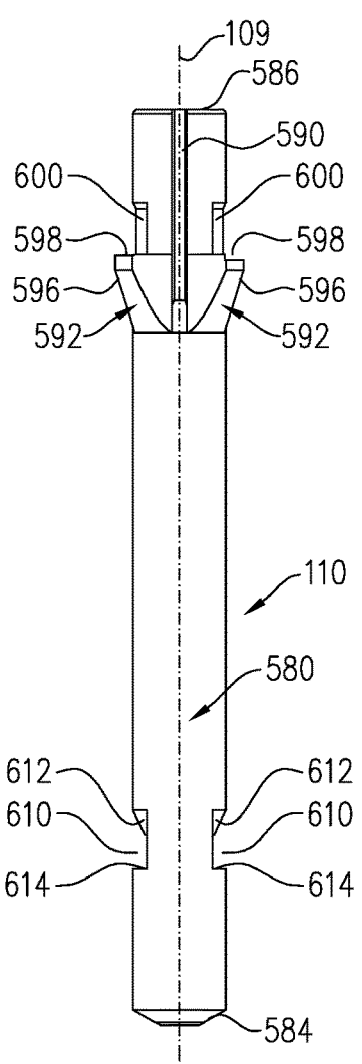
Figure 9E:
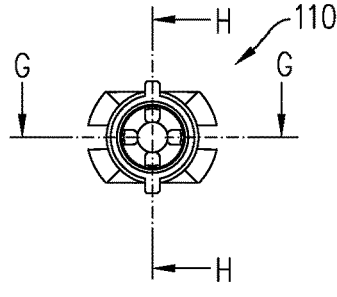
Figure 9F:
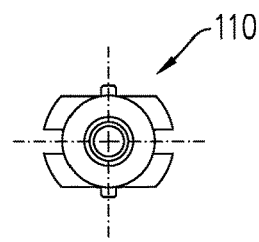

Reference is now made to FIGS. 9A, 9B, 9C, 9D, 9E, 9F, 9G & 9H, which are respectively a simplified perspective view of a forward-facing portion, a simplified perspective view of a rearward-facing portion, two simplified side plan views, a simplified top plan view, a simplified bottom plan view and two simplified sectional views taken along lines G-G and lines H-H in FIG. 9E of the plunger rod element 110 forming part of the rear sub-assembly 500 of the automatic injection device 100 of FIGS. 1A and 1B.

The plunger rod element 110 preferably is an integrally formed element, preferably injection molded of plastic and is arranged along longitudinal axis of symmetry 109.

The plunger rod element 110 preferably includes a generally hollow cylindrical shaft 580 arranged along longitudinal axis 109 and defining an interior bore 582. The cylindrical shaft 580 has a forwardly facing piston engaging wall 584 formed at the forward end thereof, which is generally disposed transversely to longitudinal axis 109 and a rearwardly facing edge 586.

It is seen in FIGS. 9A-9H that the cylindrical shaft 580 has typically two guiding ribs 590 extending longitudinally forwardly from the rearwardly facing edge 586. The guiding ribs 590 are generally diametrically opposed with respect to each other.

Typically, two pairs of radially outwardly extending protrusions 592 are formed on the outer surface of the cylindrical shaft 580. Each pair of protrusions 592 is disposed between two guiding ribs 590 and each protrusion 592 is radially spaced from each other, providing a longitudinal groove 594 therebetween. The outwardly extending protrusions 592 define a forwardly facing tapered surface 596 and a rearwardly facing surface 598, which generally extends transversely with respect to the longitudinal axis 109.

A recess 600 is formed rearwardly of rearwardly facing surfaces 598 of each of pair of protrusions 592.

Typically, two openings 610 are formed adjacent the forward end of the plunger rod element 110. Openings 610 are generally rearwardly spaced from piston engaging surface 584 and are preferably diametrically opposed with respect to each other. The openings 610 generally communicate with bore 582 and define mutually facing forwardly facing tapered surface 612 and rearwardly facing edge 614.

Figures 9G, 9H:
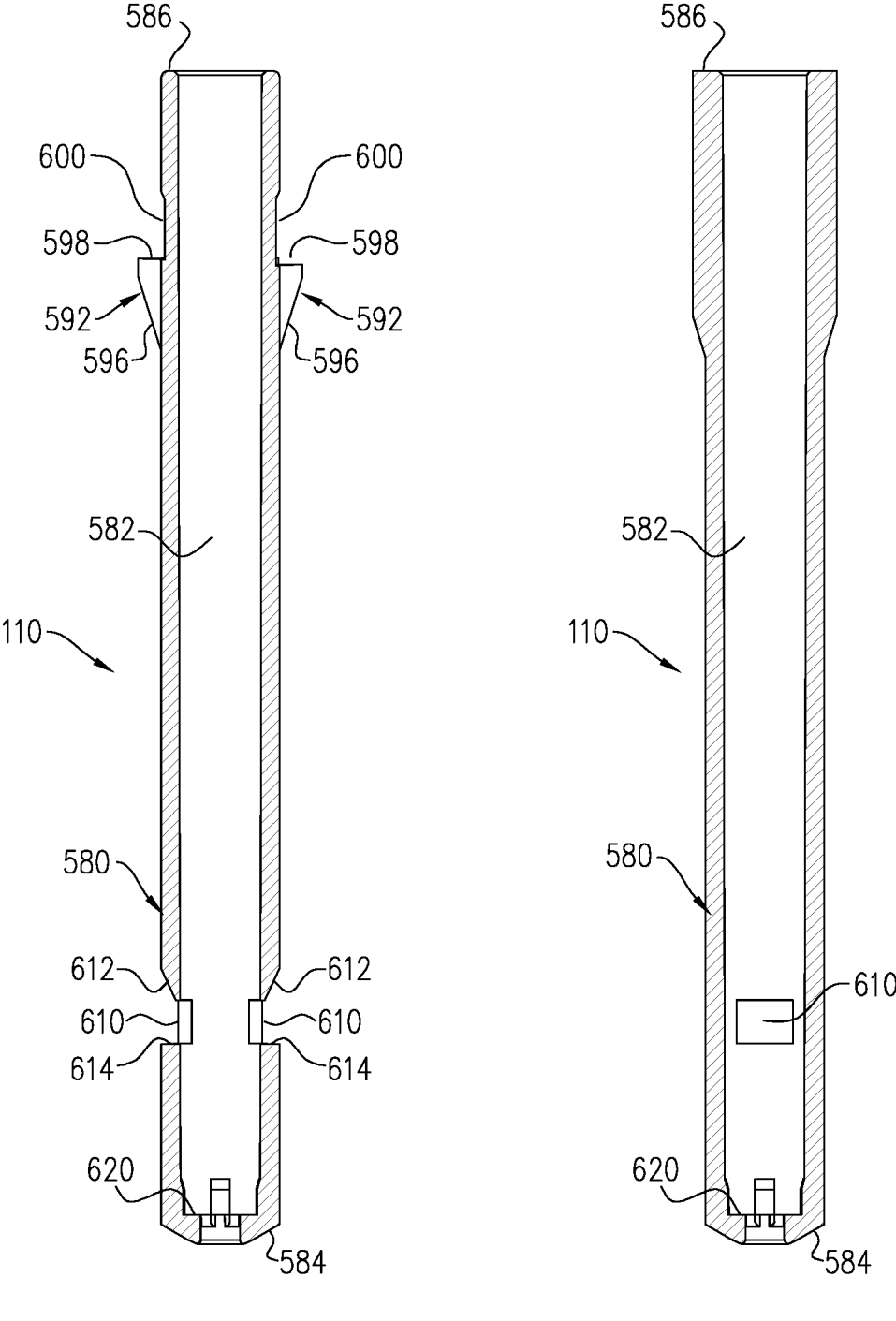

It is specifically seen in FIGS. 9G and 9H that the hollow cylindrical shaft 580 defines longitudinal bore 582 terminating at a rearwardly facing surface 620, serving as a spring seat.

Figure 10B:
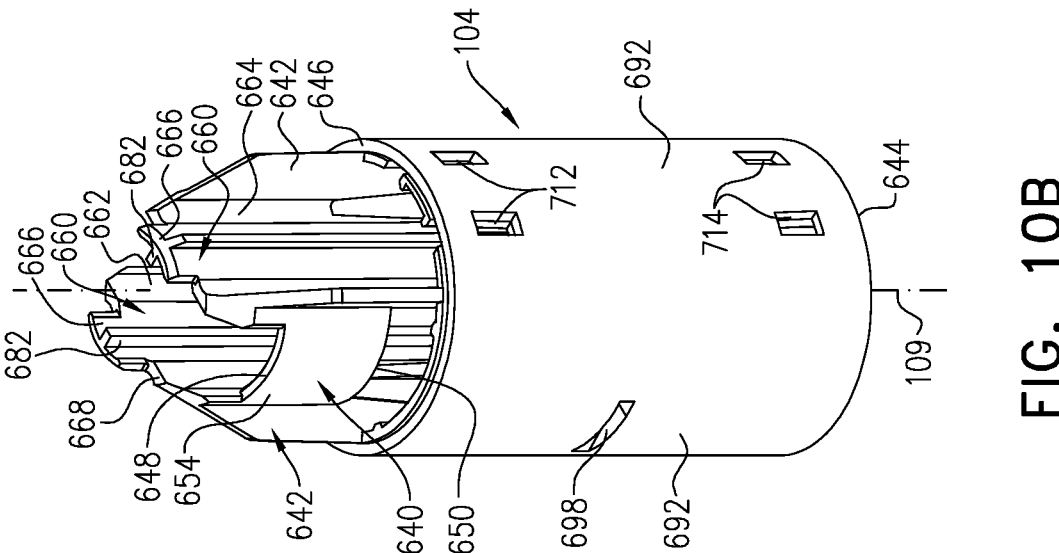
FIGS. 10A, 10B, 10C, 10D, 10E, 10F, 10G & 10H are respectively a simplified perspective view of a forward-facing portion, a simplified perspective view of a rearward-facing portion, two simplified side plan views, a simplified top plan view, a simplified bottom plan view and two simplified sectional views taken along lines G-G and lines H-H in FIG. 10E of a rear housing portion forming part of the rear sub-assembly of the automatic injection device of FIGS. 1A and 1B.
Figure 10A:
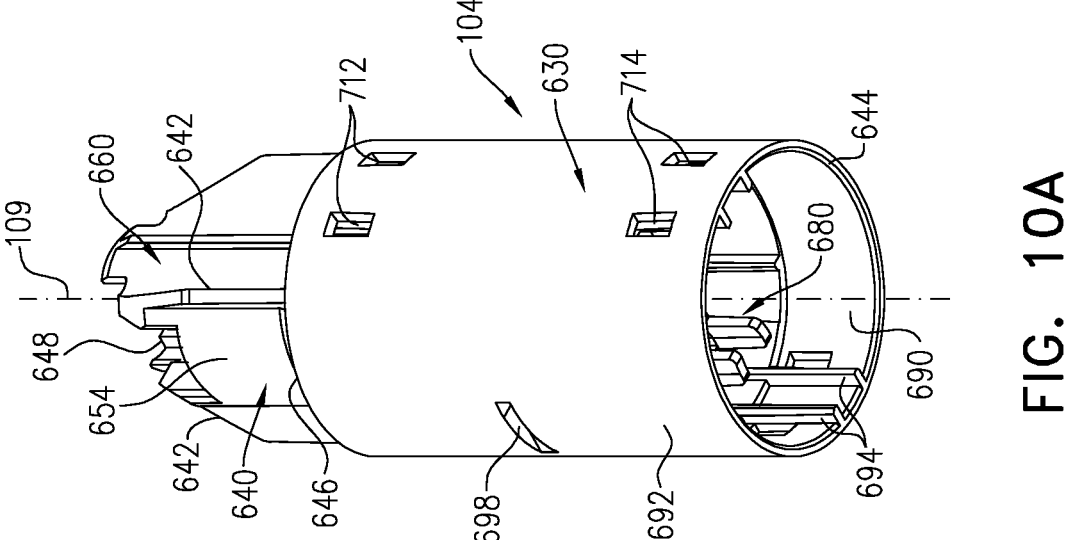
Figure 10D:
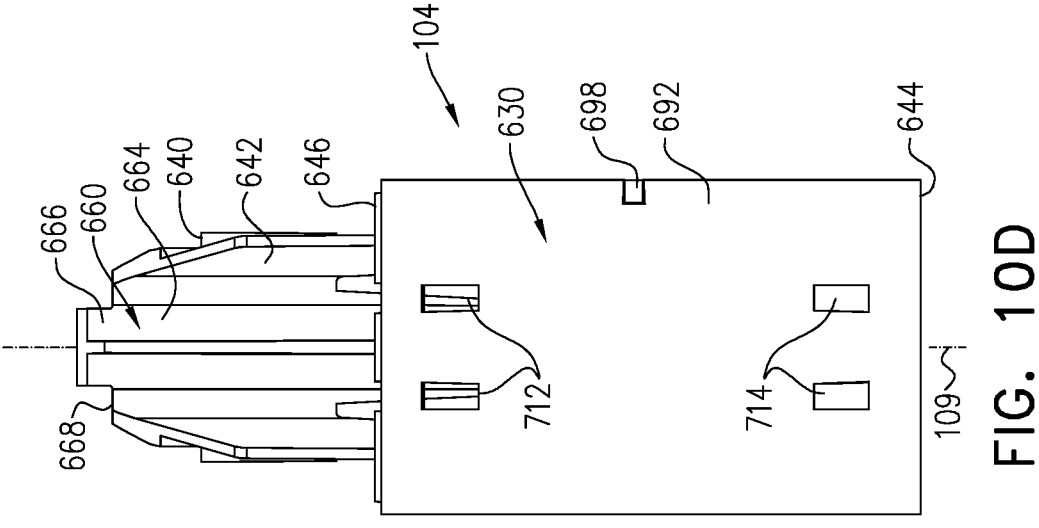
Figure 10C:
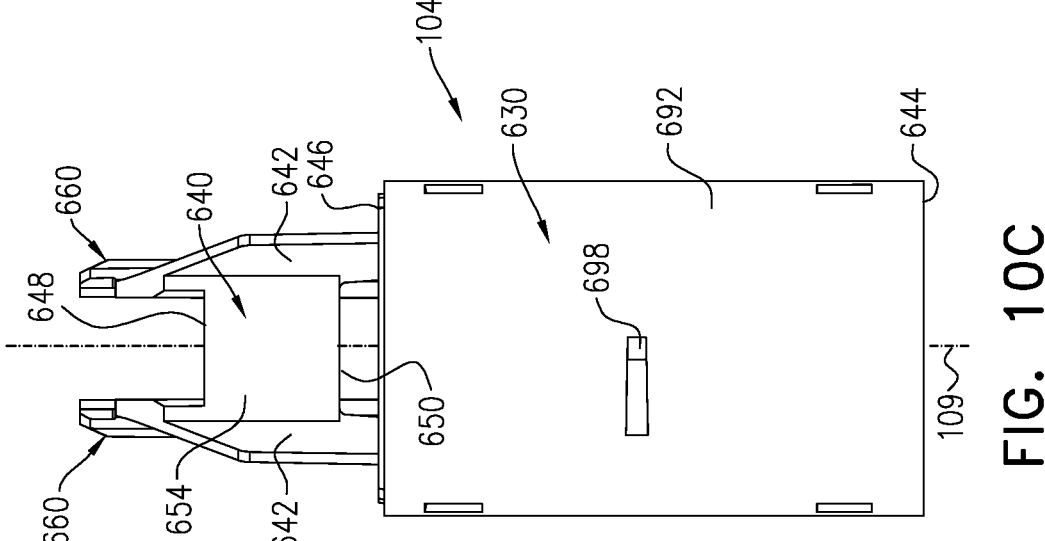
Figure 10E:
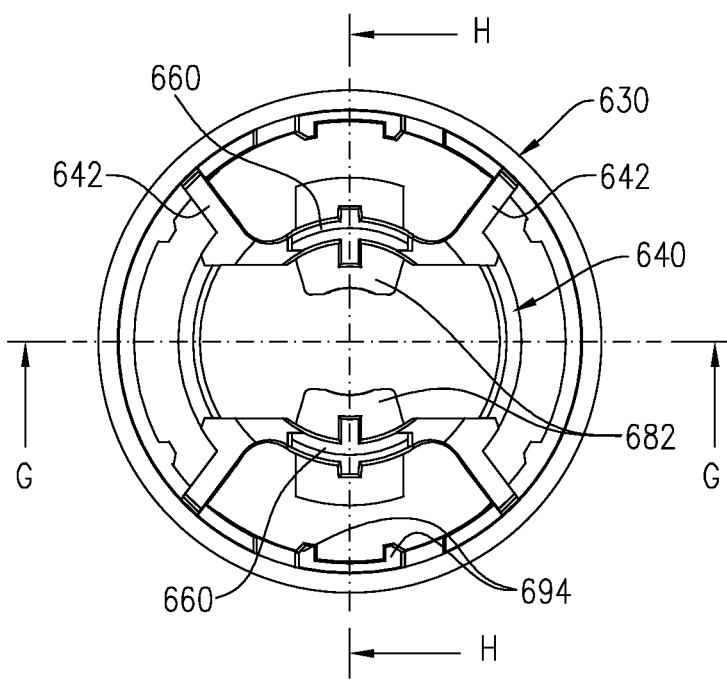
Figure 10F:
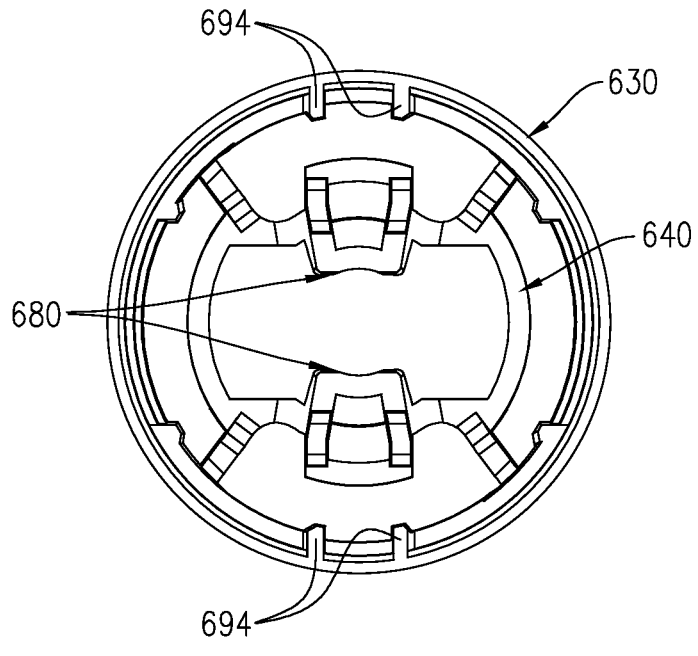
Figure 10H:
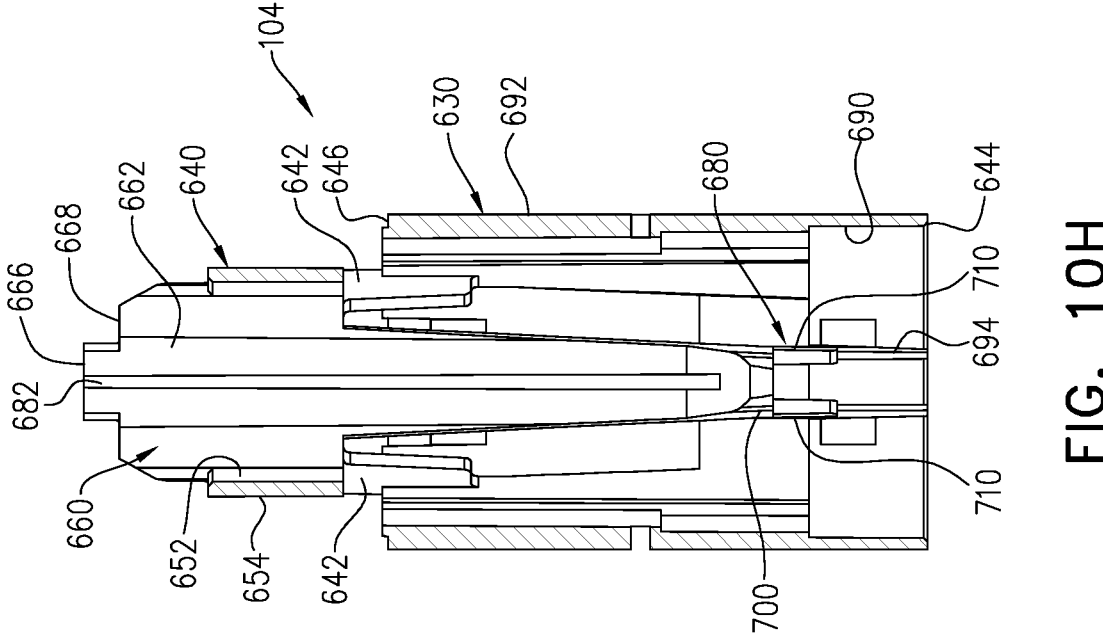
Figure 10G:
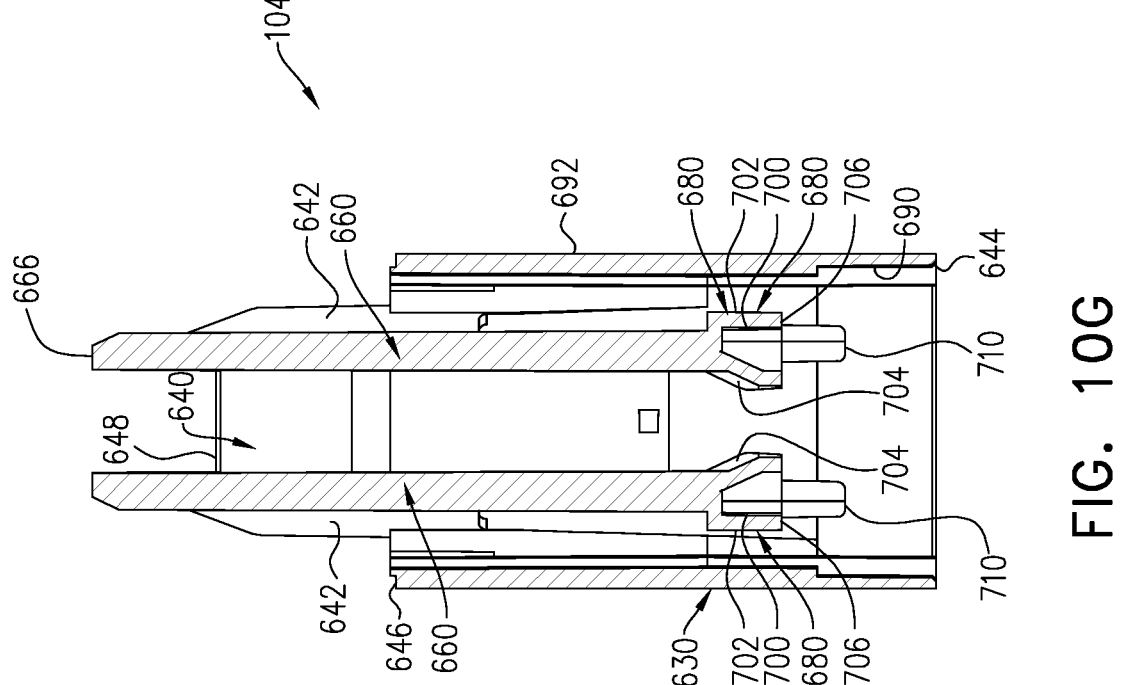

Reference is now made to FIGS. 10A, 10B, 10C, 10D, 10E, 10F, 10G & 10H, which are respectively a simplified perspective view of a forward-facing portion, a simplified perspective view of a rearward-facing portion, two simplified side plan views, a simplified top plan view, a simplified bottom plan view and two simplified sectional views taken along lines G-G and lines H-H in FIG. 10E of the rear housing portion 104 forming part of the rear sub-assembly 500 of the automatic injection device 100 of FIGS. 1A and 1B.

The rear housing portion 104 preferably is an integrally formed element, preferably injection molded of plastic and is arranged along longitudinal axis of symmetry 109.

It is seen in FIGS. 10A-10H that the rear housing portion 104 includes a generally cylindrical outer portion 630 extending along axis 109 and a generally partially cylindrical inner portion 640 is connected thereto by connecting ribs 642 and is coaxial therewith. The outer portion 630 defines a forward circumferential edge 644 and a rearward circumferential edge 646. The inner portion 640 is generally spaced rearwardly from the rearward circumferential edge 646 and defines a rearward edge 648 and a forward edge 650. The inner portion 640 further defines an inner surface 652 and an outer surface 654.

Typically, two longitudinal arms 660 are formed as part of the inner portion 640 and are disposed diametrically opposite with respect to each other. The longitudinal arms 660 extend both rearwardly from rearward edge 648 and forwardly from forward edge 650. Longitudinal arms 660 define an inner surface 662 and an outer surface 664. A rearwardly extending protrusion 666 is formed on a rearward edge 668 of each one of the longitudinal arms 660 and extends rearwardly therefrom. A locking member 680 is formed at the forward end of each of the longitudinal arms 660.

A longitudinal guiding rib 682 is formed on the inner surface 662 of each of the longitudinal arms 660.

The outer portion 630 defines an inner surface 690 and an outer surface 692 and two pairs of guiding ribs 694 are formed on the inner surface 690 of the outer portion 630. The two pairs of guiding ribs 694 are disposed diametrically opposite with respect to each other. The outer portion 630 additionally includes typically two apertures 698, which are formed on the circumference thereof and are disposed diametrically opposite with respect to each other.

The locking members 680 disposed at the forward ends of longitudinal arms 660 include wide portions 700 extending both outwardly and inwardly of the longitudinal arms 660, defining outer surfaces 702 facing the inner surface 690 of the outer portion 630. The wide portions 700 also define forwardly tapered inner surfaces 704 facing each other. The wide portions 700 define forward edges 706 and a pair of spaced apart fingers 710 extending forwardly therefrom.

The outer portion 630 additionally includes typically two pairs of apertures 712, which are formed on the circumference thereof and are disposed diametrically opposite with respect to each other, located adjacent the rearward end 646 of the outer portion 630 and two pairs of apertures 714, which are formed on the circumference thereof and are disposed diametrically opposite with respect to each other, located adjacent the forward end 644 of the outer portion 630.

Figure 11A:
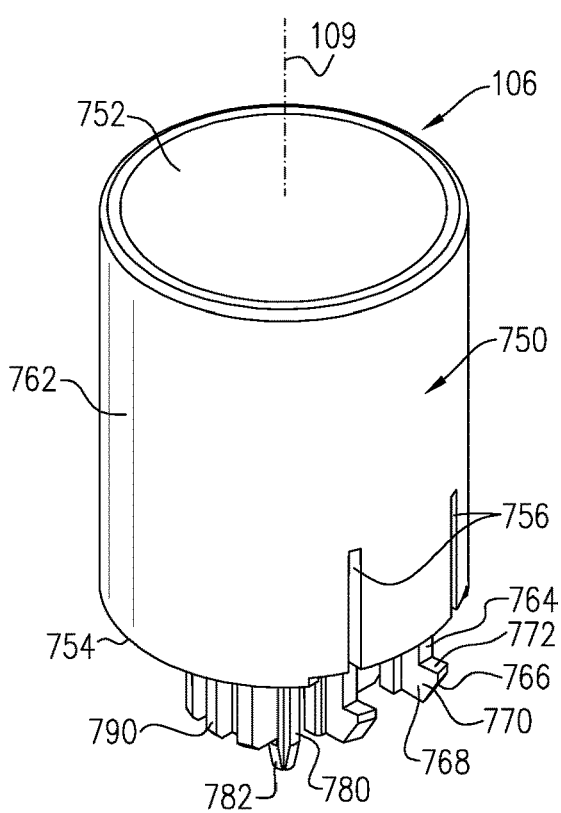
FIGS. 11A, 11B, 11C, 11D, 11E, 11F & 11G are respectively a simplified perspective view of a rearward-facing portion, a simplified perspective view of a forward-facing portion, a simplified side plan view, a simplified bottom plan view and three simplified sectional views taken along lines E-E, lines F-F and lines G-G in FIG. 11D of a rear cover forming part of the rear sub-assembly of the automatic injection device of FIGS. 1A and 1B.
Figure 11B:
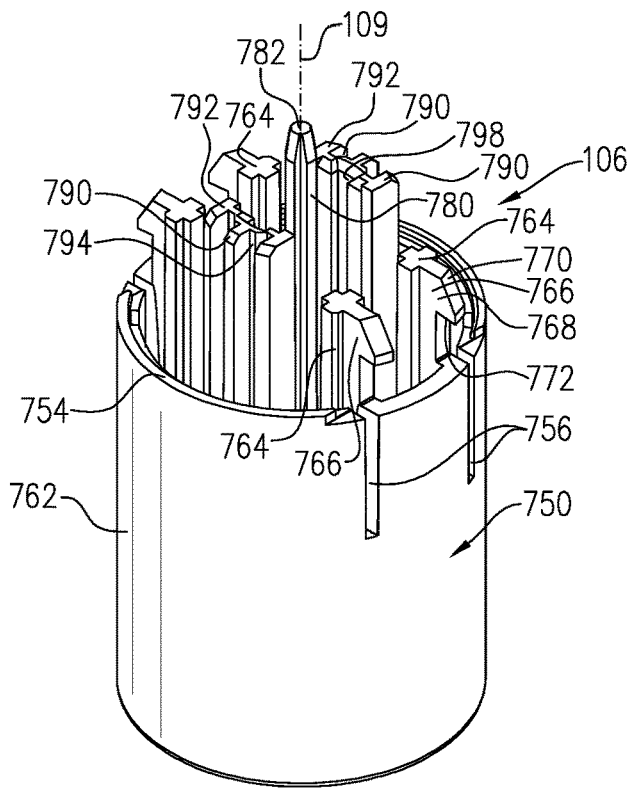
Figure 11C:
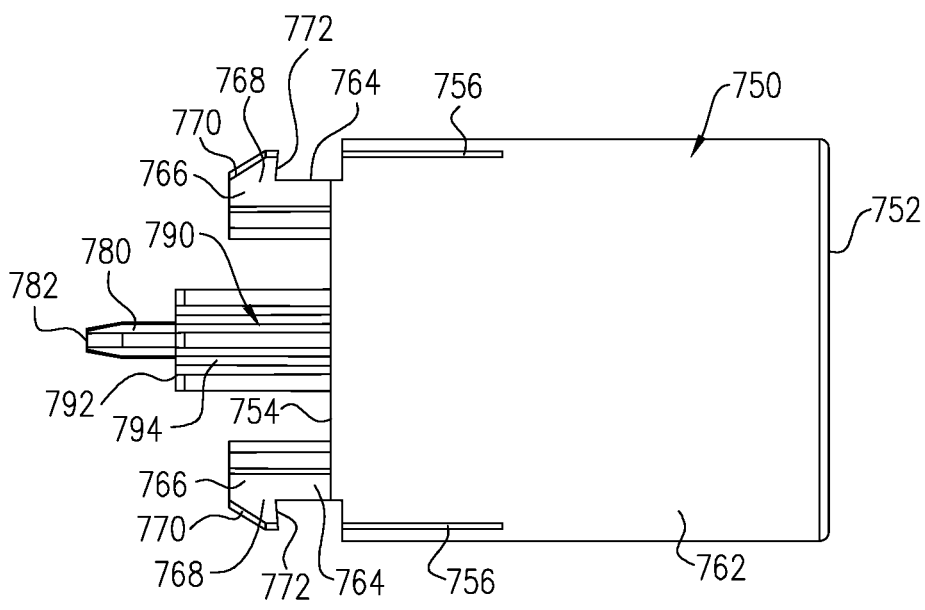
Figure 11D:
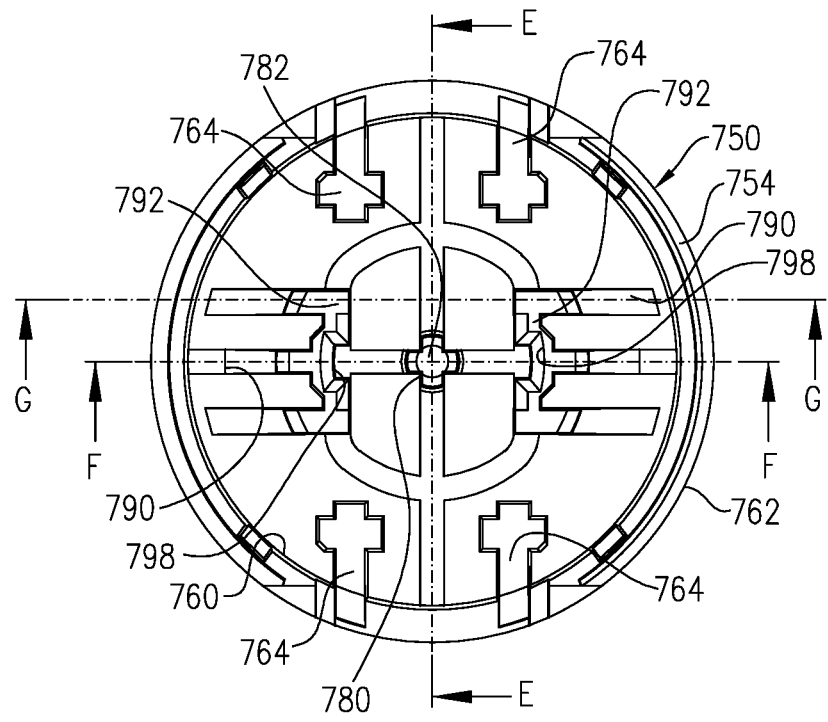
Figures 11E, 11F, 11G:
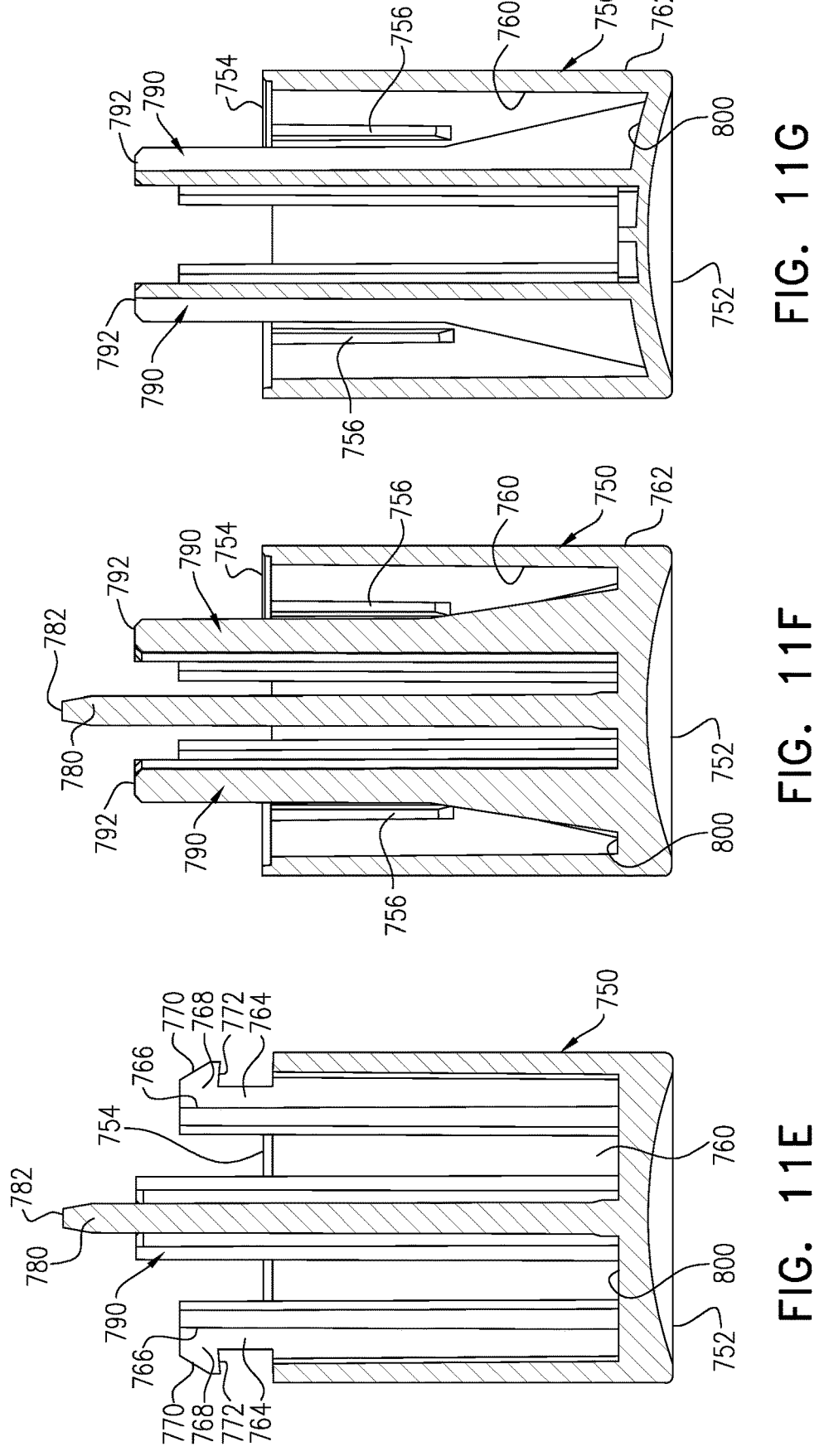

Reference is now made to FIGS. 11A, 11B, 11C, 11D, 11E, 11F & 11G, which are respectively a simplified perspective view of a rearward-facing portion, a simplified perspective view of a forward-facing portion, a simplified side plan view, a simplified bottom plan view and three simplified sectional views taken along lines E-E, lines F-F and lines G-G in FIG. 11D of the rear cover 106 forming part of the rear sub-assembly 500 of the automatic injection device 100 of FIGS. 1A and 1B.

The rear cover 106 preferably is an integrally formed element, preferably injection molded of plastic and is arranged along longitudinal axis of symmetry 109.

The rear cover 106 has a cylindrical portion 750 with a closed rearward end defining a generally concave wall portion 752. The cylindrical portion 750 defines a forward end 754 and a plurality of generally longitudinal openings 756 extending rearwardly from forward end 754 to provide relative resilience to the cylindrical portion 750 to enable assembly thereof with the rear housing portion 104.

The cylindrical portion 750 further defines an inner surface 760 and an outer surface 762. Typically, two pairs of diametrically opposed spaced apart longitudinal ribs 764 are formed on the inner surface 760 of the cylindrical portion 750. The ribs 764 extend forwardly from wall portion 752 and each terminates at a forward protrusion 766 disposed forwardly of the forward end 754. The forward protrusion 766 has a portion 768 that extends radially outwardly from rib 764 and preferably includes a rearwardly tapered surface 770 and a rearwardly facing shoulder 772.

A central pin 780 is formed on wall portion 752 and extends forwardly therefrom and terminates at a forward end 782 disposed forwardly of forward edge 754.

Two longitudinal ribs 790 extend forwardly from wall portion 752 and are facing each other. The ribs 790 are disposed radially outwardly of the central pin 780 and each of the ribs 790 is disposed between the two pairs of ribs 764. The ribs 790, each defines a forward edge 792, an outer surface 794 and an inner surface 796. A longitudinal groove 798 is formed along the inner surface 796 of each of the ribs 790.

It is seen in FIGS. 11A-11G that the wall portion 752 has a forwardly facing surface 800, which serves as a spring seat.

Figure 12A:
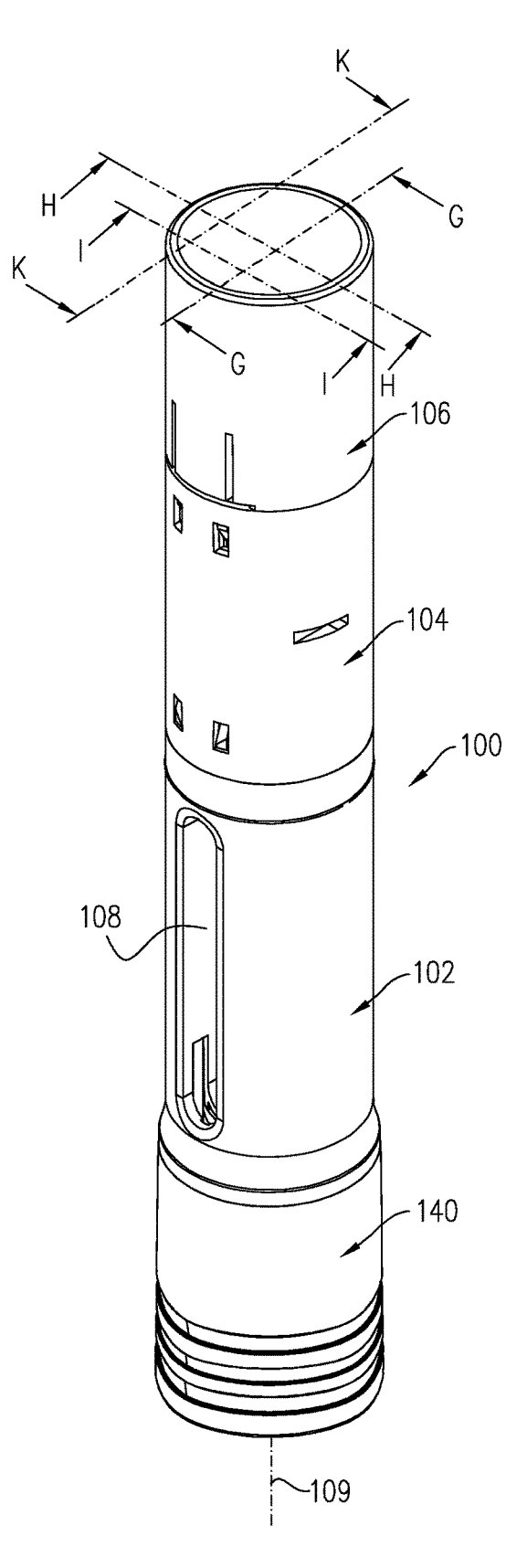
FIGS. 12A, 12B, 12C, 12D, 12E, 12F, 12G, 12H, 12I, 12J & 12K are simplified illustrations of the automatic injection device of FIGS. 1A-11G in a "storage" operative orientation, including a simplified perspective view, a simplified side plan view, two simplified side plan views with cut-out sections, five simplified sectional views taken along lines E-E and lines F-F in FIG. 12B, lines G-G, lines H-H, lines I-I and lines K-K in FIG. 12A, and a simplified partial sectional view shown without a portion of the front sub-assembly of FIG. 3 and taken along lines J-J in FIG. 12B.
Figure 12B:
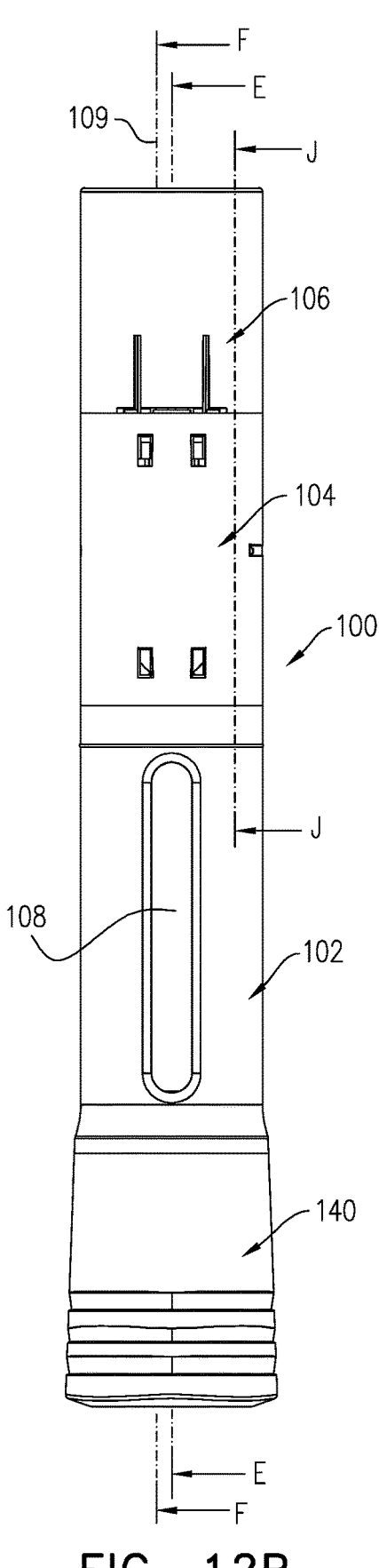

Reference is now made to FIGS. 12A, 12B, 12C, 12D, 12E, 12F, 12G, 12H, 12I, 12J & 12K, which are simplified illustrations of the automatic injection device 100 of FIGS. 1A-11G in a "storage" operative orientation, including a simplified perspective view, a simplified side plan view, two simplified side plan views with cut-out sections, six simplified sectional views taken along lines E-E and lines F-F in FIG. 12B, lines G-G, lines H-H, lines I-I and lines K-K in FIG. 12A, and a simplified partial sectional view shown without a portion of the front sub-assembly of FIG. 3 and taken along lines J-J in FIG. 12B.

The automatic injection device 100 comprises front housing portion 102, which is fixedly attached to the rear housing portion 104, which is in turn fixedly attached to the rear cover 106 and together forming an enclosure for the prefilled syringe 120. The rear cover 106 is fixedly attached to rear housing portion 104 preferably by means of engagement between apertures 712 in the rear housing portion 104 and forward protrusion 766 of the rear cover 106.

It is particularly seen in FIGS. 12E, 12F, 12I and 12K that the plunger rod element 110 is slidably disposed partially within the rear cover 106 and partially within the rear housing portion 104 in this storage operative orientation, such that central pin 780 of the rear cover 106 is inserted into the interior bore 582 of the plunger rod element 110 and the injection spring 112 is enclosed within the interior bore 582 and around the central pin 780 and being supported against rearwardly facing surface 620 of the plunger rod element 110 and between forwardly facing surface 800 of the rear cover 106.

The plunger rod element 110 is disposed interiorly of inner portion 640 of the rear housing portion 104 and interiorly of longitudinal ribs 790 of the rear cover 106. The longitudinal ribs 790 are outwardly supported by the inner portion 640. The plunger rod element 110 is held in place in its rearwardmost position in this storage operative orientation and is configured to be slidably longitudinally guided to be displaced along longitudinal axis 109, whereas guiding ribs 590 of the plunger rod element 110 are guided within grooves 798 formed between ribs 790 of the rear cover 106. It is additionally seen that guiding ribs 682 of the rear housing portion 104 are seated in grooves 594 of the plunger rod element 110 and slidably disposed therewithin in order to provide axial guidance of the plunger rod element 110.

It is further seen in FIGS. 12E, 12F, 12I and 12K that the trigger ring 114 is arranged interiorly of the rear housing portion 104 and coaxially therewith. The trigger ring 114 is prevented from rotation about longitudinal axis 109 due to the fact that it is configured to be axially guided by means of engagement of guiding rib 550 of the trigger ring 114 in between pair of ribs 694 formed on the rear housing portion 104.

It is a particular feature of an embodiment of the present invention that the trigger ring 114 is movably coupled to the rear housing portion 104, specifically by engagement of outwardly extending protrusions 542 of the trigger ring 114 with apertures 698 formed in the rear housing portion 104. The trigger ring 114 is prevented from inadvertent displacement relative to the rear housing portion 104 in this storage operative orientation due to this engagement of outwardly extending protrusions 542 with apertures 698.

Figure 12C:
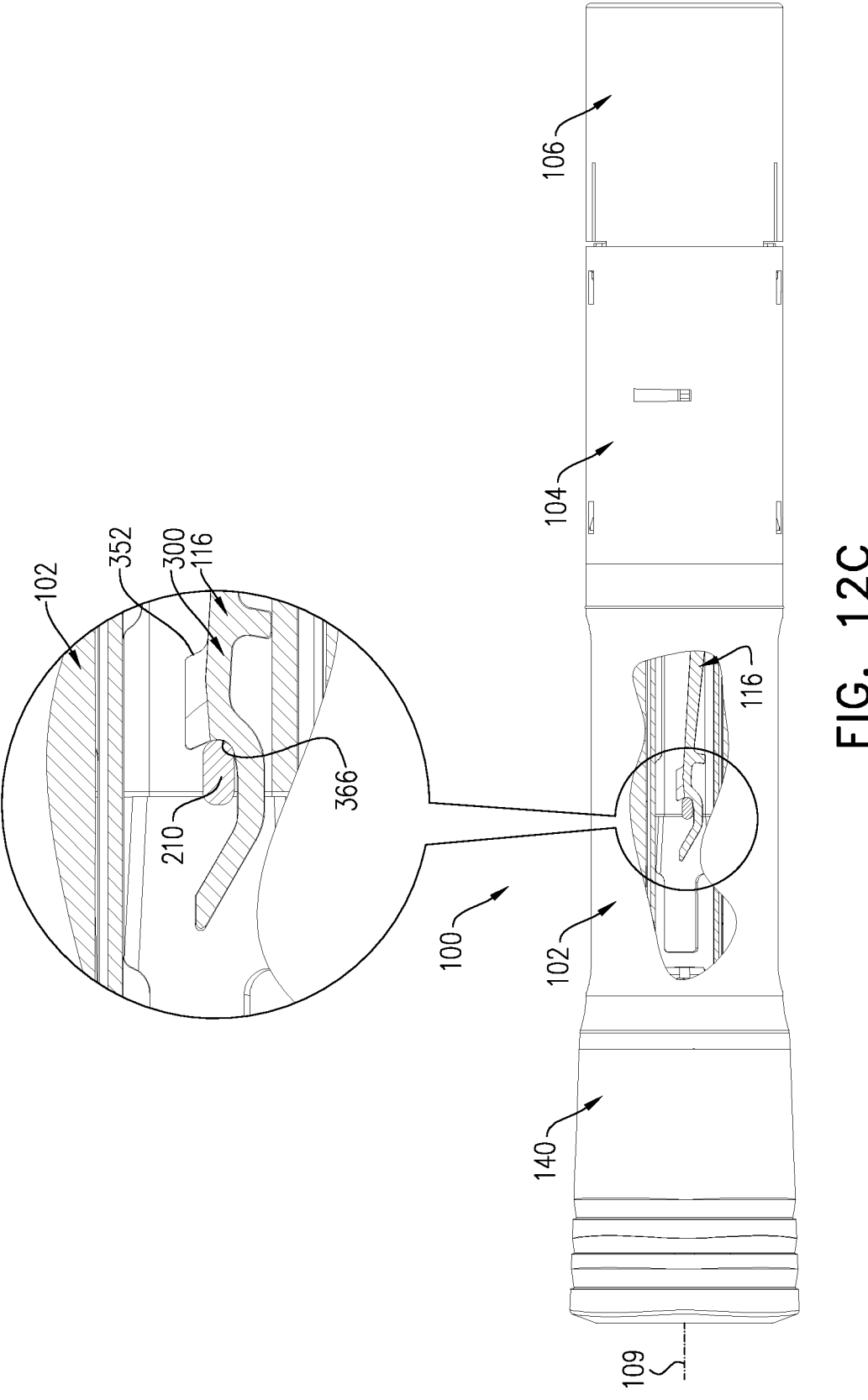
Figure 12D:
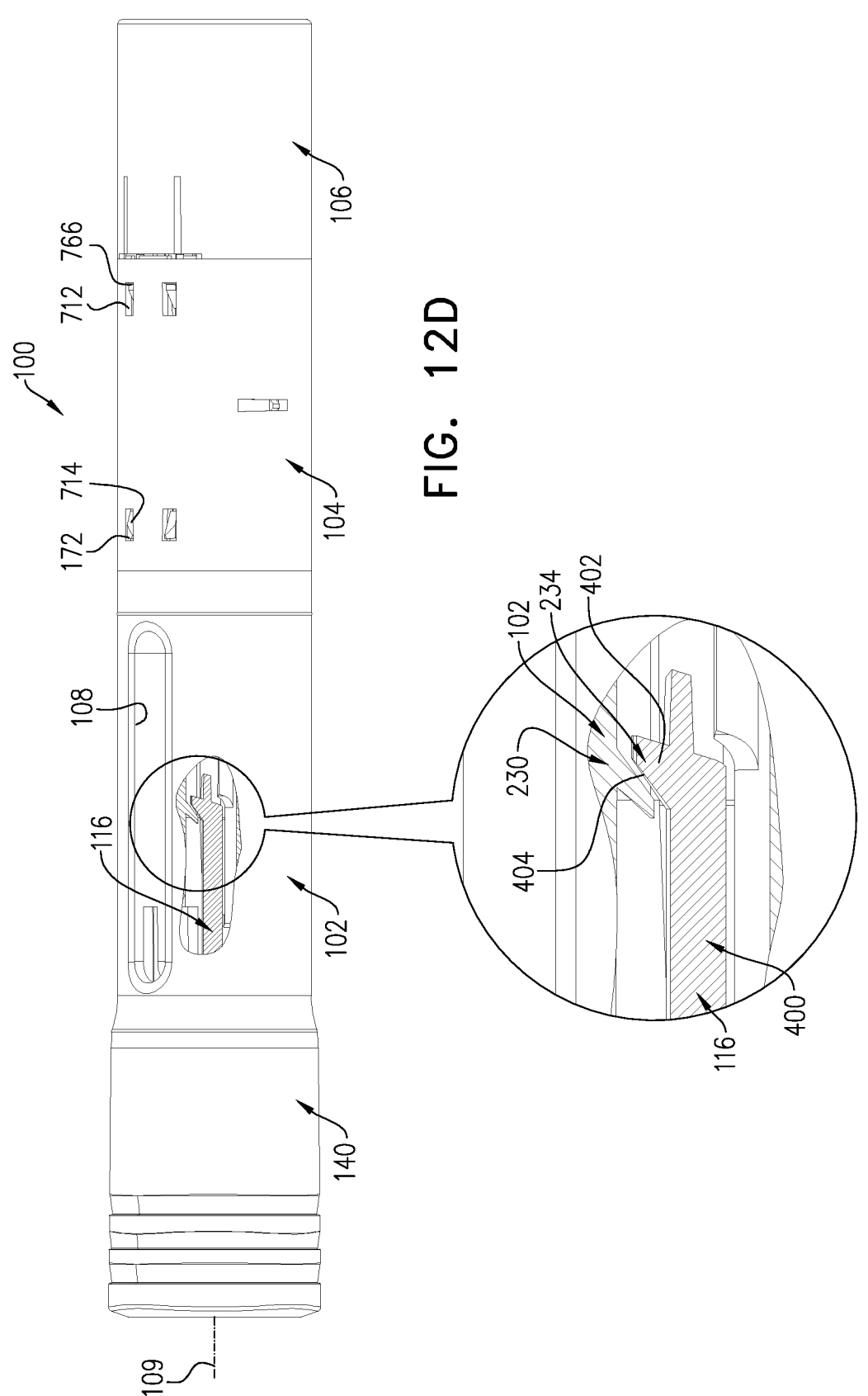
Figures 12E, 12F:
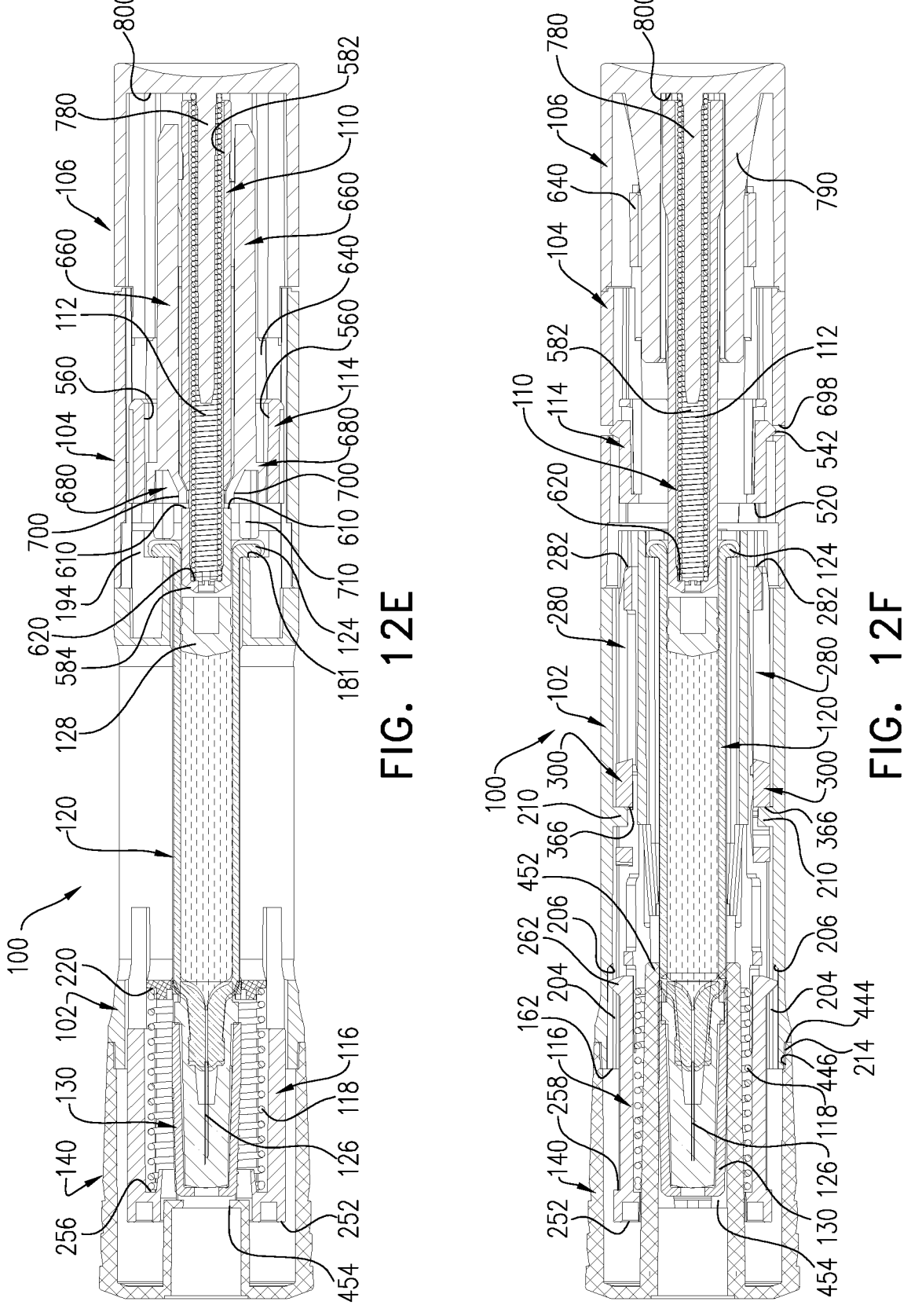
Figures 12G, 12H:
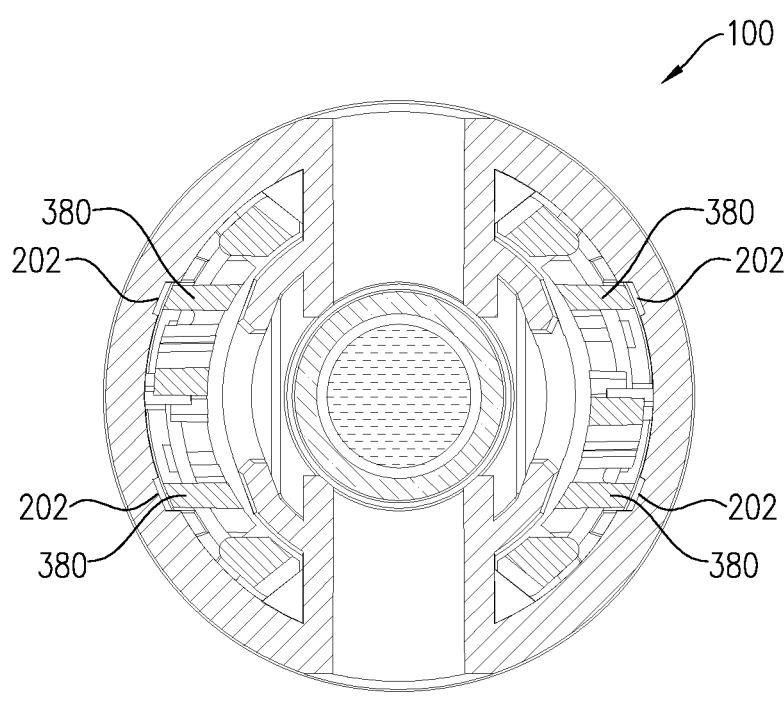
Figure 12J:
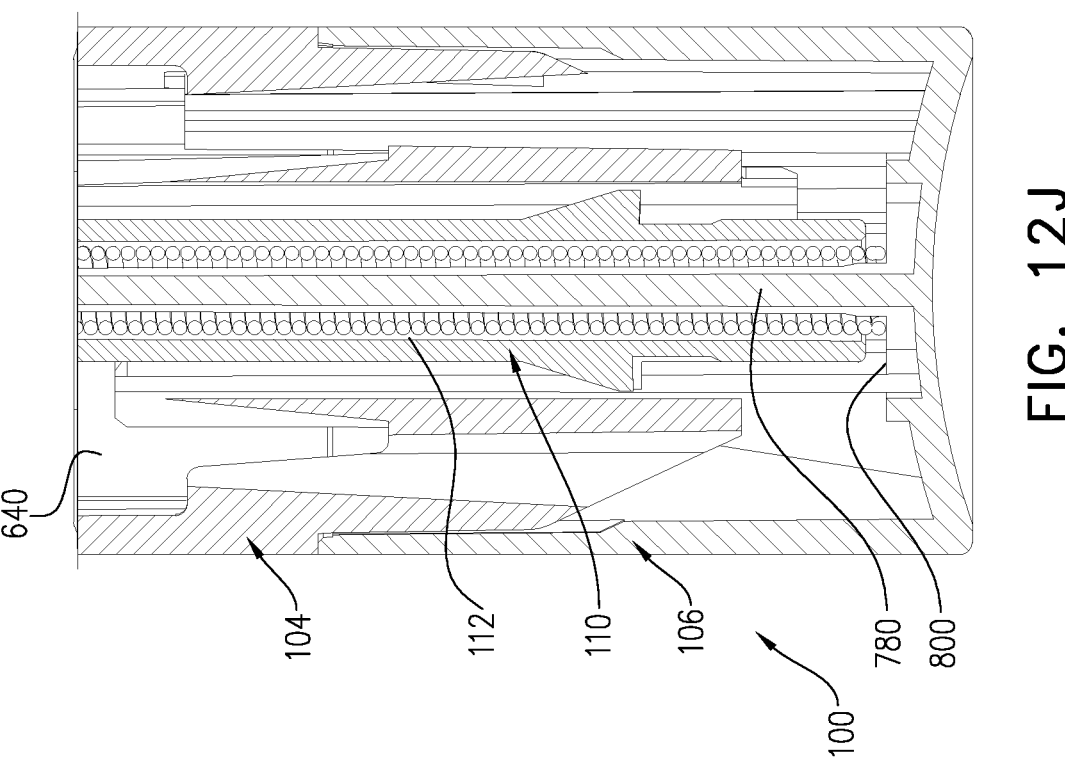
Figure 12I:
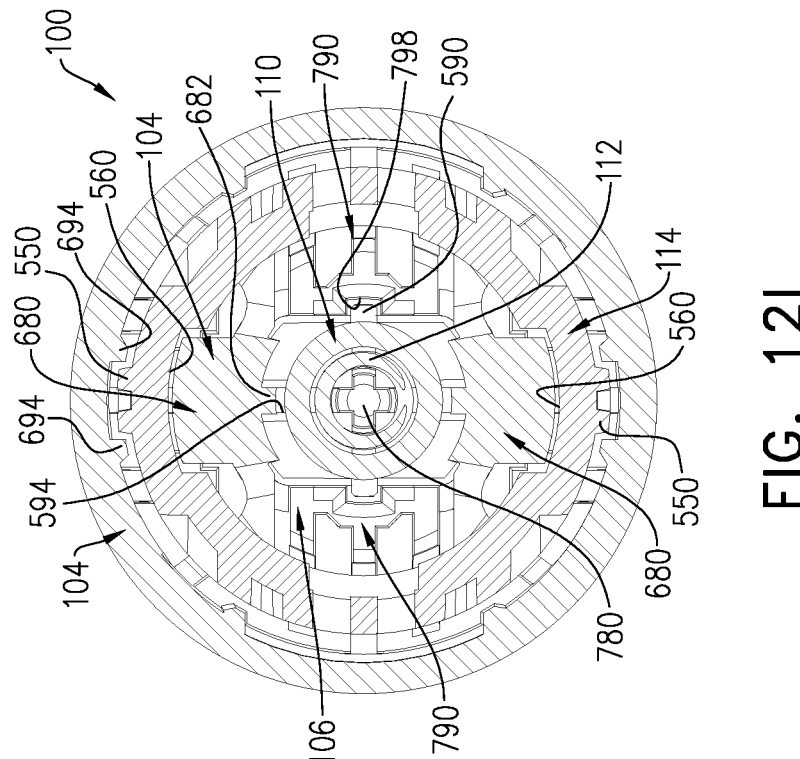
Figure 12K:
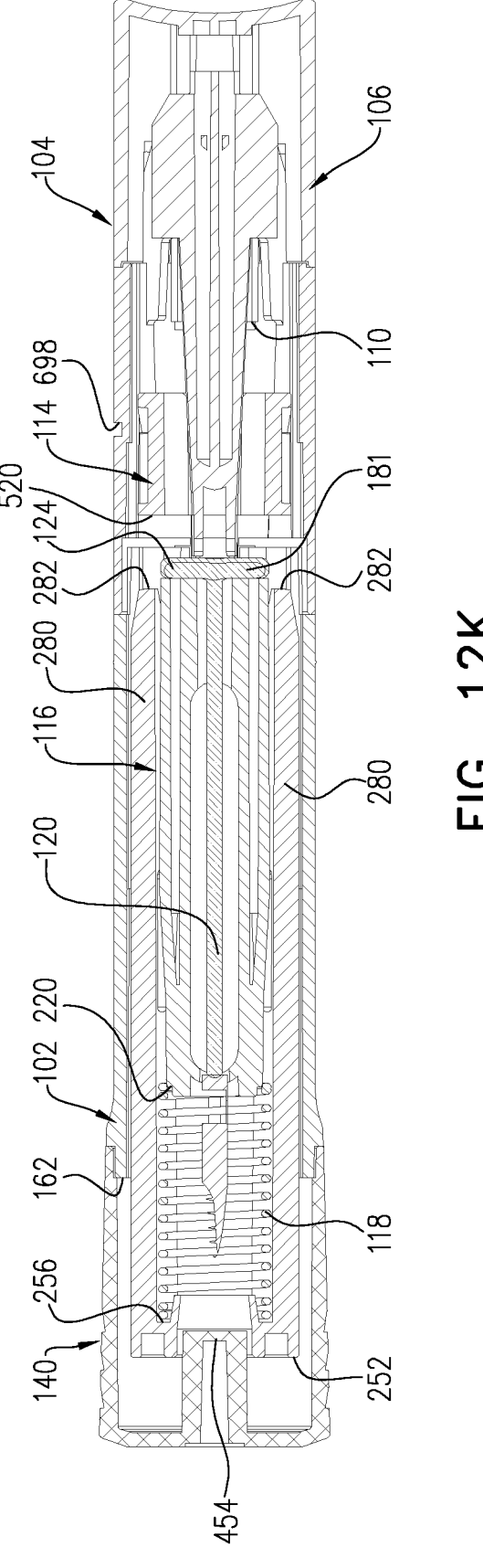

It is a further particular feature of an embodiment of the present invention that as seen in FIGS. 12E & 12I, in this storage operative orientation, locking members 680 of longitudinal arms 660 of the rear housing portion 104 are outwardly radially supported against locking grooves 560 of the trigger ring 114, thus causing engagement of wide portions 700 of locking elements 680 with openings 610 of the plunger rod element 110 and preventing outward deflection of longitudinal arms 660 of the rear housing portion 104. This engagement of locking elements 680 of longitudinal arms 660 of the rear housing portion 104 with the plunger rod element 110 keeps the injection spring 112 in a relatively compressed orientation and prevents forward longitudinal displacement of the plunger rod element 110 under the biasing force of the injection spring 112. Thus, the plunger rod element 110 is retained in its rearwardmost position in this storage operative orientation due to engagement between the rear housing portion 104 and the plunger rod element 110, which is caused by engagement between the trigger ring 114 and the rear housing portion 104.

The front housing portion 102 is fixedly attached to the rear housing portion 104 by means of engagement of locking teeth 172 of the front housing portion 102 within apertures 714 of the rear housing portion 104.

It is a particular feature of an embodiment of the present invention that the pre-filled syringe 120 is fixedly and non-displaceably retained within the enclosure formed by the rear housing portion 104 and the front housing portion 102. Specifically, the flange 124 of the pre-filled syringe 120 is fixedly held between ribs 181 of the front housing portion 102 and between fingers 710 of longitudinal arms 660 of the rear housing portion 104. The pre-filled syringe 120 is prevented from being rotated about longitudinal axis 109 by means of engagement of protrusions 194 of the front housing portion 102 with the flange 124 of the pre-filled syringe 120.

It is further seen in FIGS. 12C, 12D, 12E, 12F and 12I that needle guard element 116 is partially inserted into front housing portion 102 and protrudes forwardly therefrom in order to protect the needle 126 of the pre-filled syringe 120 in this storage operative orientation. The needle guard element 116 is biased forwardly under the force of the needle guard spring 118, which is supported between forwardly facing spring seat 220 of the front housing portion 102 and annular internal surface 256 of the needle guard element 116.

The needle guard element 116 is axially longitudinally slidable within the front housing portion 102 and is axially guided by engagement of ribs 380 of the needle guard element 116 within longitudinal grooves 202 of the front housing portion 102 as seen in FIG. 12G.

It is a particular feature of an embodiment of the present invention that in this storage operative orientation rearwardmost ends 282 of mounting arms 280 of the needle guard element 116 are forwardly longitudinally spaced from forward triggering surface 520 of the trigger ring 114.

It is a further particular feature of an embodiment of the present invention that forward displacement of the needle guard element 116 relative to front housing portion 102 is prevented in this storage operative orientation due to engagement of inwardly directed protrusion 210 of the front housing portion 102 within second retaining portion 366 of the labyrinth protrusion 300 of the needle guard element 116, as particularly seen in FIG. 12C.

Rearward displacement of the needle guard element 116 is limited in this storage operative orientation by means of engagement between outwardly protruding fingers 262 of the needle guard element 116 with forwardly tapered surfaces 206 of partial grooves 204 of the front housing portion 102 up to exertion of a predetermined force threshold on body engaging surface 252 in a rearward direction, as particularly seen in FIG. 12F.

It is particularly seen in FIG. 12D that outwardly extending protrusion 402 of longitudinal arm 400 of the needle guard element 116 is disposed rearwardly of protrusion 230 of the front housing element 102 and located adjacent thereto, such that rearwardly facing tapered surface 234 of protrusion 230 preferably abuts forwardly facing tapered surface 404 of outwardly extending protrusion 402 to allow subsequent rearward displacement of the needle guard element 116 relative to the front housing portion 102.

It is appreciated that in this storage operative orientation, the needle cover remover 140 is removably mounted onto the front housing portion 102, thus preventing the user from applying force directly onto the needle guard element 116 in a rearward direction. The limitation of needle guard 116 rearward displacement in this storage operative orientation prevents such rearward displacement due to inadvertent activation, such as by dropping the automatic injection device 100, for example.

It is seen in FIG. 12F that rearwardly facing circumferential shoulder 258 of the needle guard element 116 is forwardly spaced in this storage operative orientation from the forward edge 162 of the front housing portion 102.

It is seen in FIGS. 12E, 12F and 12I that the needle cover remover 140 is mounted onto the forward end of the front housing portion 102 and surrounds the protruding portion of the needle guard element 116, such that forwardly facing shoulder 214 of the front housing portion 102 engages rearward edge 444 of needle cover remover 140 and forward edge 162 of the front housing portion 102 engages rearwardly facing shoulder 446 of the needle cover remover 140.

It is seen that the needle cover 130 is retained between protrusions 454 and gripping teeth 452 of the needle cover remover 140.

It is noted that longitudinal ribs 456 formed on gripping arms 450 of the needle cover remover 140 are adapted to engage longitudinal notches 386 formed in the needle guard element 116 for rotationally aligning the needle cover remover 140 relative to the needle guard element 116.

It is noted that during assembly of the automatic injection device 100, the labyrinth protrusion 300 is configured to be resiliently radially inwardly deflected toward the longitudinal axis 109 to allow mounting of the needle guard element 116 into the front housing portion 102. Specifically, during rearward insertion of the needle guard element 116 into the front housing portion 102, the labyrinth protrusion 300 is momentarily deflected radially inwardly towards longitudinal axis 109 when rearwardly tapered outwardly directed edge 352 of the labyrinth protrusion 300 slides over inwardly directed protrusion 210 of the front housing portion 102. It is particularly seen in FIG. 12C that protrusion 210 of the rear housing portion 104 is seated within the second retaining portion 366 of the labyrinth protrusion 300 in this storage operative orientation.

Figure 13A:
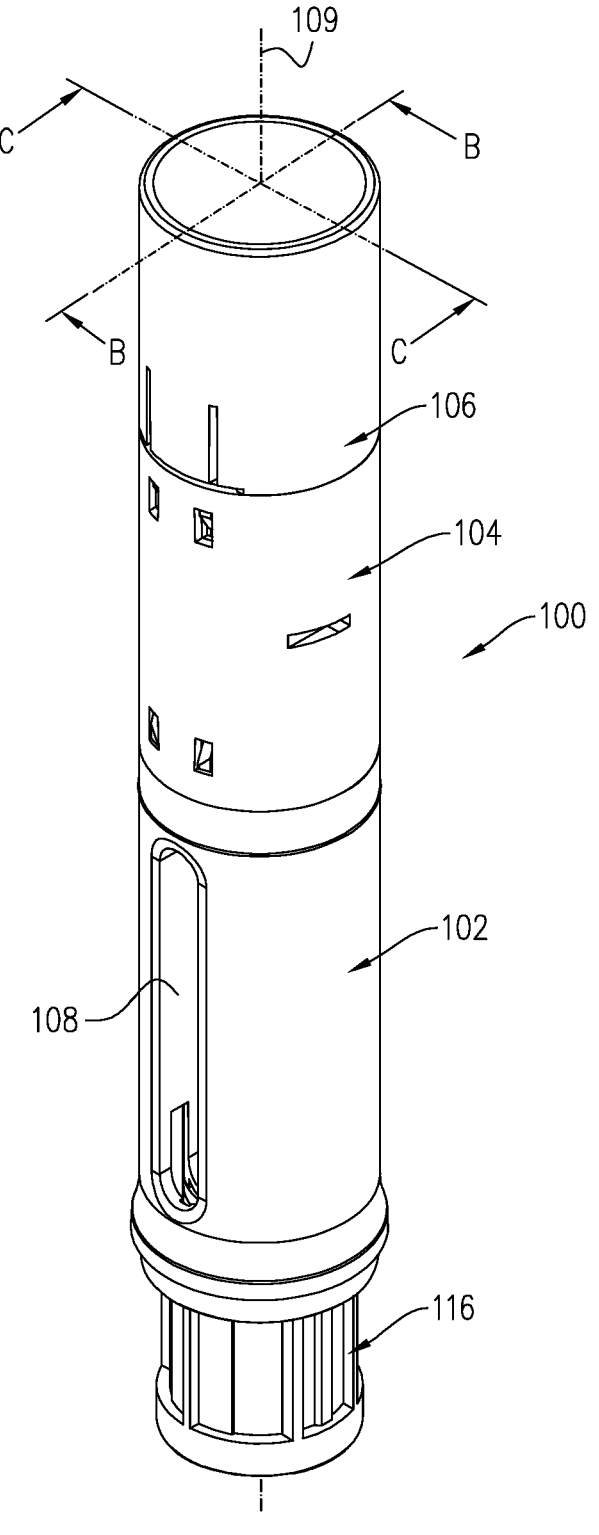
FIGS. 13A, 13B and 13C are simplified illustrations of the automatic injection device of FIGS. 1A-11G in a cover removal operative orientation, including a simplified perspective view and two simplified sectional views taken along lines B-B and lines C-C in FIG. 13A.
Figures 13B, 13C:
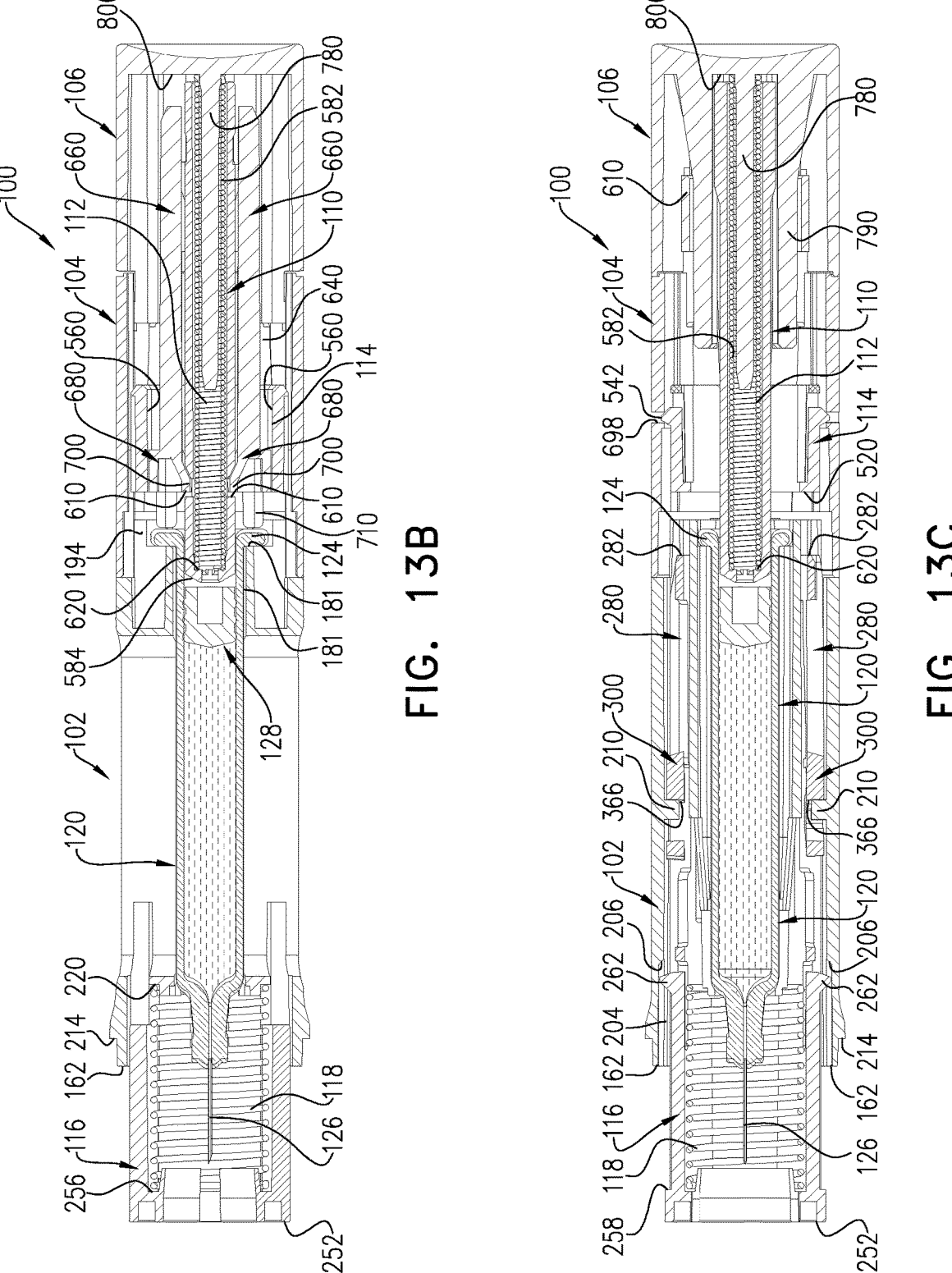

Reference is now made to FIGS. 13A, 13B and 13C, which are simplified illustrations of the automatic injection device 100 of FIGS. 1A-11G in a cover removal operative orientation, including a simplified perspective view and two simplified sectional views taken along lines B-B and lines C-C in FIG. 13A.

It is appreciated that all spatial relationships between the various components of the automatic injection device 100 remain the same as described hereinabove with respect to the storage operative orientation illustrated in FIGS. 12A-12K, besides the following spatial relationships:

The user grips the needle cover remover 140 and pulls it preferably longitudinally forwardly to detach it from the front housing portion 102 and thereby remove the needle cover 130 to expose needle 126 of the pre-filled syringe 120.

Following removal of the needle cover remover 140, the forward end of the needle guard element 116 is exposed and protrudes forwardly from the forward edge 162 of the front housing portion 102 to a first longitudinal extent.

It is noted that since needle cover remover 140 is not mounted onto the forward portion of the front housing portion 102 anymore, the needle guard element 116 is not prevented from rearward longitudinal displacement along axis 109 upon application of sufficient force on body engaging surface 252 in a rearward axial direction. Such application of force causes outwardly protruding fingers 262 of the needle guard element 116 to slide over forwardly tapered surfaces 206 of the front housing portion 102, which provides for inward deflection of snap portions 260 with respect to longitudinal axis 109 and thus enables rearward displacement of the needle guard element 116 relative to the front housing portion 102, along longitudinal axis 109.

The needle guard spring 118 remains in its relatively released operative state in this operative orientation and is configured to bias the needle guard element 116 forwardly to protect needle 126.

Figure 14A:
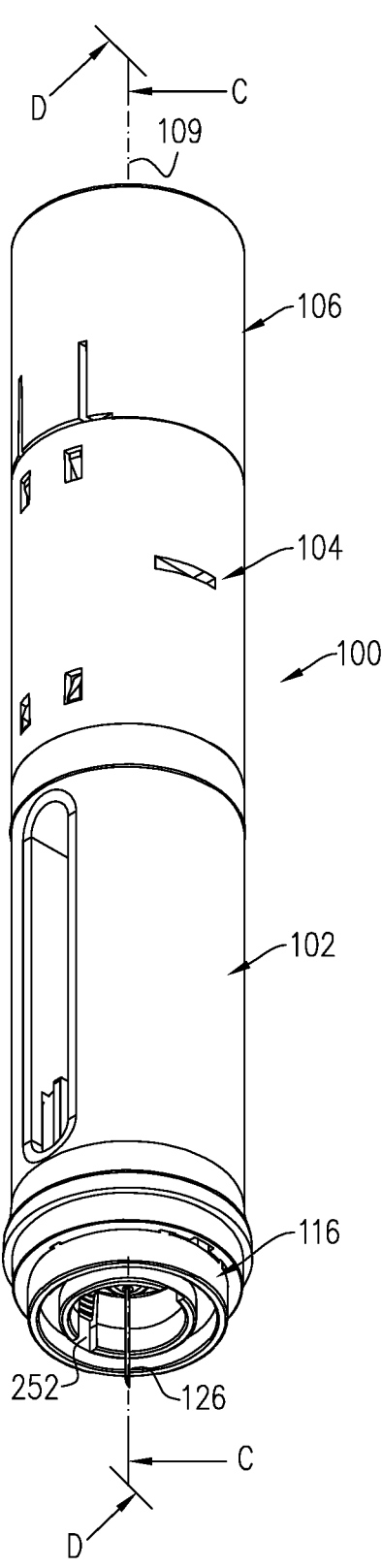
FIGS. 14A, 14B, 14C, 14D and 14E are simplified illustrations of the automatic injection device of FIGS. 1A-11G in a needle penetration and start of injection operative orientation, including a simplified perspective view, a simplified side plan view and three simplified sectional views taken along lines C-C and lines D-D in FIG. 14A and lines E-E in FIG. 14B.
Figure 14B:
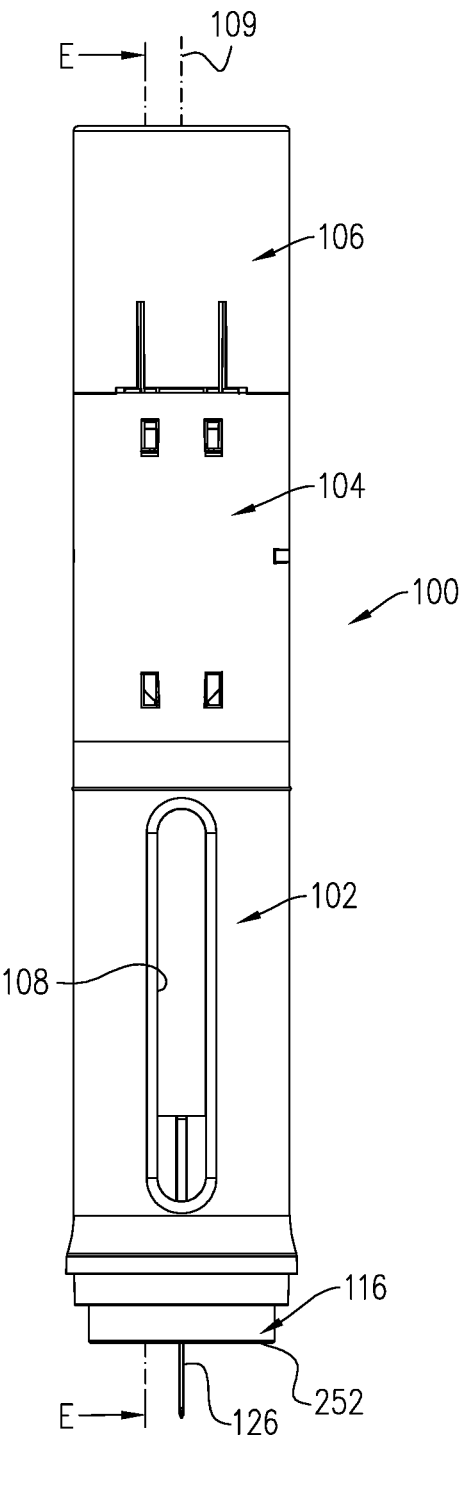

Reference is now made to FIGS. 14A, 14B, 14C, 14D and 14E, which are simplified illustrations of the automatic injection device 100 of FIGS. 1A-11G in a needle penetration and start of injection operative orientation, including a simplified perspective view, a simplified side plan view and three simplified sectional views taken along lines C-C and lines D-D in FIG. 14A and lines E-E in FIG. 14B. Reference is additionally made to FIGS. 14F & 14G, which are simplified partial plan view illustrations of a transition between forward position and rearward position of the needle guard element 116 of FIGS. 5A-5J relative to the front housing portion 102 of FIGS. 4A-4I.

It is appreciated that all spatial relationships between the various components of the automatic injection device 100 remain the same as described hereinabove with respect to the cover removal operative orientation illustrated in FIGS. 13A-13C, besides the following spatial relationships:

The user presses the automatic injection device 100 against an injection site, thus displaces the needle guard element 116 axially rearwardly along axis 109 with respect to the remainder of the automatic injection device 100, thus compresses needle guard spring 118 and initiates actuation of the automatic injection device 100.

Figures 14C, 14D:
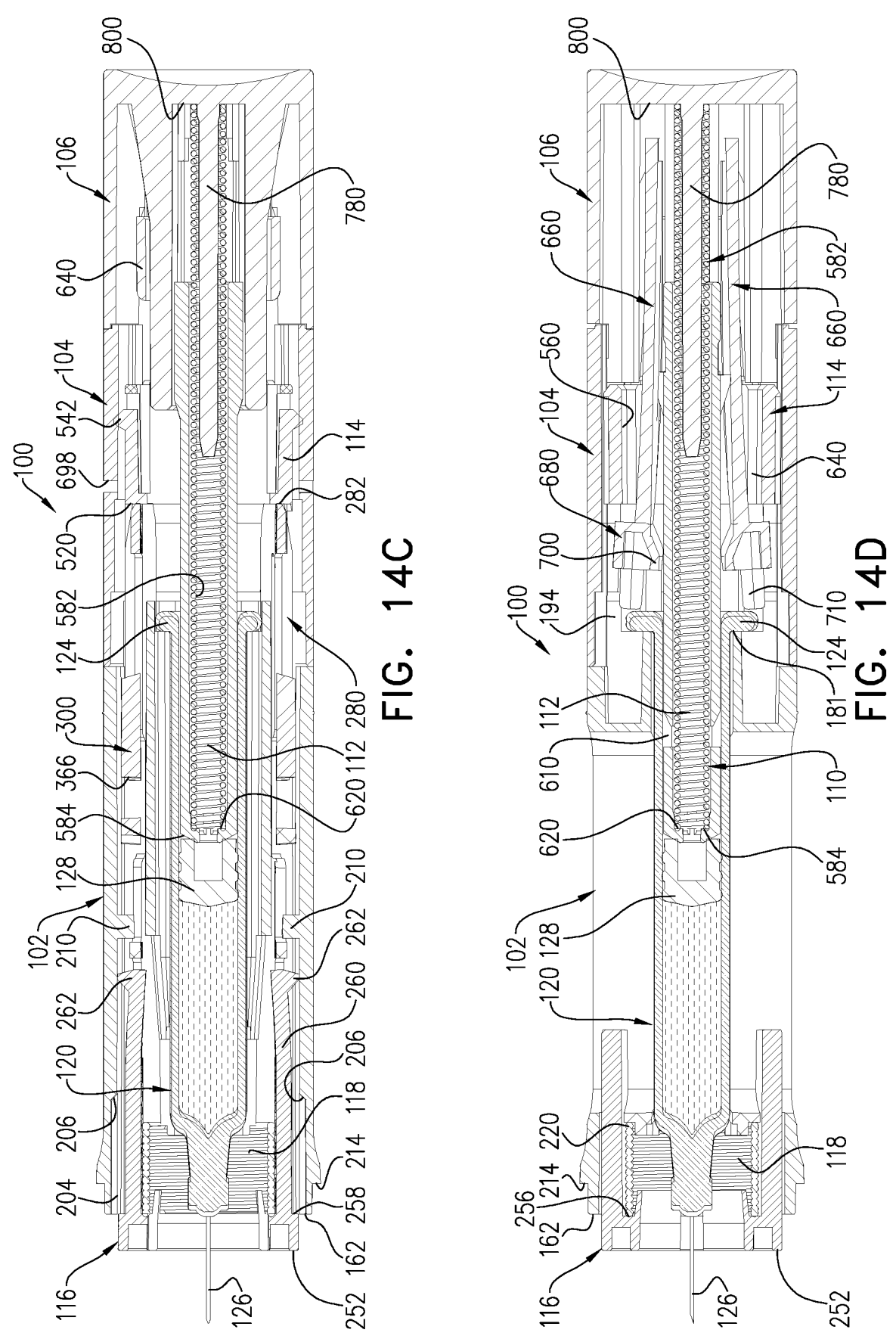
Figure 14E:
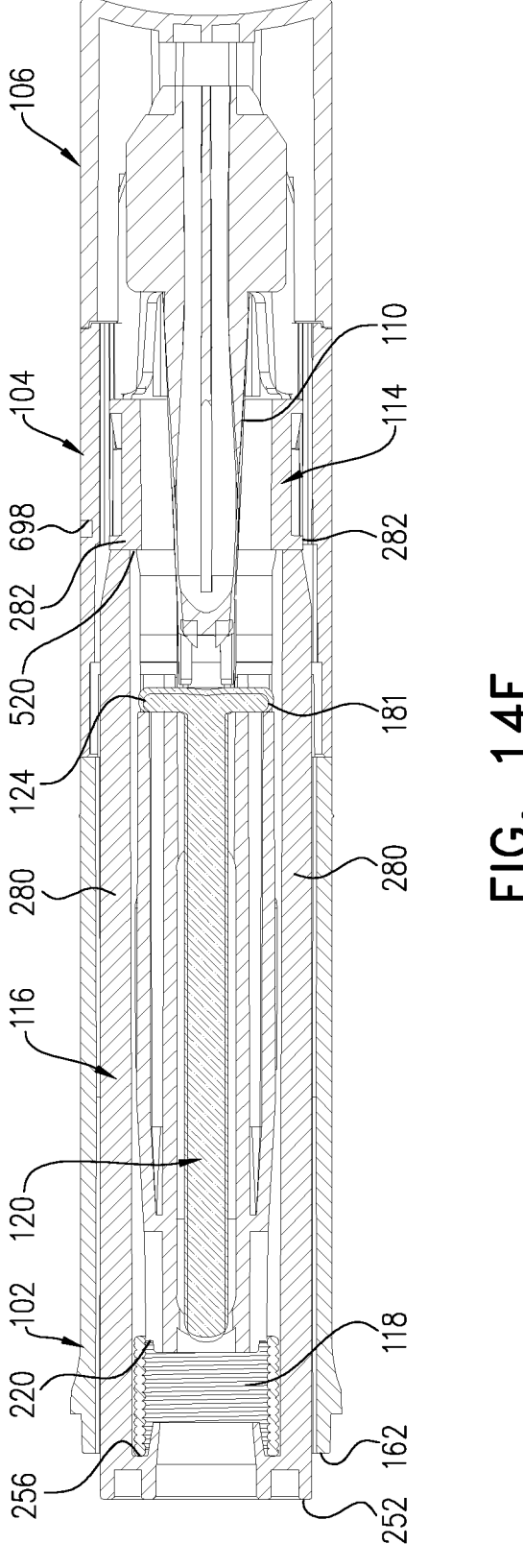
Figure 14F:
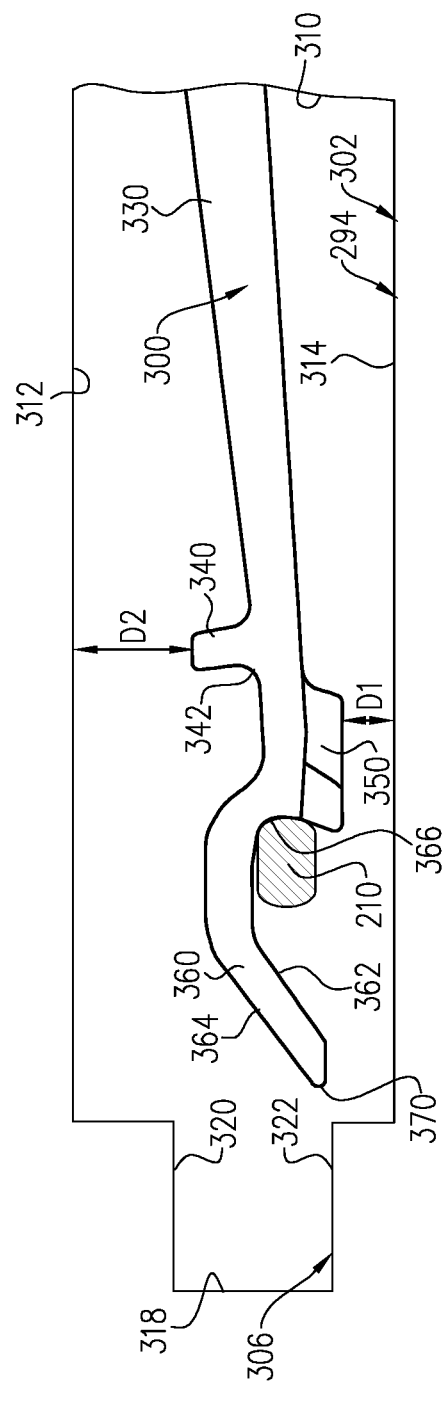
FIGS. 14F & 14G are simplified partial plan view illustrations of a transition between forward position and rearward position of the needle guard element of FIGS. 5A-5J relative to the front housing portion of FIGS. 4A-4I.
Figure 14G:
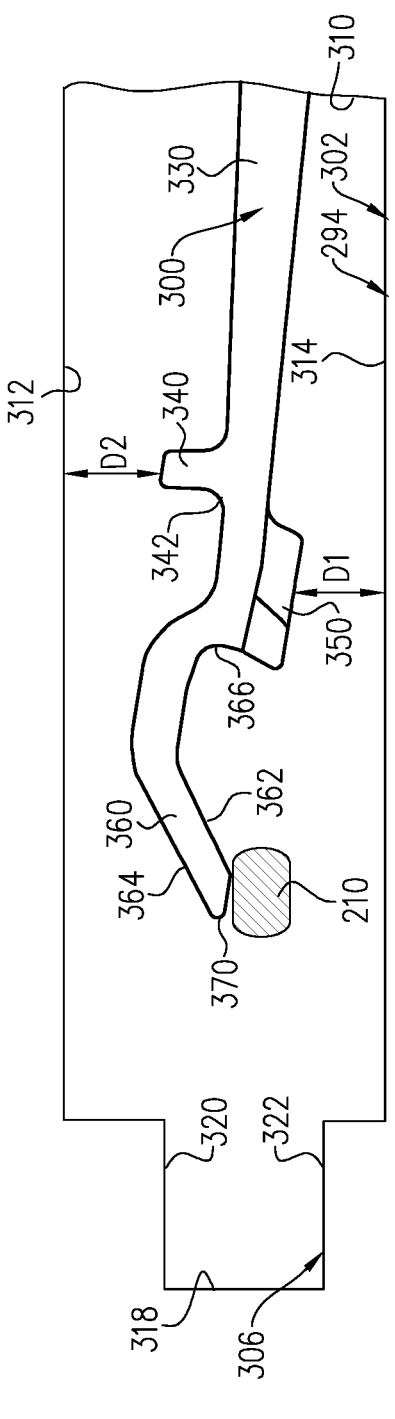

It is a particular feature of an embodiment of the present invention that upon rearward displacement of the needle guard element 116 along longitudinal axis 109, protruding fingers 262 of snap portions 260 of the needle guard element 116 slide over forwardly tapered surfaces 206 of the front housing portion 102 and thus the snap portions 260 are inwardly deflected toward longitudinal axis 109, as specifically seen in FIG. 14C.

It is seen in FIG. 14C that needle guard element 116 is rearwardly displaced along axis 109 up to engagement of rearwardly facing circumferential shoulder 258 of the needle guard element 116 with the forward edge 162 of the front housing portion 102.

It is a particular feature of an embodiment of the present invention that upon rearward displacement of the needle guard element 116 relative to the front housing portion 102, the needle 126 penetrates the injection site and the pre-filled syringe 120 remains static with respect to front housing portion 102 and with respect to rear housing portion 104.

It is a further particular feature of an embodiment of the present invention that upon rearward displacement of the needle guard element 116, rearward ends 282 of mounting arms 280 of the needle guard element 116 engage forward triggering surface 520 of the trigger ring 114. Upon engagement of needle guard element 116 with the trigger ring 114, the trigger ring 114 disengages from apertures 698 of the rear housing portion 104 and is being displaced rearwardly relative to the rear housing portion 104 along longitudinal axis 109 together with the needle guard element 116. It is specifically seen in FIG. 14C that upon abutment of rearwardly facing circumferential shoulder 258 of the needle guard element 116 with forward edge 162 of the front housing portion 102, the rearward ends 282 of the needle guard element 116 have displaced trigger ring 114 rearwardly, such that outwardly extending protrusions 542 of the trigger ring 114 are now disposed rearwardly of apertures 698 of the rear housing portion 104.

It is an even further particular feature of an embodiment of the present invention that upon rearward displacement of the trigger ring 114 relative to the rear housing portion 104, the locking members 680 of longitudinal arms 660 of the rear housing portion 104 disengage from the locking grooves 560 of the trigger ring 114. Once locking members 680 disengage from the locking grooves 560 of the trigger ring 114, longitudinal arms 660 of the rear housing portion 104 are not supported against outward deflection anymore.

It is a yet further particular feature of an embodiment of the present invention that rearward displacement of the trigger ring 114 provides for outward deflection of longitudinal arms 660 and thereby causes disengagement of wide portions 700 from openings 610 of the plunger rod element 110, which in turn causes release of the injection spring 112, which urges the plunger rod element 110 to be forwardly displaced into the pre-filled syringe 120 and engage the piston element 128.

Yet another particular feature of an embodiment of the present invention, as specifically seen in FIGS. 14F and 14G, is that upon rearward displacement of the needle guard element 116 relative to the front housing portion 102, the radially inwardly directed protrusions 210 formed on the inner surface of the front housing portion 102 laterally guide and deflect the labyrinth protrusion 300 of the needle guard element 116 in a first direction. This lateral guidance and deflection of labyrinth protrusion 300 is particularly illustrated in the transition shown between FIGS. 14F and 14G, reference to which is hereby specifically made.

It is specifically seen from the transition between FIGS. 14F and 14G that as the needle guard element 116 is rearwardly displaced relative to the front housing portion 102, the labyrinth protrusions 300 rearwardly displace relative to radially inwardly directed protrusions 210 of the front housing portion 102, and thus radially inwardly directed protrusions 210 which were retained within second retaining portions 366 as particularly seen in FIG. 12C are now displaced forwardly along curved hook extension 360 and toward forwardmost directing tip 370 of the labyrinth protrusion 300.

When needle guard element 116 is further displaced rearwardly up to abutment of rearwardly facing circumferential shoulder 258 of needle guard element 116 with forward edge 162 of the front housing portion 102, the inwardly directed protrusions 210 are guided within third longitudinal portion 306 toward forward edge 318. It is noted that during rearward displacement of the needle guard element 116 relative to the front housing portion 102, the labyrinth protrusion 300 is deflected laterally toward first side edge 312, such that distance D1 increases and distance D2 decreases accordingly, as particularly seen in FIG. 14G.

Figures 15A, 15B:
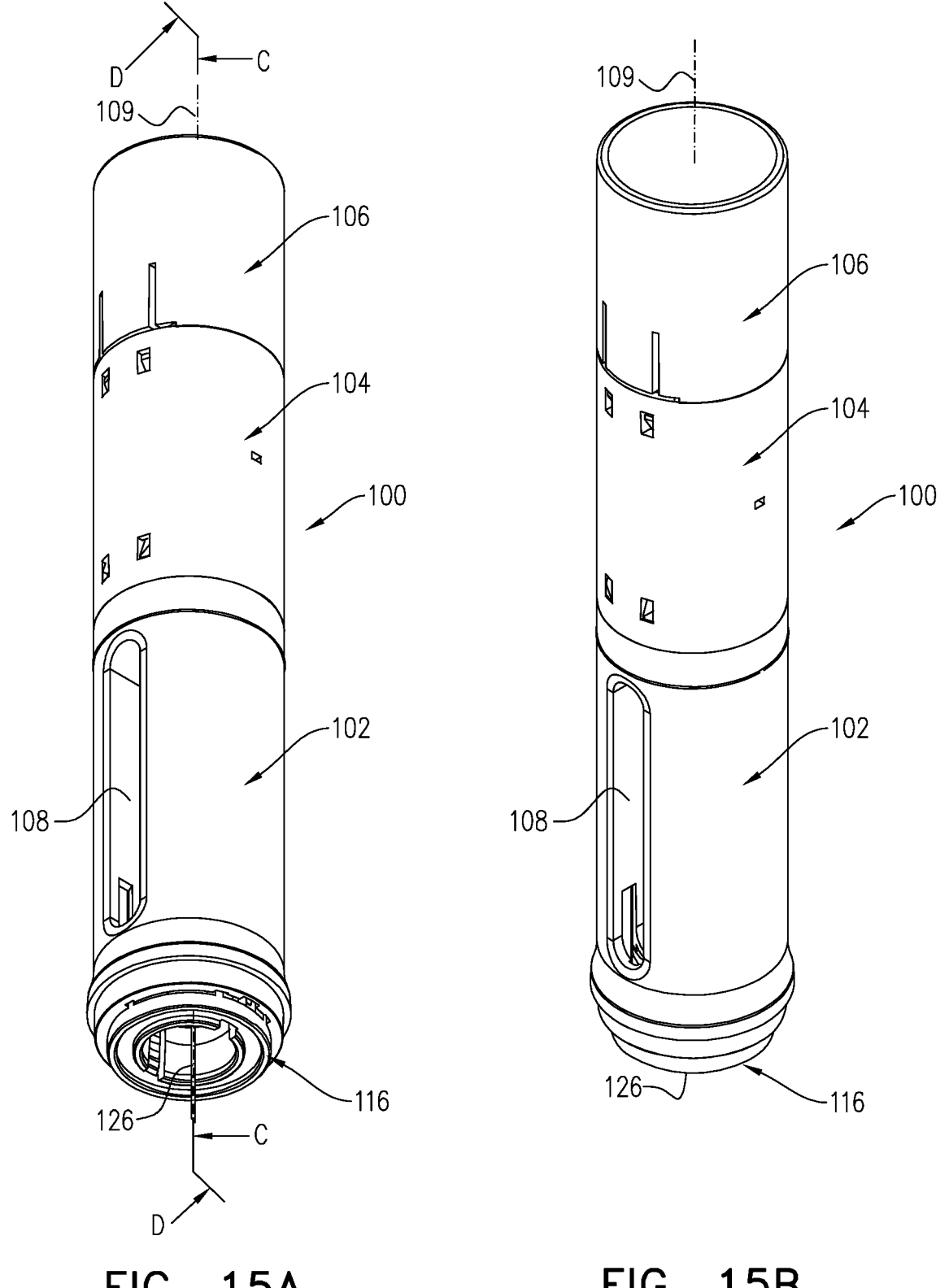
FIGS. 15A, 15B, 15C and 15D are simplified illustrations of the automatic injection device of FIGS. 1A-11G in an end of injection operative orientation, including a simplified perspective view, a simplified side plan view and two simplified sectional views taken along lines C-C and lines D-D in FIG. 15A.

Reference is now made to FIGS. 15A, 15B, 15C and 15D, which are simplified illustrations of the automatic injection device 100 of FIGS. 1A-11G in an end of injection operative orientation, including a simplified perspective view, a simplified side plan view and two simplified sectional views taken along lines C-C and lines D-D in FIG. 15A. Reference is additionally made to FIGS. 15E, 15F and 15G, which are simplified partial plan view illustrations of a transition between just prior to end of injection, during end of injection and just after end of injection of the plunger rod element 110 of FIGS. 9A-9H relative to the rear housing portion 104 of FIGS. 10A-10H.

Figure 15C:
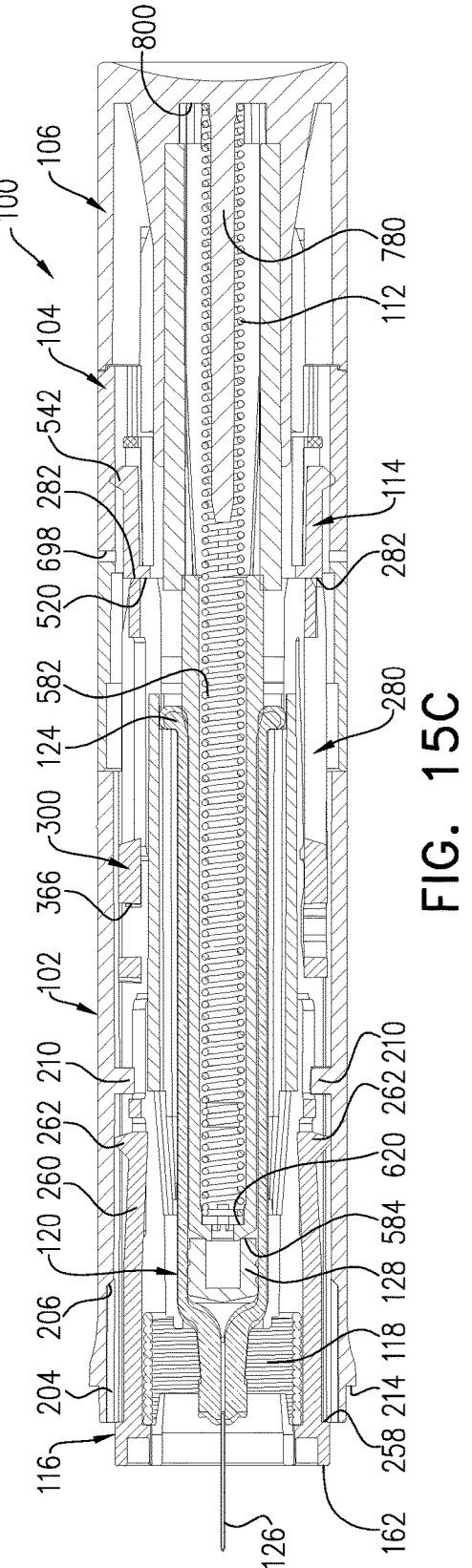
Figure 15D:
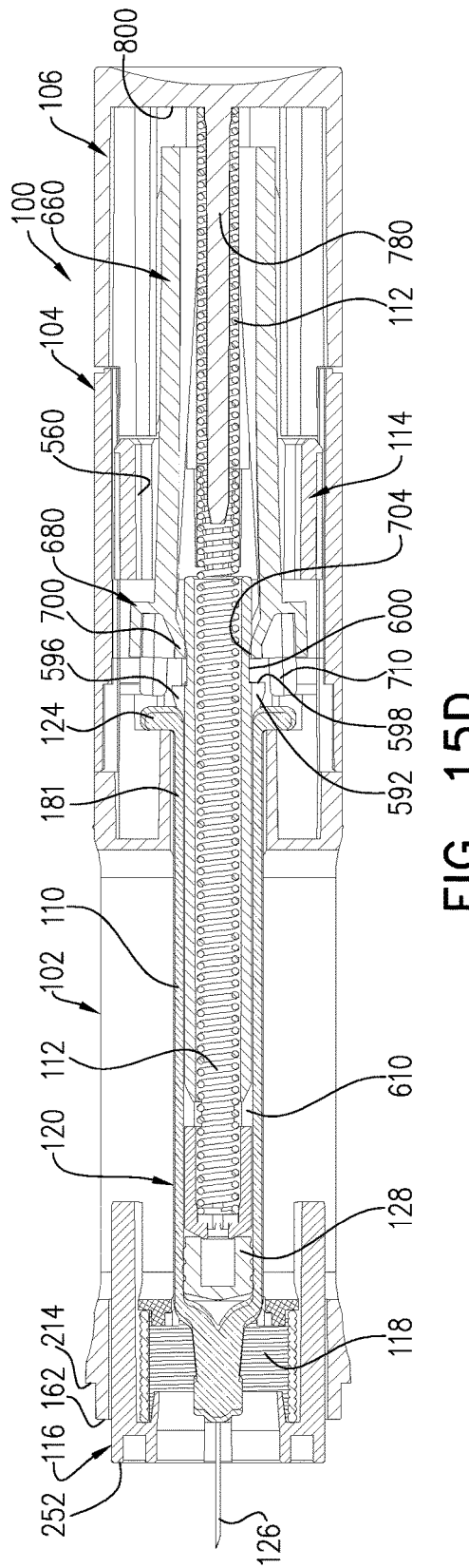
Figure 15G:
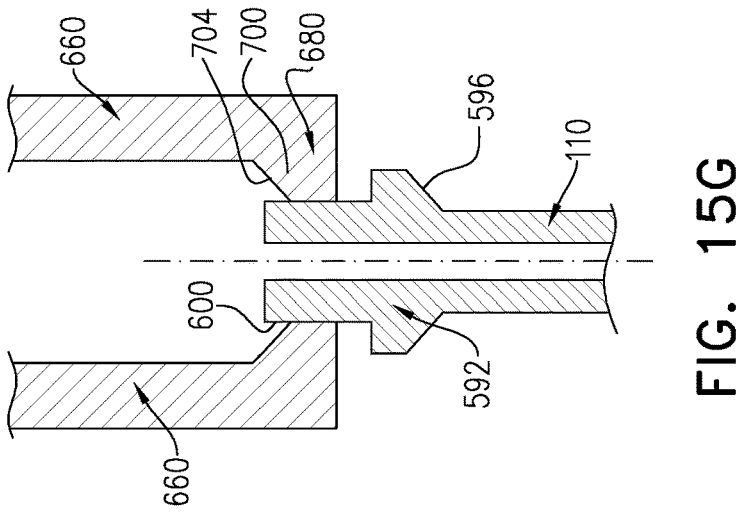
FIGS. 15E, 15F and 15G are simplified partial plan view illustrations of a transition between just prior to end of injection, during end of injection and just after end of injection of the plunger rod element of FIGS. 9A-9H relative to the rear housing portion of FIGS. 10A-10H.
Figure 15F:
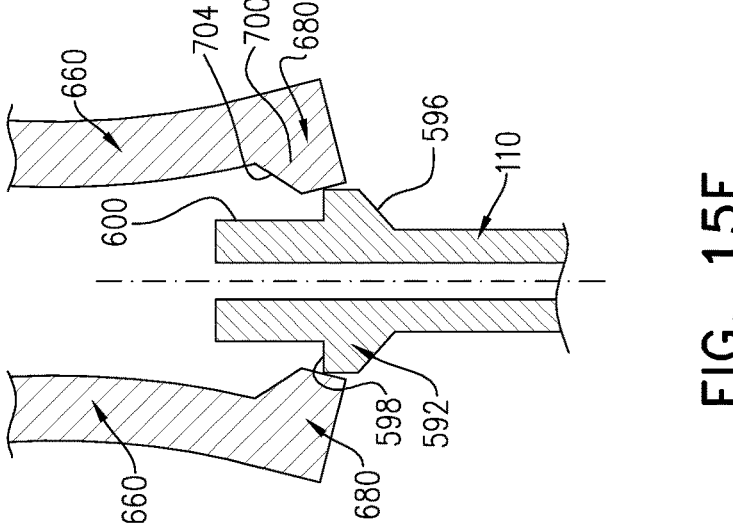
Figure 15E:
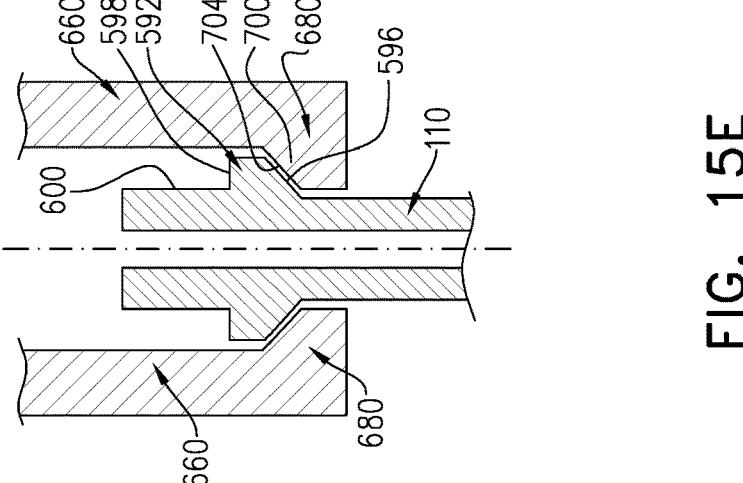

It is appreciated that all spatial relationships between the various components of the automatic injection device 100 remain the same as described hereinabove with respect to the injection operative orientation illustrated in FIGS. 14A-14G, besides the following spatial relationships:

It is seen in FIGS. 15C and 15D that the piston 128 has reached the forwardmost end of the barrel 122 of syringe 120, so that the entire amount of medicament is ejected therefrom in this operative orientation.

The user keeps pressing the automatic injection device 100 against the injection site in this operative orientation and thus the needle guard element 116 is still disposed in its rearwardmost position. the injection spring 112 biases the plunger rod element 110 forwardly.

It is a particular feature of an embodiment of the present invention, as particularly seen in FIGS. 15D-15G, that an audible indication is provided to the user at the end of injection process by means of engagement between the plunger rod element 110 and the rear housing portion 104. The transition between just prior to end of injection to after end of injection is specifically seen in FIGS. 15E-15G. As the plunger rod element 110 is forwardly longitudinally displaced along longitudinal axis 109, radially outwardly extending protrusions 592 of the plunger rod element 110 engage locking members 680 of longitudinal arms 660 of rear housing portion 104, such that forwardly facing tapered surface 596 of outwardly extending protrusions 592 abuts forwardly tapered inner surfaces 704 of locking members 680 just prior to end of injection as shown in FIG. 15E. Upon further forward displacement of the plunger rod element 110, radially outwardly extending protrusions 592 of plunger rod element 110 slide over forwardly tapered inner surfaces 704 of locking members 680 and causes outward deflection of longitudinal arms 660 of the rear housing 104, as seen in FIG. 15F. Immediately thereafter, locking elements 680 of longitudinal arms 660 of rear housing portion 104 snap over radially outwardly extending protrusions 592 of the plunger rod element 110, whereas wide portions 700 of locking members 680 engage recesses 600 of the plunger rod element 110, as seen in FIG. 15G, thereby providing an audible click as an indication to the user that the injection has ended.

It is a particular feature of an embodiment of the present invention that locking members 680 of the longitudinal arms 660 of the rear housing portion 104 are operative both for retaining the plunger rod element 110 in its rearwardmost position in storage operative orientation and for providing an audible indication to the user at the end of injection operative orientation.

Figures 16A, 16B:
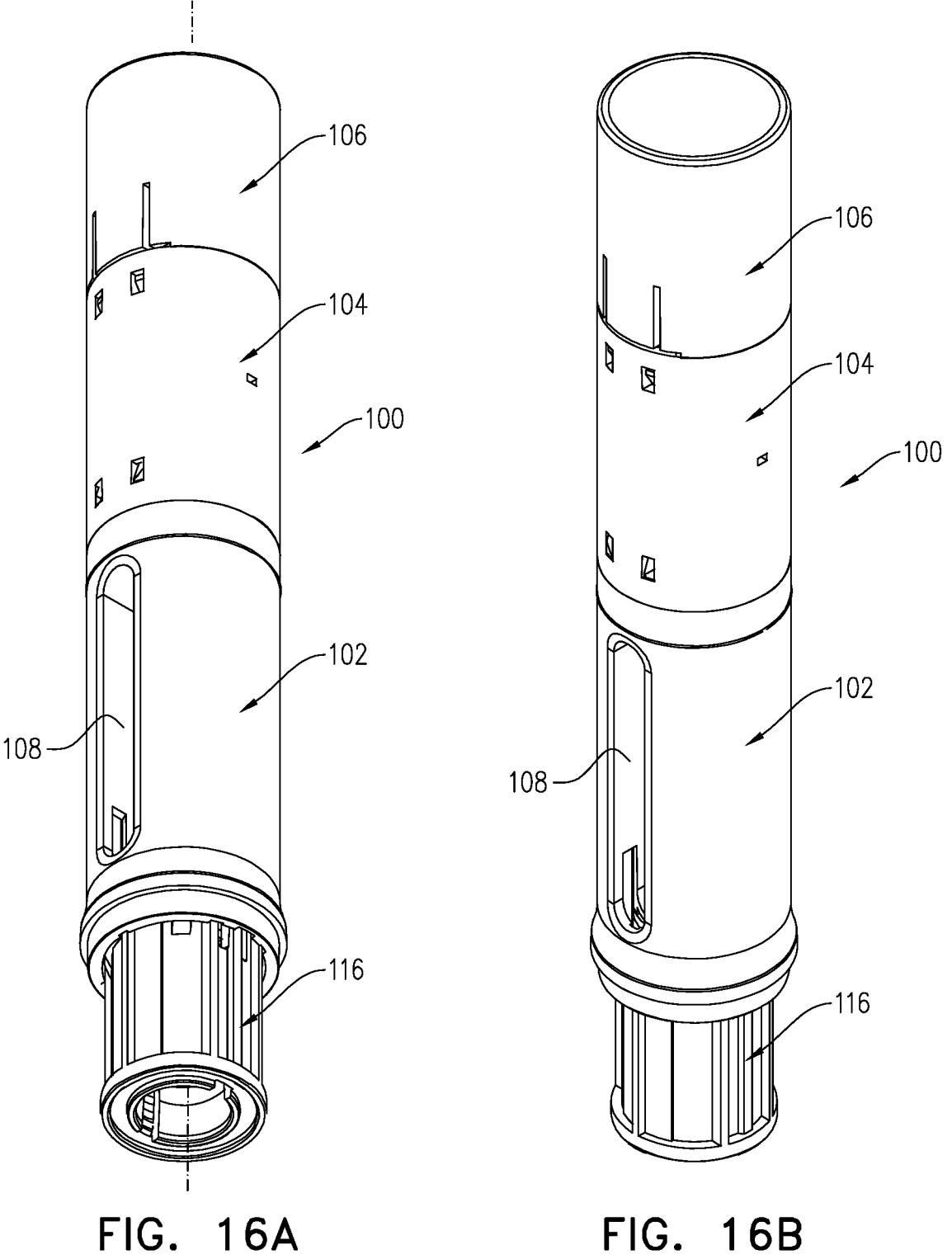
FIGS. 16A, 16B, 16C and 16D are simplified illustrations of the automatic injection device of FIGS. 1A-11G in a needle protection operative orientation, including a simplified perspective view, a simplified side plan view and two simplified side plan views with cut-out sections.
Figure 16C:
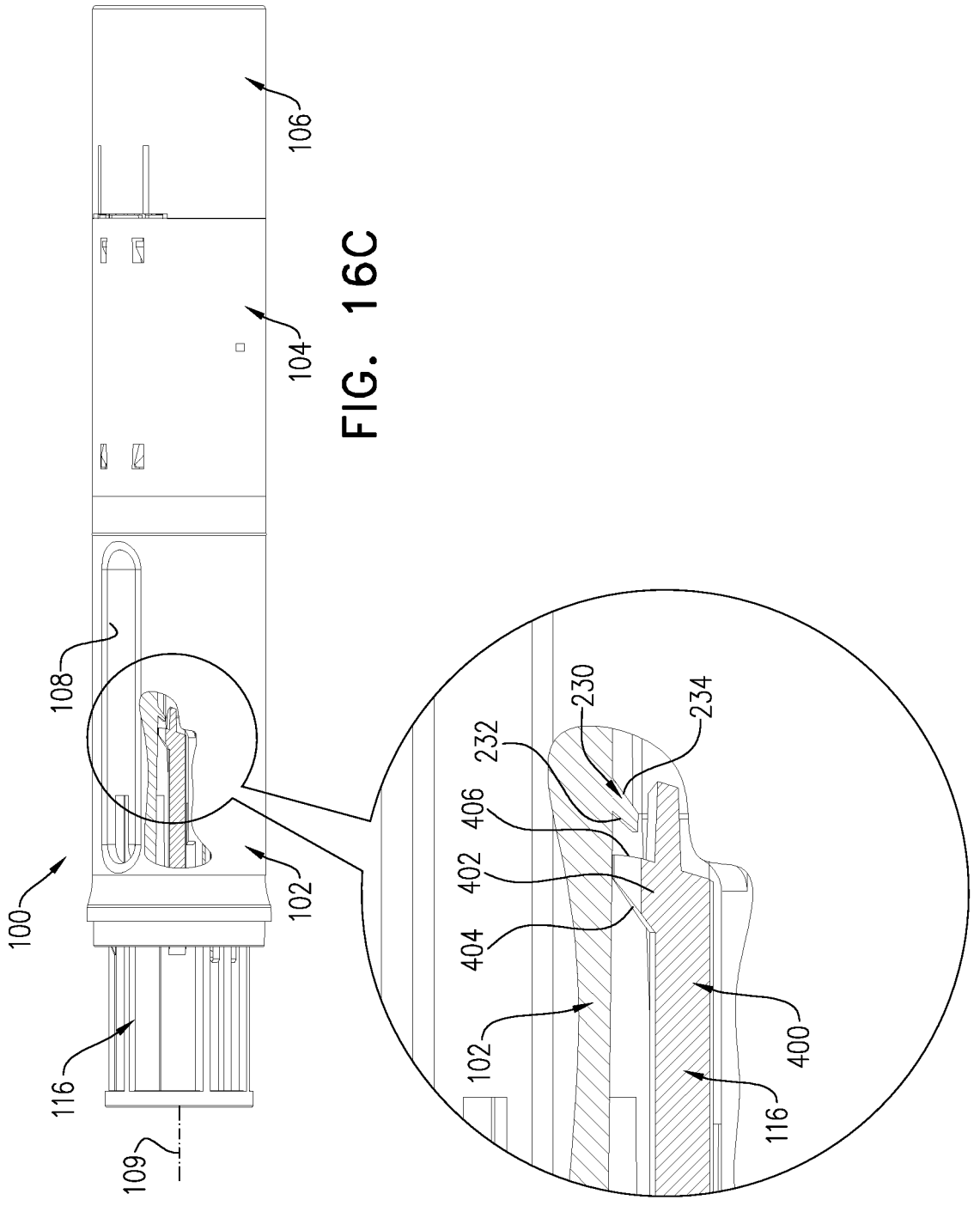
Figure 16D:
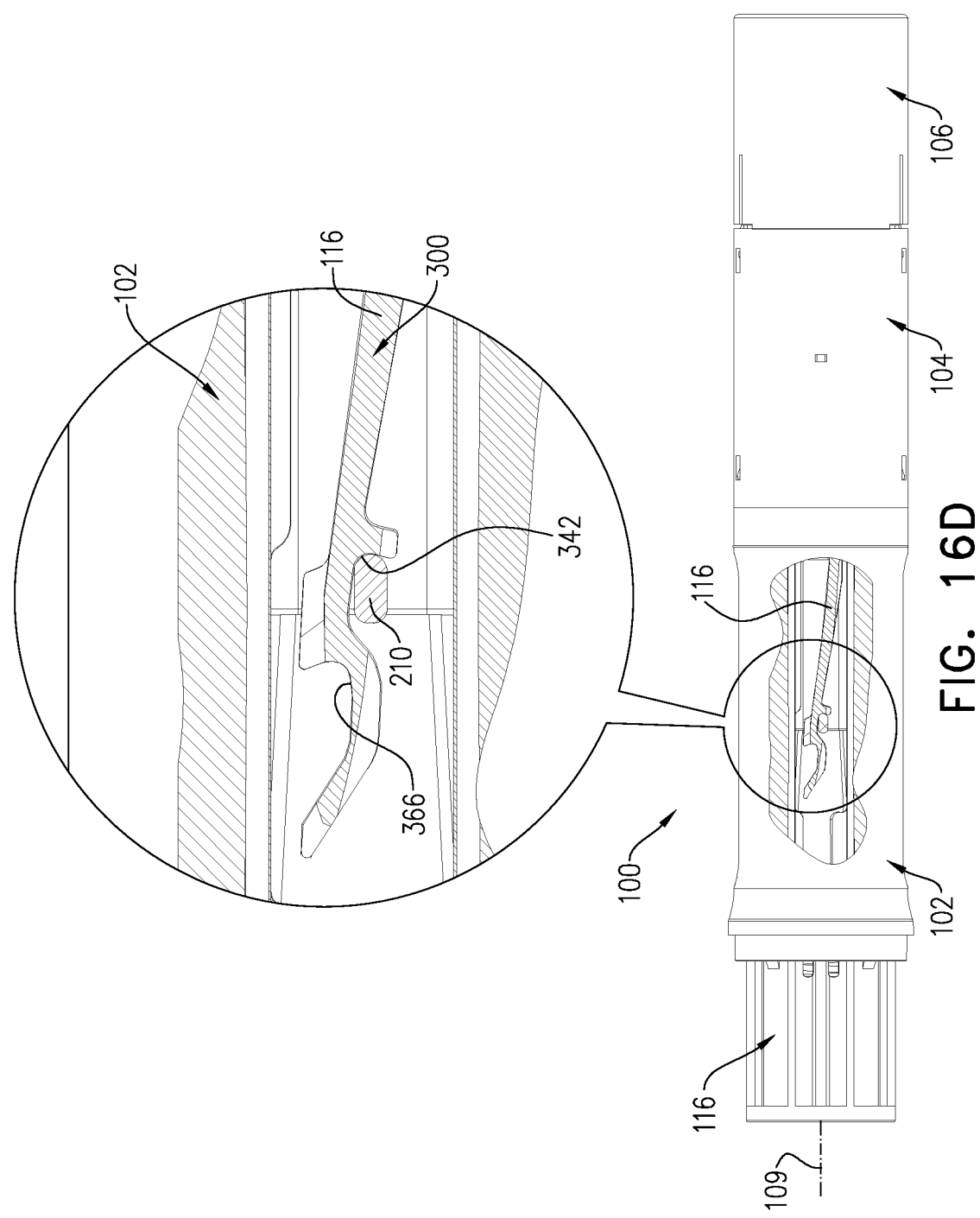
Figure 16E:
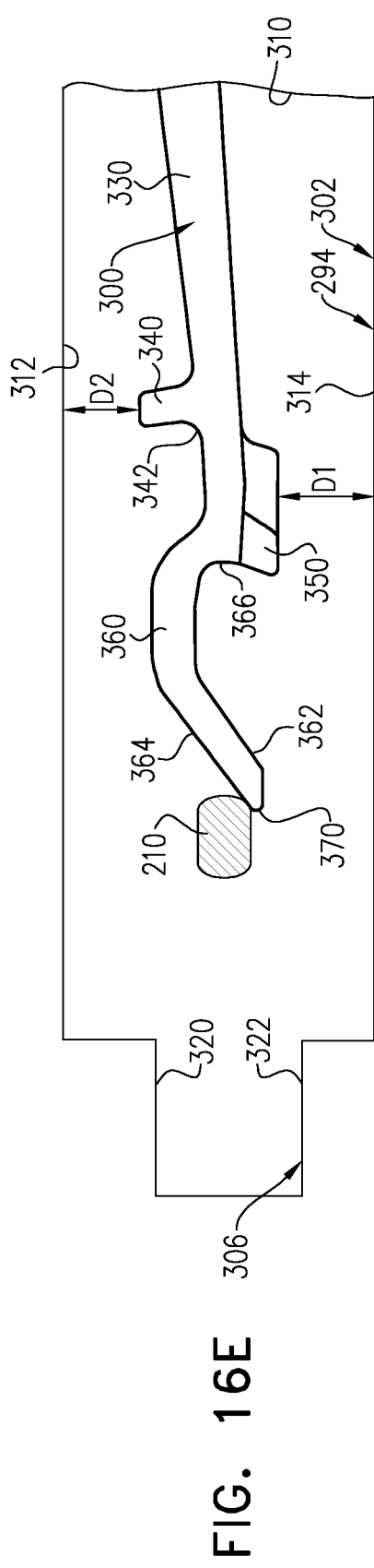
FIGS. 16E, 16F & 16G are simplified partial plan view illustrations of a transition between rearward position and forwardmost needle protection position of the needle guard element of FIGS. 5A-5J relative to the front housing portion of FIGS. 4A-4I.
Figure 16F:
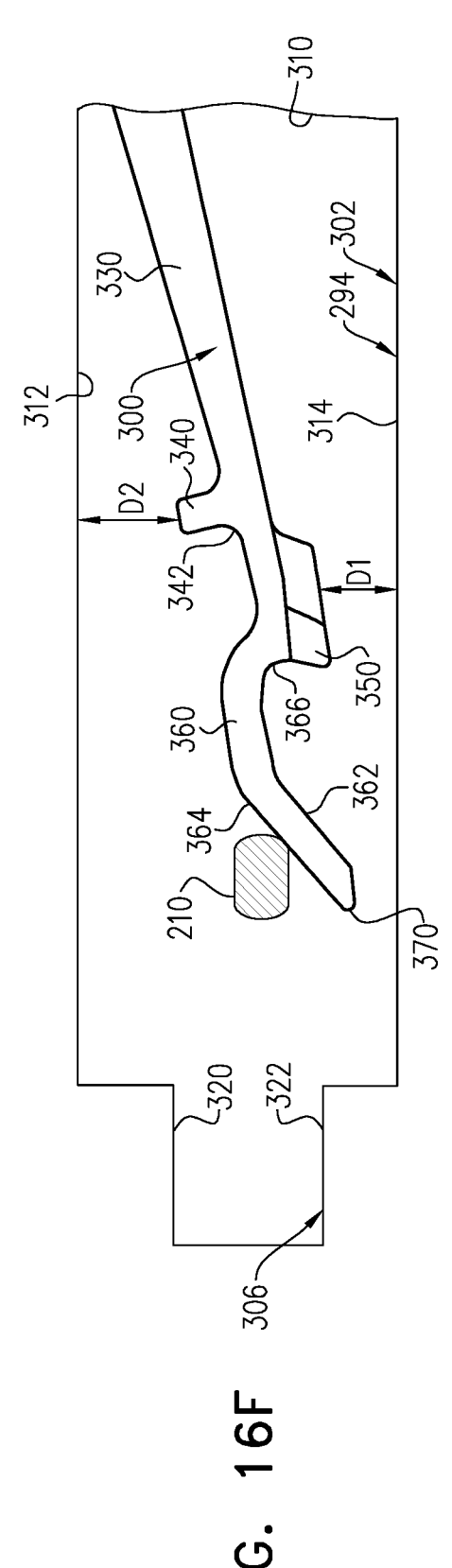
Figure 16G:
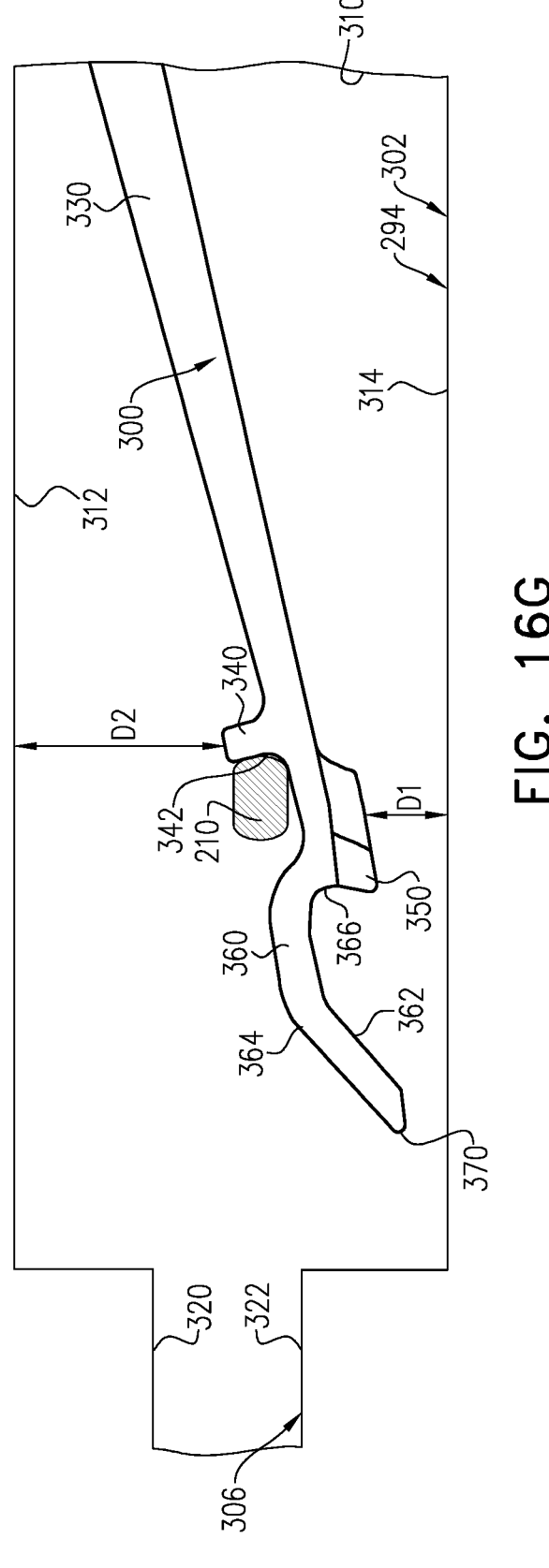

Reference is now made to FIGS. 16A, 16B, 16C and 16D, which are simplified illustrations of the automatic injection device 100 of FIGS. 1A-11G in a needle protection operative orientation, including a simplified perspective view, a simplified side plan view and two simplified two simplified side plan views with cut-out sections. Reference is additionally made to FIGS. 16E, 16F & 16G, which are simplified partial plan view illustrations of a transition between rearward position and forwardmost needle protection position of the needle guard element 116 of FIGS. 5A-5J relative to the front housing portion 102 of FIGS. 4A-4I.

It is appreciated that all spatial relationships between the various components of the automatic injection device 100 remain the same as described hereinabove with respect to the end of injection operative orientation illustrated in FIGS. 15A-15G, besides the following spatial relationships:

In this operative orientation, the automatic injection device 100 is fully disengaged from the injection site and the needle guard element 116 is fully extended to its forwardmost position, which is disposed forwardly with respect to the front housing portion 102 in comparison to the forward position of the needle guard element 116 as shown in FIGS. 12A-13C. In this forwardmost position of the needle guard element 116, the needle 126 is enclosed therewithin and protected.

When the needle guard element 116 is fully extended to its forwardmost needle protection position, the needle guard element 116 is prevented from rearward axial displacement relative to the front housing portion 102 so as to prevent needle exposure. The rearward displacement of the needle guard element 116 in this operative orientation is prevented since protrusion 230 of the front housing portion 102 is now disposed rearwardly of outwardly extending protrusion 402 of rearwardly extending arm 400 of the needle guard element 116, such that the needle guard element 116 can only be slightly rearwardly displaced up to abutment of rearwardly facing surface 406 of protrusion 402 with forwardly facing tapered surface 232 of protrusion 230. In comparison, it is noted that in FIGS. 12C and 12D, the protrusion 402 of the needle guard element 116 was disposed rearwardly of protrusion 230 of the front housing portion 102 and upon release of the automatic injection device 100 from the injection site, the needle guard element 116 is displaced more forwardly than it was in the storage operative orientation, thus protrusion 402 of the needle guard element 116 snaps over protrusion 230 of the front housing portion 102 and is now locked forwardly thereof and prevents exposure of the needle 126.

It is seen in FIGS. 16A-16G that the forward end of the needle guard element 116 is exposed and protrudes forwardly from the forward edge 162 of the front housing portion 102 to a second longitudinal extent, which is greater than the first longitudinal extent, as described with reference to FIGS. 12A-12K.

It is seen in FIGS. 16D-16G, that the needle guard element 116 is also prevented from forward displacement relative to the front housing portion 102.

It is a particular feature of an embodiment of the present invention that the needle guard element 116 is prevented from forward displacement both in storage operative orientation and in needle protection operative orientation due to engagement of the labyrinth protrusion 300 of the needle guard element 116 with the inwardly directed protrusion 210 of the front housing portion 102.

It is specifically seen in FIGS. 16D-16G, that the inwardly directed protrusion 210 of the front housing portion 102 in this operative orientation is seated within retaining portion 342 of the labyrinth protrusion 300, which is rearwardly spaced from retaining portion 366, in which it is seated in the storage operative orientation as shown in FIGS. 12C-12D.

It is a particular feature of an embodiment of the present invention that during forward longitudinal displacement of the needle guard element 116 relative to front housing portion 102, the inwardly directed protrusion 210 of the front housing portion 102 laterally deflects the labyrinth protrusion 300 in a second direction, opposite to the first direction, as shown in FIGS. 14F and 14G, and thus guides the labyrinth protrusion 300 such that inwardly directed protrusion 210 is seated within retaining portion 342.

It is specifically seen from the transition between FIGS. 16E, 16F and 16G that as the needle guard element 116 is forwardly displaced relative to the front housing portion 102, the labyrinth protrusions 300 forwardly displace relative to radially inwardly directed protrusions 210 of the front housing portion 102, and thus radially inwardly directed protrusions 210 which were disposed in third longitudinal portion 306 during injection are now displaced rearwardly and slide along convex surface 364 of curved hook extension 360, due to the fact that curved hook extension 360 is convex in shape and forward directing tip 370 is directed towards second side edge 314. It is specifically seen in FIGS. 16E and 16F how inwardly directed protrusions 210 slide rearwardly over convex surfaces 364 of curved hook extensions 360 up to a position in which protrusions 210 are seated within retaining portions 342 as seen in FIG. 16G, in which position any further forward displacement of the needle guard element 116 is prevented.

It is noted that during forward displacement of the needle guard element 116 relative to the front housing portion 102, the labyrinth protrusion 300 is deflected laterally in a second direction, opposite to the first direction as shown in FIGS. 14F and 14G, toward second side edge 314, such that distance D1 decreases and distance D2 increases accordingly.

This invention generally relates to an automatic injection device for parenteral administration of substances (e.g., a medication) to a living organism (human or animal). The administration may be delivered into the subcutaneous tissue.

The invention is further related to, but is not limited to a self-administration of patients with chronic diseases such as rheumatoid arthritis (RA), multiple sclerosis (MS), HIV, and growth hormone deficiency.

It is appreciated that in accordance with an embodiment of the present invention the medicament is enclosed in a pre-filled syringe, but it can alternatively be used with other drug enclosures such as vials or ampoules, where a vial adaptor or an ampoule adaptor is used to reconstitute, mix, or pump the drug into the syringe prior to injection. The pre-filled syringe can be either a conventional one chambered pre-filled syringe with a ready-to-inject liquid form drug, or it can be a multiple-chambered pre-filled syringe.

It will be appreciated by persons skilled in the art that the present invention is not limited by what has been particularly shown and described hereinabove. Rather the scope of the present invention includes both combinations and sub-combinations of various features described hereinabove as well as variations and modifications thereof which are not in the prior art.

The invention claimed is:

1. An automatic injection device comprising:
a housing arranged along a longitudinal axis and having a forward end and a rearward end, configured to receive a syringe including at least one syringe piston and a needle configured to be coupled to a forward end thereof, said syringe is static with respect to said housing;
a plunger rod adapted to be retained with respect to said housing in an initial operative orientation;
at least one resilient element arranged to forwardly bias said plunger rod relative to said syringe, said at least one resilient element is at least partially disposed within said plunger rod;
a needle shield adapted for selectable axial displacement with respect to said housing along said longitudinal axis, whereas rearward displacement of said needle shield exposes said needle and forward displacement of said needle shield covers said needle;
and a trigger element configured to be axially rearwardly displaced upon rearward displacement of said needle shield relative to said housing and thereby allow forward displacement of said plunger rod relative to said syringe under the urge of said at least one resilient element,
wherein said trigger element is operatively engageable with a housing portion, said housing portion forming part of said housing,
and wherein said housing portion prevents axial displacement of said plunger rod relative to said syringe.

2. The automatic injection device according to claim 1, and wherein said trigger element is rearwardly spaced from a rearward end of said needle shield in an initial operative orientation and is configured to prevent forward displacement of said plunger rod under the biasing force of said at least one resilient element up to said rearward displacement of said needle shield relative to said housing.

3. The automatic injection device according to claim 1, and wherein said needle shield is prevented from forward displacement relative to said housing both in an initial operative orientation and in a final operative orientation, when the needle is protected by said needle shield, by means of engagement of a resilient needle shield portion with a protrusion formed on said housing.

4. The automatic injection device according to claim 1, and wherein an audible indication is provided at an end of injection operative orientation by engagement of said plunger rod with said housing.

5. The automatic injection device according to claim 1, and wherein said housing comprises at least one locking arm, which is operative both for retaining said plunger rod in a rearward position and for providing an audible indication for an end of injection.

6. An automatic injection device comprising:
a housing arranged along a longitudinal axis and having a forward end and a rearward end, configured to receive a syringe including at least one syringe piston and a needle configured to be coupled to a forward end thereof;
a plunger rod adapted to be retained with respect to said housing in an initial operative orientation;

at least one resilient element arranged to forwardly bias said plunger rod relative to said syringe;

a needle shield adapted for selectable axial displacement with respect to said housing along said longitudinal axis, whereas rearward displacement of said needle shield exposes said needle and forward displacement of said needle shield covers said needle;

and a trigger element, which is rearwardly spaced from a rearward end of said needle shield in an initial operative orientation and is configured to prevent forward displacement of said plunger rod under the biasing force of said at least one resilient element up to rearward displacement of said needle shield relative to said housing, wherein said trigger element is operatively engageable with a housing portion, said housing portion forming part of said housing, and wherein said housing portion prevents axial displacement of said plunger rod relative to said syringe.

7. The automatic injection device according to claim 6, and wherein said trigger element is configured to be axially rearwardly displaced upon said rearward displacement of said needle shield relative to said housing and thereby allow forward displacement of said plunger rod relative to said syringe under the urge of said at least one resilient element.

8. The automatic injection device according to claim 6, and wherein said at least one resilient element is at least partially disposed within said plunger rod.

9. The automatic injection device according to claim 6, and wherein said needle shield is prevented from forward displacement relative to said housing both in said initial operative orientation and in a final operative orientation, when the needle is protected by said needle shield, by means of engagement of a resilient needle shield portion with a protrusion formed on said housing.

10. The automatic injection device according to claim 6, and wherein said syringe is static with respect to said housing.

11. The automatic injection device according to claim 6, and wherein said housing comprises at least one locking arm, which is operative both for retaining said plunger rod in a rearward position and for providing an audible indication for an end of injection.

12. An automatic injection device comprising:

a housing arranged along a longitudinal axis and having a forward end and a rearward end and having an inwardly extending protrusion formed thereon, said housing is configured to receive a syringe including at least one syringe piston and a needle configured to be coupled to a forward end thereof;

a plunger rod adapted to be retained with respect to said housing in an initial operative orientation;

at least one resilient element arranged to forwardly bias said plunger rod relative to said syringe;

a needle shield adapted for selectable axial displacement with respect to said housing along said longitudinal axis, whereas rearward displacement of said needle shield exposes said needle and forward displacement of said needle shield covers said needle;

and wherein said needle shield is prevented from forward displacement relative to said housing both in an initial operative orientation and in a final operative orientation, when the needle is protected by said needle shield, by means of engagement of a resilient needle shield portion with said inwardly extending protrusion.

13. The automatic injection device according to claim 12, also comprising a trigger element, which is rearwardly spaced from a rearward end of said needle shield in said initial operative orientation and is configured to prevent forward displacement of said plunger rod under the biasing force of said at least one resilient element up to rearward displacement of said needle shield relative to said housing.

14. The automatic injection device according to claim 13, and wherein said trigger element is configured to be axially rearwardly displaced upon said rearward displacement of said needle shield relative to said housing and thereby allow forward displacement of said plunger rod relative to said syringe under the urge of said at least one resilient element.

15. The automatic injection device according to claim 13, and wherein said trigger element is operatively engageable with a housing portion, wherein said housing portion prevents axial displacement of said plunger rod relative to said syringe.

16. The automatic injection device according to claim 12, and wherein said at least one resilient element is at least partially disposed within said plunger rod.

17. The automatic injection device according to claim 12, and wherein said protrusion is configured to laterally displace said resilient needle shield portion in a first direction during rearward displacement of said needle shield relative to said housing and in a second direction during forward displacement of said needle shield relative to said housing.

18. The automatic injection device according to claim 12, and wherein said syringe is static with respect to said housing.

* * * * *